United States Patent
Müller et al.

(10) Patent No.: US 10,040,810 B2
(45) Date of Patent: Aug. 7, 2018

(54) DERIVATIVES OF BISACYLPHOSPHINIC ACID, THEIR PREPARATION AND USE AS PHOTOINITIATORS

(71) Applicant: BASF SE, Ludwigshafen (DE)

(72) Inventors: Georgina Müller, Zurich (CH); Hansjörg Grützmacher, Wettswil a.A. (CH); Kurt Dietliker, Allschwil (CH)

(73) Assignee: BASF SE (DE)

( * ) Notice: Subject to any disclaimer, the term of this patent is extended or adjusted under 35 U.S.C. 154(b) by 95 days.

(21) Appl. No.: 14/653,579

(22) PCT Filed: Dec. 16, 2013

(86) PCT No.: PCT/EP2013/076707
§ 371 (c)(1),
(2) Date: Jun. 18, 2015

(87) PCT Pub. No.: WO2014/095724
PCT Pub. Date: Jun. 26, 2014

(65) Prior Publication Data
US 2016/0039851 A1 Feb. 11, 2016

Related U.S. Application Data

(60) Provisional application No. 61/739,016, filed on Dec. 19, 2012.

(30) Foreign Application Priority Data

Dec. 19, 2012 (EP) ................................. 12197968

(51) Int. Cl.
*C07F 9/30* (2006.01)
*C08F 2/50* (2006.01)
(Continued)

(52) U.S. Cl.
CPC ............ *C07F 9/307* (2013.01); *C07F 9/3252* (2013.01); *C07F 9/34* (2013.01); *C07F 9/36* (2013.01);
(Continued)

(58) Field of Classification Search
CPC .......... C07F 9/307; C07F 9/3252; C07F 9/34; C07F 9/36; C09D 135/02; C08F 2/50; G03F 7/029; C09J 181/02; C08G 75/08
See application file for complete search history.

(56) References Cited

U.S. PATENT DOCUMENTS 5,368,985 A * 11/1994 Rutsch .................. C07F 9/5337
430/103
6,103,453 A 8/2000 Prantl et al.
(Continued)

FOREIGN PATENT DOCUMENTS

CN 102405239 A 4/2012
CN 102471150 A 5/2012
(Continued)

OTHER PUBLICATIONS

Chinese Office Action for application No. 201380066680.0, dated Aug. 25, 2016.
(Continued)

*Primary Examiner* — Mark Eashoo
*Assistant Examiner* — Jessica M Roswell
(74) *Attorney, Agent, or Firm* — Drinker Biddle & Reath LLP

(57) ABSTRACT

Bisacylphosphine oxide or bisacylphosphine sulfide compounds of formula (I) or (II)

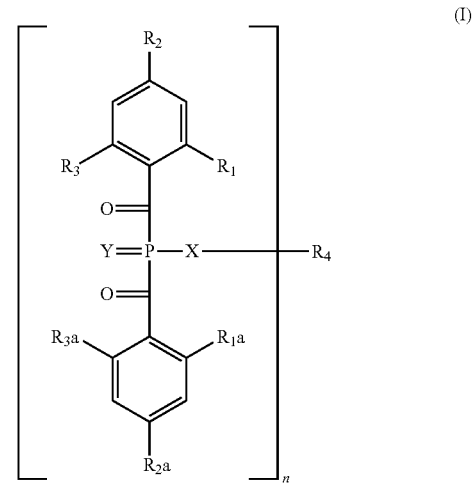

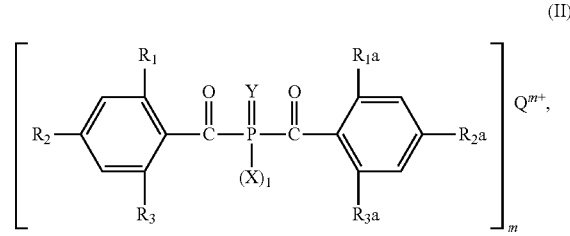

wherein
$R_1$, $R_2$, $R_3$, $R_{1a}$, $R_{2a}$ and $R_{3a}$ independently of each other are $C_1$-$C_4$alkyl, $C_1$-$C_4$alkoxy or halogen; X is O, $NR_5$ or S; or, if $R_4$ is Cl, F or Br, X is a direct bond; Y is O or S; n is 1 or 2; if n is 1, for example is hydrogen, $(CO)R_6$, $(CO)OR_6$, $(CO)NR_5R_6$, $(SO_2)$—$R_6$, $C_1$-$C_{28}$alkyl, $R_4$, if n=2, is for example $C_1$-$C_{18}$alkylene; $R_5$ is for example hydrogen, or $C_1$-$C_{12}$alkyl; $R_6$ is for example $C_1$-$C_{12}$alkyl; $R_7$, $R_8$ and $R_9$ independently of each other for example are $C_1$-$C_4$alkyl; $R_{10}$ is for example $C_2$-$C_{18}$alkylene; $X_1$, is O or S; m is 1, 2 or 3; Q represents one or two inorganic or (Continued)

organic cations with a charge of $m^+$; are suitable photoinitiators, available by a claimed process.

16 Claims, No Drawings

(51) Int. Cl.
  *C09D 135/02* (2006.01)
  *C07F 9/32* (2006.01)
  *C07F 9/34* (2006.01)
  *C07F 9/36* (2006.01)
  *G03F 7/029* (2006.01)

(52) U.S. Cl.
  CPC .............. *C08F 2/50* (2013.01); *C09D 135/02* (2013.01); *G03F 7/029* (2013.01)

(56) References Cited

U.S. PATENT DOCUMENTS

| | | | |
|---|---|---|---|
| 8,633,258 B2 | 1/2014 | Bishop | |
| 9,181,358 B2 | 11/2015 | Gruetzmacher et al. | |
| 2005/0222294 A1 | 10/2005 | Noe et al. | |
| 2012/0115963 A1 | 5/2012 | Gruetzmacher et al. | |

FOREIGN PATENT DOCUMENTS

| | | | | |
|---|---|---|---|---|
| CN | 102924509 A | | 2/2013 | |
| JP | H8245657 A | | 9/1996 | |
| JP | H11322819 A | | 11/1999 | |
| JP | 2005526725 A | | 9/2005 | |
| JP | 2012524128 A | | 10/2012 | |
| WO | WO 2010/121387 | * | 10/2010 | ................ C08F 2/24 |
| WO | WO 2011/003772 | * | 1/2011 | ................ C08F 8/40 |
| WO | WO 2012/012067 | * | 1/2012 | ............. G03F 7/029 |

OTHER PUBLICATIONS

English Translation of Chinese Office Action for application No. 201380066680.0, dated Aug. 25, 2016.
English Translation of Japanese Office Action for Japanese Application No. 2015-548406, dated Dec. 19, 2017.
European Office Action for European Application No. 13805403.6, dated Dec. 21, 2017.
Keglevich, G., et al., "The Synthesis of Optically Active P-Heterocycles", Heteroatom Chemistry, 2010, vol. 21, No. 4, pp. 271-277.
Mu, Y., et al., "Design and Synthesis of Chrial and Racemic Phosphonate-Based Haptens for the Induction of Aldolase Catalytic Antibodies", Bioorganic & Medicinal Chemistry, 1997, vol. 5, No. 7, pp. 1327-1337.

* cited by examiner

DERIVATIVES OF BISACYLPHOSPHINIC ACID, THEIR PREPARATION AND USE AS PHOTOINITIATORS

CROSS-REFERENCE TO RELATED APPLICATIONS

This application is a national stage application (under 35 U.S.C. § 371) of PCT/EP2013/076707, filed Dec. 16, 2013, which claims benefit of European Application No. 12197968.6, filed Dec. 19, 2012, and U.S. Application No. 61/739,016, filed Dec. 19, 2012, all of which are incorporated herein by reference in their entirety.

The present invention relates to new photoinitiators derived from bisacylphosphonic acid, the preparation and use of such compounds.

Mono- and bisacylphosphine oxides are an important class of photoinitiators that find widespread use in many applications. Bisacylphosphine oxide photoinitiator compounds are for example described in U.S. Pat. No. 4,737,593.

Most mono- and bisacylphosphine oxide photoinitiators known today are phosphine oxides carrying besides the acyl groups one or two carbon substituents on the phosphorus atom. The selection of this substitution pattern is due to the good performance of these compounds as photoinitiators, but also to the relatively easy synthetic access to such compounds, which are mostly obtained using suitable aryl or alkyl phosphines derivatives as starting materials.

Acylphosphine oxide compounds carrying one or two hetero atom substituents besides one or two acyl substituents on phosphorus have also been reported for use as photoinitiators.

The use of P-alkoxy substituted monoacylphosphine oxides as photoinitiators has been claimed in U.S. Pat. No. 4,710,523. This document describes the synthesis of monoacylphosphine oxides carrying one alkoxy substituent on phosphorus (monoacyl phosphinic acid esters). These compounds are obtained via an Arbusov reaction of an acyl chloride with a suitable phosphinous acid ester.

By a similar reaction using a phosphonous acid diester instead of a phosphinous acid ester, the corresponding monoacyl phosphonic acid esters derivatives carrying two alkoxy substituents on phosphorus are available as reported in the same patent application.

The corresponding monoacyl phosphinic acid and monoacylphosphonic acid derivatives and their respective metal or ammonium salts are reported as photoinitiators in U.S. Pat. No. 4,719,297. The same application also claims monoacylphosphinic acid amides for use as photoinitiator.

A particular structural type of monoacylphosphinic acid ester derivatives are claimed in U.S. Pat. No. 5,096,935. In these structures the aryl ester group is linked to a P-aryl substituent forming a polycyclic system (9,10-dihydro-9-oxa-10-phosphaphenanthrene 10-oxide, DOPO). The corresponding acyl (hydroxybiphenyl) phosphinic acid metal salts are obtained by alkaline hydrolysis of these compounds and are also claimed as photoinitiators in U.S. Pat. No. 5,407,969.

The relatively easy access to monoacylphosphinic acid derivatives via an Arbusovreaction followed by dealkylation, and the numerous possibilities to further transform the free acid into other derivatives possessing specific properties, such as for example the corresponding acid chloride, resulted in the synthesis of a variety of different monoacylphosphinic acid and monoacylphosphonic acid derivatives (U.S. Pat. No. 7,511,084). If the phosphinic acid is transformed into a reactive species via introduction of a leaving group, further derivatives are available. As an example, the reaction with diols gives bifunctional monoacylphosphinic acid derivatives, and with primary or secondary amines monoacylphosphinic acid amide are obtained (WO2003068785).

Suitable modification of the free acid allows for the synthesis of polymerizable polymeric photoinitiators containing monoacylphosphinic acid derivatives as photoactive compounds (WO2010133381). Silyloxy esters claimed in U.S. Pat. No. 5,210,110 are obtained either by transesterifiation of the corresponding monoacylphosphinic and monoacyalphosphonic acid ester derivatives or via an Arbusov reaction with a tris(trialkylsilyl) phosphine. Poly (ethylene glycol) esters are claimed as water-compatible photoinitiators for waterborne inkjet inks in U.S. Pat. No. 7,976,148.

In contrast to monoacyl phosphinic acid derivatives, only very few bisacylphosphinic acid derivatives are known so far. This is particularly due to the fact that these compounds cannot be prepared by a simple synthetic protocol such as the Arbusovreaction discussed before. In fact, only very few synthetic accesses to such compounds have been published so far.

The use of a bisacylphosphosphinic acid aryl esters, e.g. bis(2,6-dichlorobenzoyl)-(4-butylphenoxy)-phosphine oxide, as photoinitiator in dental applications has been reported in U.S. Pat. No. 7,097,456.

Bisacylphosphosphinic acid ester derivatives, in particular structures carrying a reactive or co-polymerizable group on the ester moiety, have been generically described in WO03068785 (BASF). However, no example is given or is a synthetic access to such compounds described.

P-alkoxy or P-aryloxy substituted bisacylphosphine oxides have recently been claimed as liquid bisacylphosphine oxide photoinitiators in WO02012012067. The compounds are obtained via acylation of a dialkyl hydrogen phosphite, followed by a zinc bromide catalysed acylation/ dealkylation reaction sequence. The harsh reaction conditions limit the utility of this approach to the synthesis of structurally simple O-alkyl or O-aryl derivatives.

Although the monoacyl diarylphosphine oxides and bisacyl aryl phosphine oxides are versatile photoinitiators for many applications, the use of these compounds has some limitations. For example, it is well known that both mono- and bisacylphosphine oxides have a limited chemical stability in the presence of nucleophiles such amines (Baxter, J E.; Davidson, R. S., Hageman, H. J., Hakvoort, G. T. M. Overeem, T. Polymer 1988, 29, 1575) or in basic aqueous solution. This chemical instability limits the use of this class of photoinitiators to formulations not containing such nucleophilic compounds, and excludes for example the use of amine co-initiators frequently added in radiation curable formulation in order to overcome oxygen inhibition, or the use of amine-modified acrylate binders.

Furthermore it is well known to the person skilled in the art that particularly bisacylphosphine oxides are difficult to dissolve and incorporate into certain formulations. Thus, the preparation of radiation curable formulations containing these photoinitiators is often a tedious process, requiring a long time and/or higher temperatures in order to homogeneously incorporate the photoinitiators in the formulation. Similarly, most bisacylphosphine oxides known are hardly or not at all compatible with an aqueous environment as it is used for water-borne formulations. An exception is the commercial product Irgacure® 819 DW which is a dispersion of bis(2,4,6-trimethylbenzoyl)-phenyl phosphine oxide (Irgacure® 819) in water. However, the use of dispersant agents is not acceptable in all application.

These constraints are mostly due to the limited structural variations of bisacylphosphine oxide photoinitiators that are available by a straightforward synthetic access. In fact most bisacylphosphine oxide structures known so far either have a substituted or nonsubstituted aryl or alkyl substituent on the phosphorus atom. The structural variations of these substituents are limited to those functionalities that are compatible with the synthetic process.

Attempts to overcome these limitations have been reported. As an example, the introduction of suitable substituents on the aroyl moieties allows the preparation of bisacylphosphine oxides with improved solubility in good compatibility with aqueous formulations (U.S. Pat. No. 7,714,034). However the introduction of these substituents requires a multi-step synthesis of suitable aroyl chlorides used in the synthesis of these bisacylphosphine oxides. The complexity of the process and the additional costs created make this approach not attractive for most applications.

Another approach allowing the introduction of different substituents on the phosphorus atom has been reported in WO2006056541. A broad variety of substituents can be introduced via the alkylation of an intermediate bis(acyl) phosphide derivative with a suitable alkylating agent, followed by oxidation of the bis(acyl)phosphine to the corresponding bisacylphosphine oxide. The compounds obtained may be used as such as photoinitiators, or may be further modified in order to obtain derivatives with suitable properties. While the synthesis reported in this application is easy and straightforward, it is limited to phosphine oxides carrying carbon substituents on the phosphorus atom. Although compounds with improved properties regarding solubility and incorporation into formulations can be obtained, other properties such as stability towards nucleophilic attack remain on the level typical for P-aryl or P-alkyl substituted bis(acyl)phosphine oxides.

While the preparation of liquid bisacylphosphinic acid ester oxide photoinitiators as claimed in the WO02012012067 is desirable in view of the aforementioned limitations regarding solubility and incorporation ability, a more flexible approach allowing the easy fine tuning of application properties is highly desirable. This is especially true in view of the fact that WO 2012012067 discloses only bis(2,4,6trimethylbenzoyl)-n-butoxy phosphine oxide, however compounds of this class carrying short or medium alkyl chains, such as for example an ethyl or a hexyl group, are solid and not liquid compounds. Furthermore this approach does not give a simple access to the corresponding bisacylphosphinic acids or its metal or ammonium salts which are expected to be useful as photoinitiators with a high solubility/compatibility with aqueous systems.

As it has been discussed before, monoacylphosphinic and phosphonic acids can be easily prepared, and compounds possessing a wide variety of properties, including for example liquid or water soluble compounds, are available.

However, it is well-known to the person skilled in the art that mono- and bisacylphosphine oxides differ in their application properties. The fact that the absorption spectrum of monoacylphosphine oxides is blue-shifted as compared to the absorption spectrum of bisacylphosphine oxides can be advantageous in certain applications, for example for the curing of white pigmented lacquers where monoacylphosphine oxides usually induce a lower residual yellowness after cure than bisacylphosphine oxide photoinitiators. On the other hand, bisacylphosphine oxide photoinitiators generally provide a higher curing efficiency than monoacylphosphine oxides, since this class of photoinitiators can provide four initiating radicals upon irradiation, while monoacylphosphine oxides only provide two initiating radicals. Thus for some applications such as for example the curing of white pigmented formulations it would be desirable to combine the blue-shifted absorption properties of monoacylphosphine oxides with the high curing efficiency of bisacylphosphine oxides.

For other applications where the use of light of the near visible part of the spectrum is crucial, such as for example LED lamps emitting blue light, the more red-shifted absorption spectra of bisacylphosphine oxides is advantageous as compared to that of the monoacylphosphine oxides due to the better use of light. For such applications it would be desirable to have bisacylphosphine oxide photoinitiators with an even more red-shifted absorption spectrum.

Thus it becomes clear that bisacylphosphine oxide derivatives cannot be substituted by the more easily accessible monoacyl derivatives in many applications due to the different application properties including the lower curing performance of the latter.

It is highly desirable to have a simple and straightforward access to a wide variety of differentially substituted bisacylphosphinic acid derivatives, as it is the case for monoacylphosphinic acid derivatives. Moreover, it is highly desirable to introduce other hetero atom substituents than oxygen claimed in WO 2012012067 on phosphorus, since the heteroatom is expected to have a significant influence on curing properties including the absorption spectrum and other application features of the corresponding photoinitiators.

Therefore there is a need for novel synthetic protocols that allow the access to bisacylphosphinic acid derivatives. The term "bisacylphosphinic acid derivatives" as used here includes bisacylphosphinic acid and its salts, bisacylphosphinic acid esters, bisacylphosphinic acid amide, bisacylphosphinic acid thioesters and the like. Similarly the term "bisacylphosphinic acid derivatives" as used here also includes the corresponding bisacylthiophosphonic acid derivatives, bisacylphosphinic thioacid derivatives, or bisacylthiophosphinic thioacid derivatives.

Such compounds are expected to be efficient photoinitiators on their own, or may be used as easily accessible building blocks for the further design of photoinitiating species. The latter transformation allows to introduce additional properties, such as for example high compatibility with a very polar (e.g. water) or very non-polar (e.g. silanes) environment, low volatility, low extractables or low migration properties. Ionic compounds possessing certain types of counter ions, well-known to the one skilled in the art, can provide the characteristic properties of ionic liquids, which can be advantageous for handling and certain applications.

Thus the purpose of the present patent application is to provide a simple and straightforward synthetic access to such compounds, their use as photoinitiators or as building-block for the further design of multifunctional or co-reactive photoinitiators.

Subject of the present invention are compounds of the formula (I) or (II)

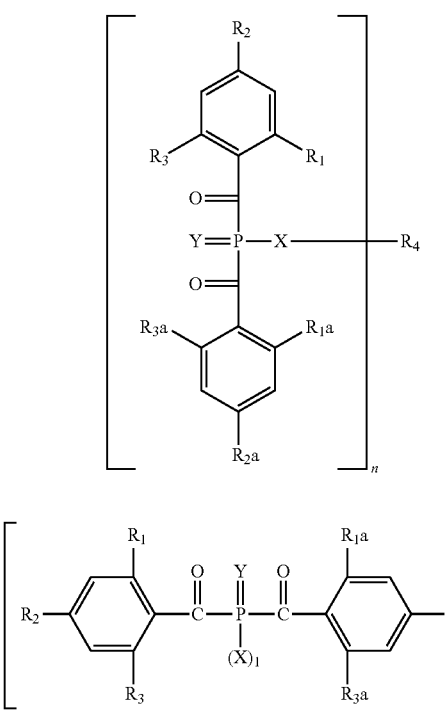

(I)

(II)

wherein $R_1$, $R_2$, $R_3$, $R_{1a}$, $R_{2a}$ and $R_{3a}$ independently of each other are $C_1$-$C_4$alkyl, $C_1$-$C_4$alkoxy or halogen;

X is O, $NR_5$ or S; or, if $R_4$ is Cl, F or Br, X is a direct bond;

Y is O or S;

n is 1 or 2;

$R_4$, if n is 1, is hydrogen, $(CO)R_6$, $(CO)OR_6$, $(CO)NR_5R_6$, $(SO_2)$—$R_6$, $[Si(R_7)(R_8)]_o$—$Si(R_7)(R_8)(R_9)$, $[Si(R_7)(R_8)$—$O]_o$—$Si(R_7)(R_8)(R_9)$, $C_1$-$C_{28}$alkyl, $C_2$-$C_{28}$alkyl which is interrupted by one or more O, $NR_5$, S, (CO), (CO)O, or $SO_2$; wherein said $C_1$-$C_{28}$alkyl or interrupted $C_2$-$C_{28}$alkyl is unsubstituted or substituted by one or more substituents selected from the group consisting of OH, halide, $C_6$-$C_{14}$aryl, $[Si(R_7)(R_8)]_o$—$Si(R_7)(R_8)(R_9)$, $[Si(R_7)(R_8)$—$O]_o$—$Si(R_7)(R_8)(R_9)$, $N(R_5)_2$,

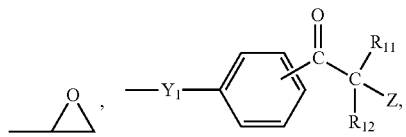 (A)

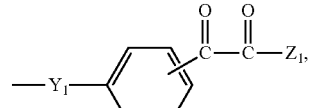 (B)

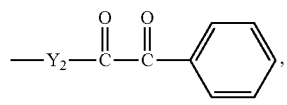 (C)

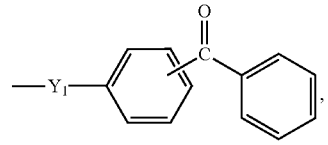 (D)

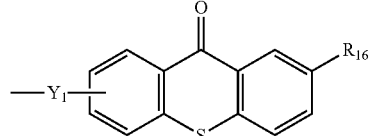 (E)

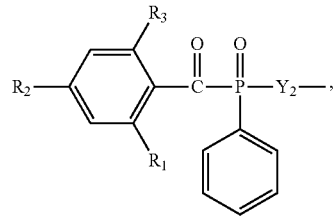 (F)

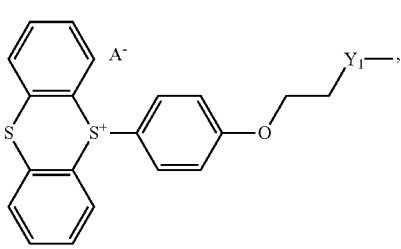 (G)

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH;

or $R_4$, if n is 1, is $C_6$-$C_{10}$aryl which is unsubstituted or substituted by one or more $C_1$-$C_{12}$alkyl, $C_2$-$C_{20}$alkyl which is interrupted by one or more O, $C_1$-$C_{12}$-alkoxy or by OH;

or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;

or $R_4$ if n is 1 is Cl, F or Br, provided that X is a direct bond;

$R_4$, if n=2, is $C_1$-$C_{18}$alkylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl or by naphthyl, $C_2$-$C_{18}$alkylene interrupted by one or more O, $NR_5$, S, (CO), O(CO)O, (NH)(CO)O, O(CO)(NH), O(CO) or (CO)O which interrupted $C_2$-$C_{18}$alkylene is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_2$-$C_{18}$alkenylene which is unsubstituted or substituted by one or more $C_1$-$C_4$alkyl, $C_1$-$C_4$alkoxy or by OH, $C_2$-$C_{18}$alkenylene which is interrupted by one or more O or $NR_5$ which interrupted $C_2$-$C_{18}$alkenylene is unsubstituted or substituted by one or more $C_1$-$C_4$alkyl, $C_1$-$C_4$alkoxy or by OH, $C_5$-$C_8$cycloalkylene which is unsubstituted or substituted by one or more $C_1$-$C_8$alkyl, $C_1$-$C_8$alkoxy, OH, halogen, $C_2$-$C_8$alkenyl, COOR$_6$, $C_1$-$C_{20}$acyl, phenyl, naphthyl or by $C_1$-$C_8$hydroxyalkyl, $C_5$-$C_8$cycloalkylene which is interrupted by one or more O or NR$_5$ which interrupted $C_5$-$C_8$cycloalkylene is unsubstituted or substituted by one or more $C_1$-$C_4$-alkyl, $C_1$-$C_4$alkoxy or by OH, $C_6$-$C_{10}$arylene which is unsubstituted or substituted by one or more $C_1$-$C_8$alkyl, $C_1$-$C_8$-alkoxy, OH, halogen, $C_2$-$C_8$alkenyl, COOR$_6$, $C_1$-$C_{20}$acyl, phenyl, naphthyl or by $C_1$-$C_8$hydroxyalkyl;

or R$_4$, if n=2, is (CO)R$_{10}$(CO); (CO)O—R$_{10}$—O(CO); (CO)NR$_5$—R$_{10}$—NR$_5$(CO), [Si(R$_7$)(R$_8$)]$_p$; [Si(R$_7$)(R$_8$)—O];

or R$_4$, if n=2, is $C_{10}$-$C_{50}$alkylene which is interrupted by one or more groups selected from the group consisting of O, (CO), NR$_5$ and NR$_{17}$, which interrupted $C_{10}$-$C_{50}$alkylene is substituted by one or more OH;

A is PF$_6$, SbF$_6$, AsF$_6$ or B(C$_6$F$_5$)$_4$;

R$_5$ is hydrogen, (CO)R$_6$, phenyl, $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$cycloalkyl, OH or by NCO, $C_3$-$C_{12}$cycloalkyl which is unsubstituted or substituted by one or more $C_1$-$C_4$alkyl, $C_1$-$C_4$alkoxy, OH or by NCO;

R$_6$ is $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$-cycloalkyl, OH, NCO or by phenyl which is substituted by NCO;

or R$_6$ is $C_3$-$C_{12}$cycloalkyl, $C_2$-$C_{10}$alkenyl which is unsubstituted or substituted by one or more $C_1$-$C_4$alkyl, OH or $C_1$-$C_4$alkoxy;

or R$_6$ is $C_6$-$C_{14}$aryl which is unsubstituted or substituted by $C_1$-$C_{12}$alkyl, $C_1$-$C_{12}$alkoxy, NCO or by NCO-substituted $C_1$-$C_{12}$alkyl;

or R$_5$ and R$_6$ together with the N-atom form a 5 or 6-membered saturated ring which is uninterrupted or interrupted by O or NR$_5$ and which uninterrupted or interrupted ring is unsubstituted or substituted by one or more $C_1$-$C_4$alkyl, $C_1$-$C_4$alkoxy or by OH;

R$_7$, R$_8$ and R$_9$ independently of each other are $C_1$-$C_4$alkyl, $C_6$-$C_{14}$aryl or $C_1$-$C_4$alkoxy;

R$_{10}$ is $C_2$-$C_{18}$alkylene, $C_2$-$C_{18}$alkylene which is interrupted by one or more O, NR$_5$ or S, wherein said $C_2$-$C_{18}$alkylene or interrupted $C_2$-$C_{18}$alkylene is unsubstituted or substituted by one or more $C_1$-$C_4$alkyl, $C_1$-$C_4$alkoxy or by OH;

X$_1$ is O or S;

m is 1, 2 or 3;

o is 0-10;

p is 1-10;

Q is an inorganic or organic cation;

Y$_1$ is a bond, O, S, NR$_5$, O(CO)—* or O(CO)—CH$_2$—O—*, wherein the asterix denotes the bond to the phenyl ring of the group (A), (B), (D), or (E);

Y$_2$ is a bond, O, S or NR$_5$;

R$_{11}$ and R$_{12}$ independently of each other are $C_1$-$C_{10}$alkyl, $C_2$-$C_{10}$alkenyl or phenyl-$C_1$-$C_4$-alkyl which is unsubstituted or substituted by $C_1$-$C_4$alkyl, or R$_{11}$ and R$_{12}$ together with the C-atom to which they are attached are cyclohexyl or cyclopentyl;

Z is OH or NR$_{13}$R$_{14}$;

Z$_1$ is $C_1$-$C_{12}$alkoxy or $C_2$-$C_{12}$alkoxy which is interrupted by one or more O, wherein said $C_1$-$C_{12}$alkoxy or interrupted $C_2$-$C_{12}$alkoxy is unsubstituted or substituted by OH;

R$_{13}$ and R$_{14}$ independently of each other are $C_1$-$C_{12}$alkyl, $C_1$-$C_{12}$alkyl which is substituted by one or more OH or halogen; or R$_{13}$ and R$_{14}$ together with the N-atom to which they are attached form a 5- or 6-membered unsaturated or saturated ring, which ring is uninterrupted or interrupted by O or NR$_{15}$;

R$_{15}$ is $C_1$-$C_4$alkyl;

R$_{16}$ is hydrogen or $C_1$-$C_4$alkyl;

R$_{17}$ is (CO)—O—CH$_2$CH$_2$—O(CO)—CH=CH$_2$;

provided that (i) if n is 1, R$_1$, R$_2$ and R$_3$ as $C_1$-$C_4$alkyl are CH$_3$ and X is O, R$_4$ as $C_1$-$C_{28}$alkyl is not methyl, ethyl, n-propyl, 2-propyl, n-butyl, 1-methyl-prop-1-yl, ted-butyl, n-hexyl;

(ii) if n is 1, R$_1$ and R$_3$ as halogen are Cl, R$_2$ is hydrogen and X is O, R$_4$ as substituted $C_6$-$C_{10}$aryl is not 4-butylphenyl;

(iii) if n is 1, R$_1$ and R$_3$ as $C_1$-$C_4$alkoxy are methoxy, R$_2$ is hydrogen and X is NR$_5$, and R$_4$ together with R$_5$ and the N-atom forms a 5 or 6-membered saturated ring, said ring is not piperid-1-yl.

$C_1$-$C_{28}$alkyl is linear or branched and is, for example, $C_1$-$C_{20}$-, $C_1$-$C_{18}$-, $C_1$-$C_{14}$-, $C_1$-$C_{12}$-, $C_1$-$C_{10}$-, $C_1$-$C_8$-, $C_1$-$C_6$- or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl, icosyl, etc. $C_1$-$C_{12}$alkyl, $C_1$-$C_{10}$alkyl, $C_1$-$C_8$alkyl and $C_1$-$C_4$alkyl have the same meanings as given above for $C_1$-$C_{28}$alkyl up to the corresponding number of C-atoms.

$C_1$-$C_8$hydroxyalkyl is $C_1$-$C_8$alkyl as defined above, which is substituted by hydroxyl.

$C_2$-$C_{28}$alkyl which is interrupted by one or more O, NR$_5$ or S is for example interrupted 1-9, 1-7 or once or twice by O, NR$_5$ or S. In case the groups are interrupted by more than one interrupting O atoms, said O-atoms are separated from one another by at least one methylene group, i.e. the O-atoms are non-consecutive. The $C_2$-$C_{28}$alkyl may be interrupted by one or more identical or different interrupting atoms as defined above. The alkyl groups in the interrupted alkyl are linear or branched. Non-limiting examples are the following structural units —CH$_2$—O—CH$_3$, —CH$_2$CH$_2$—O—CH$_2$CH$_3$, —[CH$_2$CH$_2$O]$_y$—CH$_3$, with y=1-9, —(CH$_2$CH$_2$O)$_7$CH$_2$CH$_3$, —CH$_2$—CH(CH$_3$)—O—CH$_2$—CH$_2$CH$_3$, —CH$_2$—CH(CH$_3$)—O—CH$_2$CH$_3$, —CH$_2$—S—CH$_3$, —CH$_2$CH$_2$—S—CH$_2$CH$_3$, —CH$_2$—CH(CH$_3$)—S—CH$_2$—CH$_2$CH$_3$, —CH$_2$—CH(CH$_3$)—S—CH$_2$CH$_3$, —CH$_2$—NR$_5$—CH$_3$, —CH$_2$CH$_2$—NR$_5$—CH$_2$CH$_3$, —[CH$_2$CH$_2$NR$_5$]$_y$—CH$_3$, —(CH$_2$CH$_2$NR$_5$)$_7$CH$_2$CH$_3$, —CH$_2$—CH(CH$_3$)—NR$_5$—CH$_2$—CH$_2$CH$_3$, or —CH$_2$—CH(CH$_3$)—NR$_5$—CH$_2$CH$_3$.

$C_2$-$C_{20}$alkyl which is interrupted by one or more O, and $C_2$-$C_{12}$alkyl which is interrupted by one or more O, are defined as above up to the corresponding number of C-atoms.

$C_2$-$C_{10}$alkenyl radicals are mono or polyunsaturated, linear or branched and are for example $C_2$-$C_8$-, $C_2$-$C_6$- or $C_2$-$C_4$alkenyl. Non-limiting examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl. $C_2$-$C_8$alkenyl is defined as $C_2$-$C_{10}$alkenyl above up to the corresponding number of C-atoms.

$C_3$-$C_{12}$cycloalkyl is for example cyclopropyl, cyclopentyl, cyclohexyl, cyclooctyl, cyclododecyl, especially cyclopentyl and cyclohexyl, preferably cyclohexyl.

$C_3$-$C_{12}$Cycloalkyl in the context of the present application is to be understood as alkyl which at least comprises one ring. For example cyclopropyl, methyl-cyclopentyl, cyclopentyl, cyclohexyl, methyl- or dimethylcyclohexyl, cyclooctyl, especially cyclopentyl and cyclohexyl, preferably cyclohexyl. $C_3$-$C_7$cycloalkyl defined as $C_3$-$C_{1s}$cycloalkyl above up to the corresponding number of C-atoms.

$C_3$-$C_{12}$cycloalkyl which is interrupted by one or more O, $NR_5$ or S has the meanings given above for $C_3$-$C_{12}$Cycloalkyl, wherein at least one $CH_2$-group of the cycloalkyl is exchanged by either O, S or $NR_5$.

Phenyl-$C_1$-$C_4$alkyl is for example benzyl, phenylethyl, α-methylbenzyl, phenylbutyl, phenylpropyl or α,α-dimethylbenzyl, especially benzyl.

$C_1$-$C_8$-alkoxy is linear or branched and is for example $C_1$-$C_6$- or $C_1$-$C_4$-alkoxy. Examples are methoxy, ethoxy, propoxy, isopropoxy, n-butyloxy, sec-butyloxy, iso-butyloxy, tertbutyloxy, pentyloxy, hexyloxy, heptyloxy, 2,4,4-trimethylpentyloxy, 2-ethylhexyloxy, octyloxy, especially methoxy. $C_1$-$C_4$-alkoxy also is linear or branched and has the same meanings as given above up to the corresponding number of C-atoms.

Halogen is fluorine, chlorine, bromine and iodine, especially fluorine, chlorine and bromine, preferably fluorine and chlorine, in particular chlorine.

$C_1$-$C_{20}$acyl is $C_1$-$C_{20}$alkanoyl and is linear or branched and is, for example, $C_1$-$C_{18}$-, $C_1$-$C_{14}$-, $C_1$-$C_{12}$-, $C_1$-$C_8$-, $C_1$-$C_6$- or $C_1$-$C_4$alkanoyl or $C_4$-$C_{12}$- or $C_4$-$C_8$alkanoyl. Examples are formyl, acetyl, propionyl, butanoyl, isobutanoyl, pentanoyl, hexanoyl, heptanoyl, octanoyl, nonanoyl, decanoyl, dodecanoyl, tetradecanoyl, pentadecanoyl, hexadecanoyl, octadecanoyl, icosanoyl, preferably acetyl.

$C_6$-$C_{14}$aryl is for example phenyl, naphthyl, anthryl or phenanthryl, in particular phenyl or naphthyl, preferably phenyl. $C_6$-$C_{10}$aryl has the meanings as given above up to the corresponding number of C-atoms.

Substituted $C_6$-$C_{14}$aryl, $C_6$-$C_{10}$aryl, phenyl or naphthyl is for example substituted one to five times, e.g. once, twice or three times, in particular once or twice at the phenyl ring.

$C_1$-$C_{18}$alkylene is linear or branched alkylene, for example methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene or octadecylene, in particular $C_1$-$C_{12}$alkylene, for example ethylene, decylene,

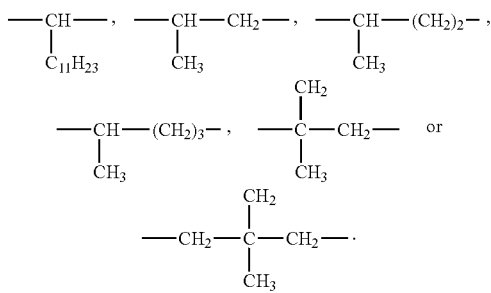

$C_1$-$C_4$alkylen has the definitions as given above up to the corresponding number of C-atoms.

$C_2$-$C_{18}$alkylene interrupted by one or more O, $NR_5$, S, (CO), O(CO)O, (NH)(CO)O, O(CO)(NH), O(CO) or (CO)O is, for example, interrupted 1-9 times, for example 1-7 times or once or twice by O, $NR_5$, S, (CO), O(CO)O, (CO)OCO O, O(CO)(NH), O(CO) or (CO)O. The $C_2$-$C_{18}$alkylene may be interrupted by one or more identical or different interrupting atoms as defined above. The interrupting O-atoms are non-successive. This produces structural units such as, for example, —$CH_2$—O—$CH_2$—, —$CH_2$—S—$CH_2$—, —$CH_2$—N($CH_3$)—$CH_2$—, —$CH_2CH_2$—O(CO)—$CH_2CH_2$—, —[$CH_2CH_2$O]$_y$—, —[$CH_2CH_2$O]$_y$—$CH_2$—, where y=1-9, —($CH_2CH_2$O)$_7CH_2CH_2$—, —$CH_2$—CH($CH_3$)—O—$CH_2$—CH($CH_3$)— or —$CH_2$—CH($CH_3$)—O—$CH_2$—$CH_2CH_2$—, —$CH_2$—(NH)(CO)O—$CH_2$—, etc.

$C_2$-$C_{18}$alkenylene is mono- or polyunsaturated, linear or branched and is, for example, ethenylene, 1-propenylene, 1-butenylene, 3-butenylene, 2-butenylene, 1,3-pentadienylene, 5-hexenylene, 7-octenylene, etc.

$C_2$-$C_{18}$alkenylene which is interrupted by one or more O or $NR_5$ is, for example, interrupted 1-9 times, for example 1-7 times or once or twice by O or $NR_5$, wherein interrupting O-atoms are non-successive and the alkenylene is interrupted by one or more identical or different groups O or $NR_5$.

$C_3$-$C_{12}$cycloalkylene is, for example, cyclopropylene, cyclopentylene, cyclohexylene, cyclooctylene, cyclododecylene, especially cyclopentylene and cyclohexylene, preferably cyclohexylene. $C_5$-$C_8$cycloalkylene has one of the meanings given above up to the corresponding number of C-atoms.

$C_5$-$C_8$cycloalkylene which is interrupted by one or more O or $NR_5$ is, for example, interrupted or once or twice or three times by O or $NR_5$, wherein interrupting O-atoms are nonsuccessive and the cycloalkylene is interrupted by one or more identical or different groups O or $NR_5$.

$C_6$-$C_{10}$arylene is 1,4-, 1,2- or 1,3-phenylene, 1,8-, 1,2-, 2,6-, 1,5-, 1,4-naphthylene, 1,2-, 1,4-, 1,3-, 1,5-, 1,10-, 1,8-, 1,7-, 2,6-, 1,6-, 2,7-anthrylene, etc., 9,10-, 4,5-, 1,2-, 2,3-, 3,6-phenanthrylene, etc.,
in particular 1,4-phenylene.

phenylene-$C_1$-$C_4$alkylene denotes

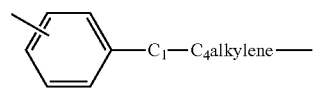

$C_1$-$C_4$alkylene-phenylene-$C_1$-$C_4$alkylene is

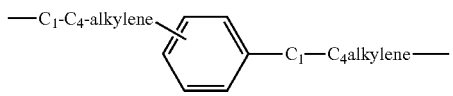

$R_4$ (if n is 1) and X is $NR_5$, together with $R_5$ and the N-atom forming a 5 or 6-membered saturated ring for example structures like

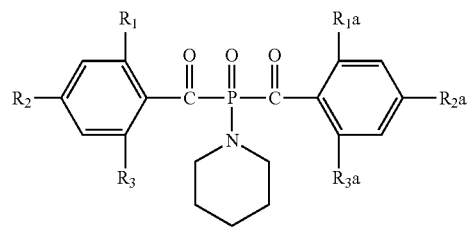

are resulting.

If $R_{11}$ and $R_{12}$ together with the C-atom to which they are attached are cyclohexyl or cyclopentyl structures like

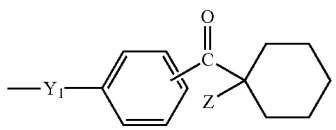

are formed.

If $R_{13}$ and $R_{14}$ together with the N-atom to which they are attached form a 5- or 6-membered unsaturated or saturated ring, which ring is uninterrupted or interrupted by O or $NR_{15}$, saturated or unsaturated rings like for example aziridine, pyrrole, pyrrolidine, oxazole, pyridine, 1,3-diazine, 1,2-diazine, piperidine or morpholine, in particular morpholine are formed.

Q as inorganic or organic cation is for example a monovalent cation, a divalent or trivalent cation; preferably a mono- or divalent cation.

Examples are metals which form oxidation state +1, +2 or +3, such for example alkaline metals, alkaline earth metals, e.g. Li, Na, K, Cs, Mg, Ca, or Cu, Ag, Au, Zn, Au etc.

Further examples for monovalent or divalent cations are "onium" cations, such as an ammonium-, phosphonium-, iodonium- or sulfonium cation.

Onium cations are for example ammonium, tetra-alkylammonium, tri-alkyl-aryl-ammonium, di-alkyl-di-aryl-ammonium, tri-aryl-alkyl-ammonium, tetra-aryl-ammonium, tetraalkylphosphonium, tri-alkyl-aryl-phosphonium, di-alkyl-di-aryl-phosphonium, tri-aryl-alkylphosphonium, tetra-aryl-phosphonium. E.g. $N^+R_{18}R_{19}R_{20}R_{21}$ or $P^+R_{18}R_{19}R_{20}R_{21}$, wherein $R_{18}$, $R_{19}$, $R_{20}$, $R_{21}$ independently of one another are hydrogen, $C_1$-$C_{20}$alkyl, phenyl; $C_1$-$C_{20}$alkyl substituted by OH or phenyl; phenyl substituted by OH or $C_1$-$C_4$ alkyl, or two of $R_{18}$, $R_{19}$, $R_{20}$ and $R_{21}$ form a mono or bicyclic ring structure.

Q, if m is 1 is for example, a metal cation in the oxidation state +1, $N^+R_{18}R_{19}R_{20}R_{21}$ or $P^+R_{18}R_{19}R_{20}R_{21}$, wherein $R_{18}$, $R_{19}$, $R_{20}$, $R_{21}$ are as defined above.

Q is preferably $Li^+$, $Na^+$, $K^+$, $Cs^+$, $N^+R_{18}R_{19}R_{20}R_{21}$ or $P^+R_{18}R_{19}R_{20}R_{21}$; in particular $Li^+$, $Na^+$, $K^+$, $N^+R_{18}R_{19}R_{20}R_{21}$ or $P^+R_{18}R_{19}R_{20}R_{21}$.

Q if m is 2 is for example a metal cation in the oxidation state +2; such as for example $Mg^{2+}$, $Ca^{2+}$, $Zn^{2+}$, $Cu^{2+}$ Q is preferably $Mg^{2+}$, $Ca^{2+}$ or $Cu^{2+}$, or Q represents 2 monovalent groups as defined above.

Examples for Q as $N^+R_{18}R_{19}R_{20}R_{21}$ and two of $R_{18}$, $R_{19}$, $R_{20}$ and $R_{21}$ forming a mono or bicyclic ring structure are

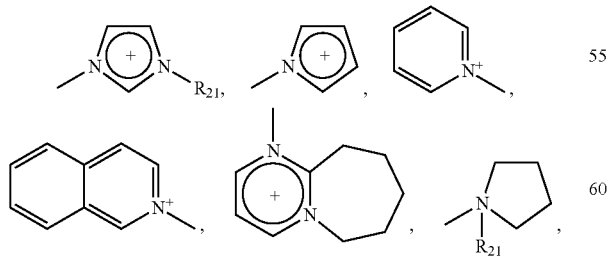

Interesting compounds according to the invention are for example the below-mentioned compounds of examples 1-24, as well as the following compounds (25)-(33)

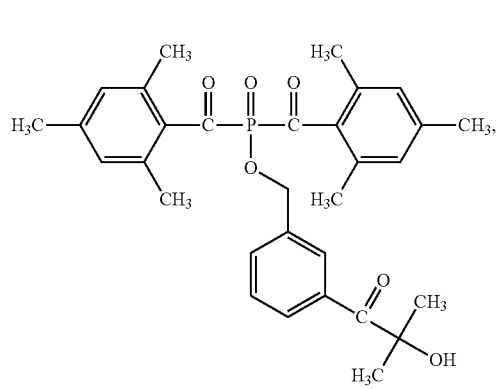

(25)

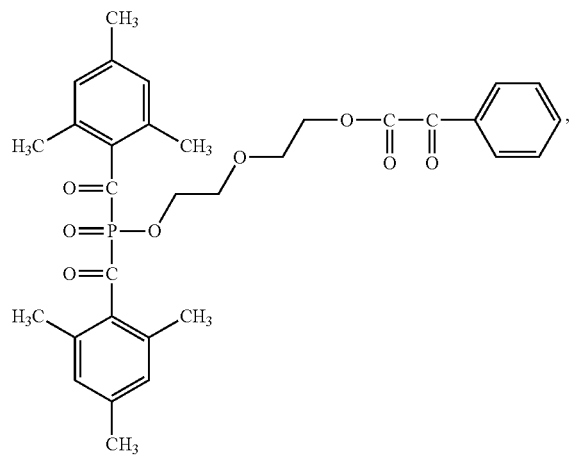

(26)

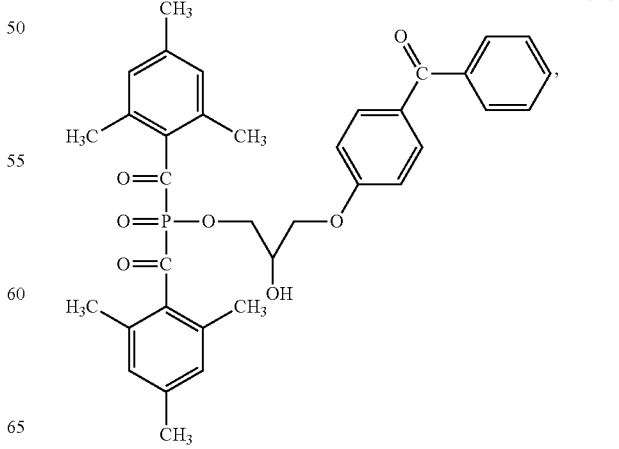

(27)

(28)
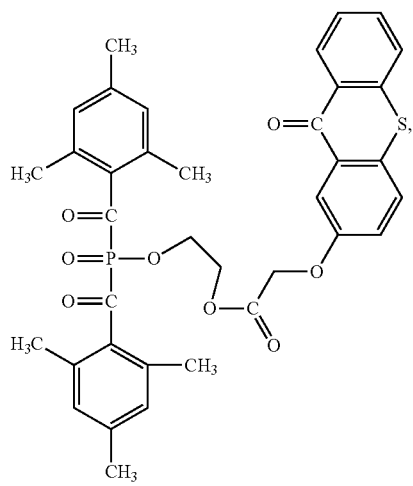

(29)
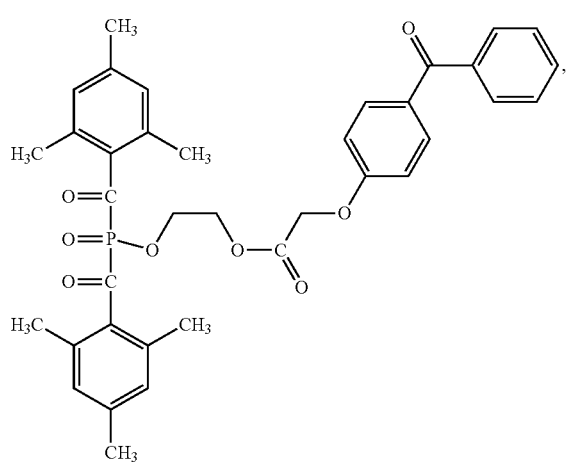

(30)
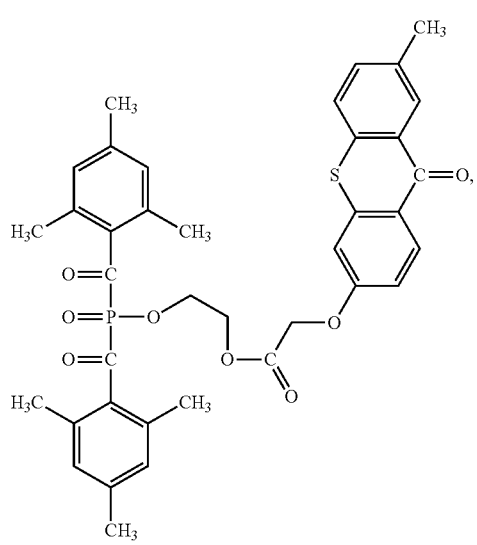

(31)
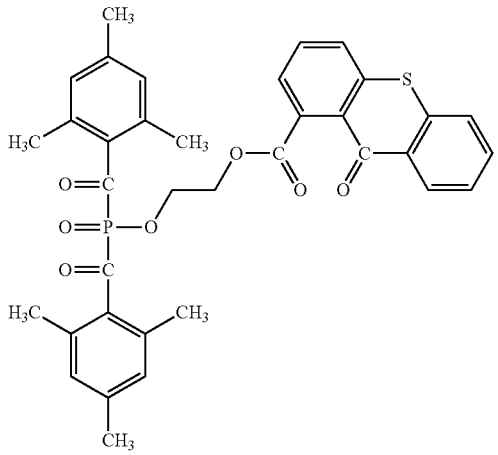

(32)
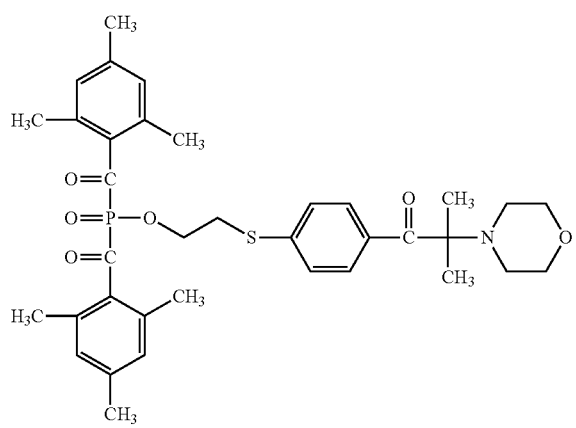

(33)
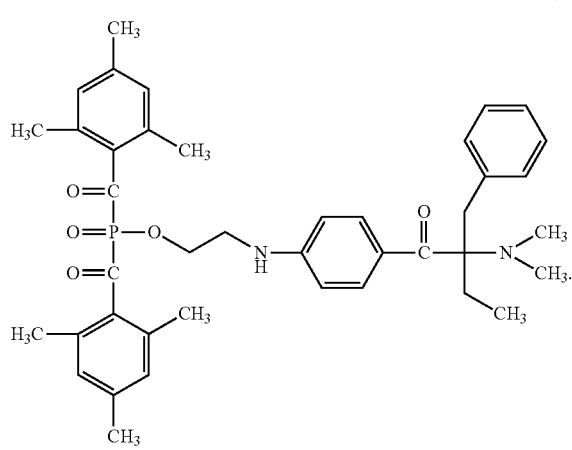

The terms "and/or" or "or/and" in the present context are meant to express that not only one of the defined alternatives (substituents) may be present, but also several of the defined alternatives (substituents) together, namely mixtures of different alternatives (substituents). The term "at least" is meant to define one or more than one, for example one or two or three, preferably one or two. The term "optionally substituted" means, that the radical to which it refers is either unsubstituted or substituted. Throughout this specification and the claims which follow, unless the context requires otherwise, the word "comprise", or variations such as "comprised" or "comprising", will be understood to imply the inclusion of a stated integer or step or group of integers or steps but not the exclusion of any other integer or step or group of integers or steps. The term "(meth) acrylate" in the context of the present application is meant to refer to the acrylate as well as to the corresponding methacrylate. The preferences indicated above for the compounds according to the present invention in the context of this invention are intended to refer to all categories of the claims, that is to the compositions, use, process claims as well.

It is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise. If nothing else is defined, any terms and scientific terminology used herein are intended to have the meanings commonly understood by those of skill in the art to which this invention pertains.

The compounds of the formula (I) and (II) of the present invention can generally be prepared starting from metallized phosphine compounds 1, or phosphides 2, whose preparation is known from the prior art.

The synthesis of sodium bisacylphosphides 1 and phosphides 2 is for example reported in WO2006056541:

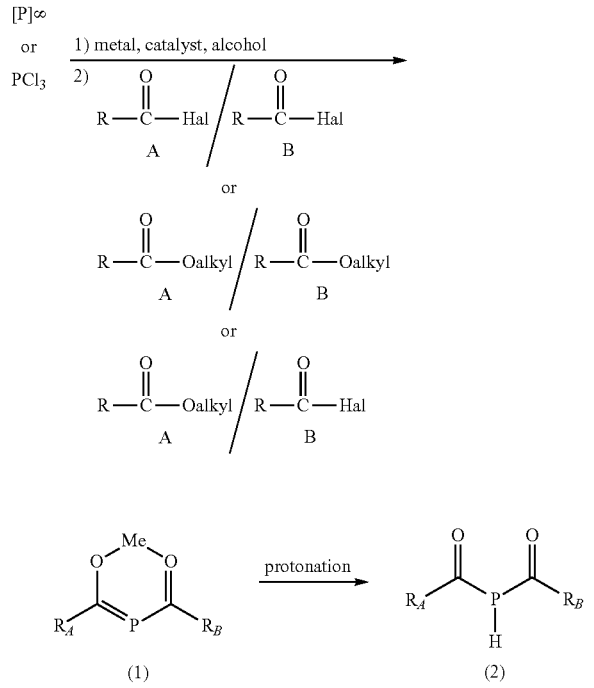

wherein $R_A$ is a group

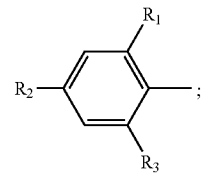

$R_B$ is a group

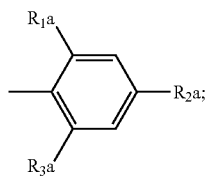

$R_1$, $R_2$, $R_3$, $R_{1a}$, $R_{2a}$, $R_{3a}$ are as defined above; and Me is a monovalent metal.

Depending on the reaction conditions selected, either symmetrically ($R_A=R_B$) or non-symmetrically substituted ($R_A \neq R_B$) compounds 1 or 2 can be obtained.

The sodium bisacylphosphides 1 can either be isolated before the next reaction step or can be directly treated in situ with a reagent suitable for the next reaction step.

Alternatively, the sodium bisacylphosphides 1 can be transformed into the bisacylphosphines 2 by protonation with a suitable proton source. Suitable proton sources are CH-, OH-, SH- or NH-acid compounds or inorganic acids, for example ammonium or amidinium salts, aliphatic or aromatic carboxylic acids, or inorganic acids such as hydrogen chloride, sulfuric acid and the like. Preferred are aliphatic or aromatic carboxylic acids, most preferred aliphatic carbocylic acids such as acetic acid. The protonation is usually performed in solution, using for example aliphatic or aromatic hydrocarbons, (poly)ethers or alcohols as solvents. Preferred are ether derivatives such as e.g dimethoxyethane. The bisacylphosphines 2 can either be isolated by conventional methods known to the skilled person, or it can be used, preferentially after filtration of the salt by-product formed in the protonation reaction, in situ for the next reaction step.

Reaction of 1 or 2 with suitable oxidants or sulfur gives symmetrically or non-symmetrically substituted bisacylphosphinic acid or bisacyl phosphinodithioic acid derivatives 3 (X=O or S):

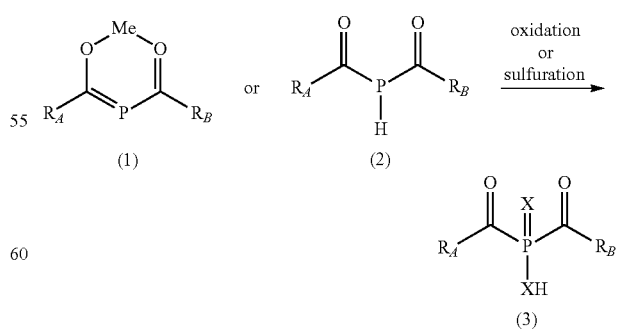

Suitable oxidants are known to the person skilled in the art and include for example air, pure oxygen, hydrogen peroxide, organic peroxides such as tert-butyl peroxide, peracetic acid, etc. The oxidation is usefully carried out in solution. Suitable solvents are aromatic hydrocarbons, such as benzene, toluene, m-xylene, p-xylene, ethylbenzene or mesitylene, or aliphatic hydrocarbons such as alkanes and alkane mixtures, e.g. petroleum ether, hexane or cyclohexane. During oxidation the reaction temperature is preferably kept in the range from 0° C. to 120° C., more preferably from 20° C. to 80° C. The reaction products 3 can be easily isolated and purified by conventional processing methods known to the skilled person. Since compounds 3 are usually solids, recrystallization is preferred.

The reaction with sulfur or sulfurating agents, such as e.g. elemental sulfur or phosphorus sulfides $P_kS_l$, preferentially $P_4S_7$, is preferentially performed in solution. Suitable solvents are aromatic hydrocarbons, such as benzene, toluene, m-xylene, p-xylene, ethylbenzene or mesitylene, or aliphatic hydrocarbons such as alkanes and alkane mixtures, e.g. petroleum ether, hexane or cyclohexane. The reaction temperature is preferably kept in the range from 0° C. to 120° C., more preferably from 20° C. to 80° C. The reaction products 3 can be easily isolated and purified by conventional processing methods known to the skilled person. Since compounds 3 are usually solids, recrystallization is preferred.

The bisacylphosphinic acid or bisacyl phosphinodithioic acid 3 (X═O or S) can be easily transformed into the corresponding bisacylphosphinic acid salts 4 (X═O or S) by the reaction with one equivalent or an excess of a suitable base:

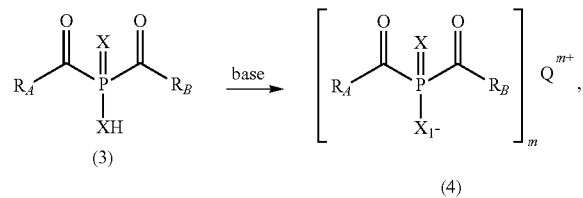

wherein $X_1$, m and Q are as defined above for formula (II).

Further, the salt (4) may directly be obtained by performing the oxidation or sulfuration of compound (2) under basic conditions.

Suitable bases are for example primary, secondary or tertiary alkyl or alkyl aryl amines, amidines, imidazole derivatives etc., e.g

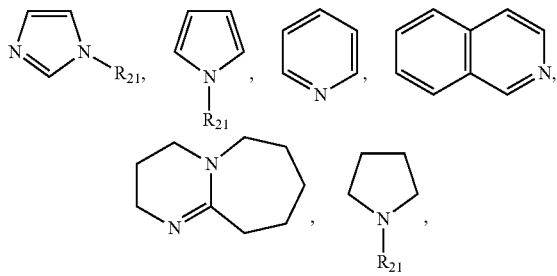

or inorganic bases such as sodium hydroxide, sodium hydrogen carbonate, potassium carbonate and the like. If multibasic bases such as for example potassium carbonate are used, the corresponding salts of bisacylphosphinic acid contain the number of phosphinic acid derivatives required to compensate the charge of the cationic species. The salts obtained can be purified by any of the methods known to the person skilled in the art.

To obtain salts with other cations ($Q_1$), for example metal cations as $Ag^+$, $Cu^{2+}$ or $Au^{3+}$, or N-alkylammonium salts such as

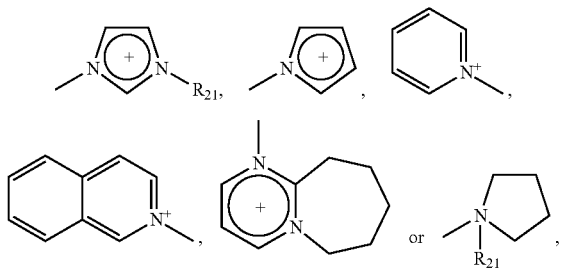

ion exchange reactions from the salt 4 may be performed. The person skilled in the art is familiar with such exchange reactions.

The obtained salt comprising the exchanged cation $Q_1$ can either be prepared and isolated before use, or the ion exchange reaction can be performed in situ in the medium where the final salt is to be used.

It is also possible to prepare metal salts 4 containing metal cations $Q^{m+}$ by mixing the bisacylphosphinic acid or bisacylphosphinodithioic acid 3 (X═O or S) with a corresponding amount of a salt or metal complex salt, as for example $CuSO_4 \cdot 5H_2O$, provided that the anion and/or additional ligands of the metal salt is capable to accept protons.

While compounds of formula 3 and 4 (X═O, S) are useful as photoinitiators as such, they also can serve as versatile intermediates for the synthesis of other bisacylphosphinic acid, bisacyl phosphinodithioic acid, bisacylthiophosphinic acid or bisacylphosphinthioic acid derivatives, with a wider variety of different and functionalized structures as for example

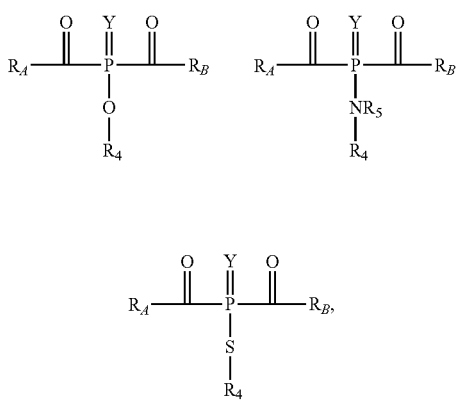

wherein $R_A$, $R_B$, Y, $R_4$ and $R_5$ are as defined above,

Two synthetic protocols for the synthesis of such substituted bisacylphosphinic acid derivatives are available:

a. Reaction of bisacylphosphinic acids 3 or its salts 4 with suitable electrophilic reagents: (equation 2)

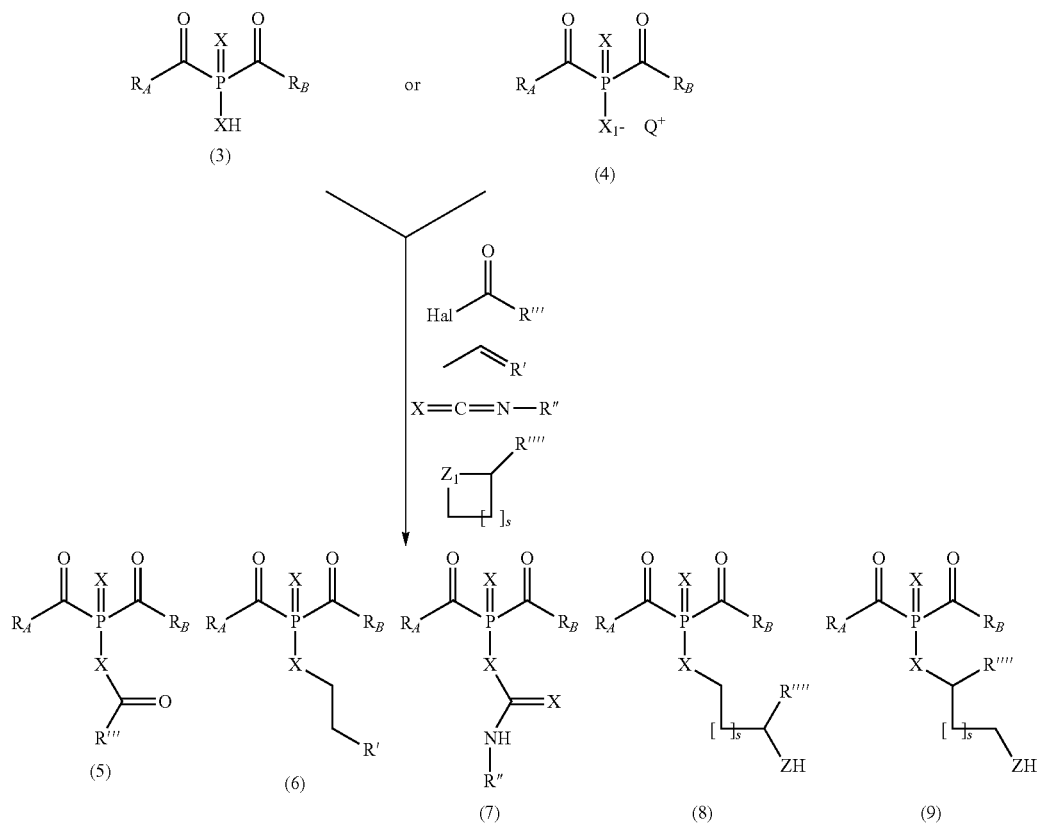

X is O or S, $Z_1$ denotes O or $NR_5$, $R_A$, $R_B$, $R_5$ are as defined above;

R' is $(CO)R_6$, $(CO)OR_6$ or $SO_2$—$R_6$, where $R_6$ is defined as above;

R" is for example $R_6$ as defined above;

R''' is for example $R_6$, $OR_6$, $NR_5R_6$ as defined above; ok

R'''' is for example $C_1$-$C_{26}$alkyl or $C_2$-$C_{26}$alkyl interrupted by one or more O, $NR_5$, S, (CO), (CO)O or $SO_2$, wherein said $C_1$-$C_{26}$alkyl or interrupted $C_2$-$C_{26}$alkyl is unsubstituted or substituted by one or more substituents selected from the group consisting of OH, halide, $C_6$-$C_{14}$aryl, $[Si(R_7)(R_8)]_o$—$Si(R_7)(R_8)(R_9)$, $[Si(R_7)(R_8)$—$O]_o$—$Si(R_7)(R_8)(R_9)$, $N(R_5)_2$,

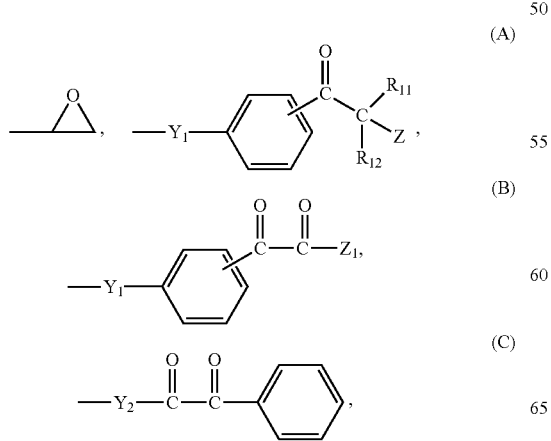

(A)

(B)

(C)

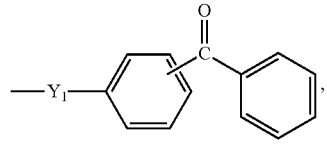

(D)

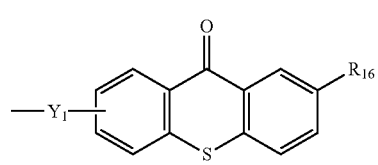

(E)

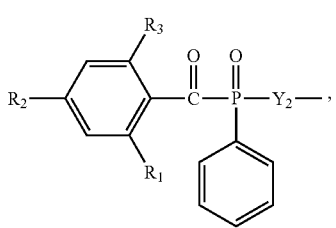

(F)

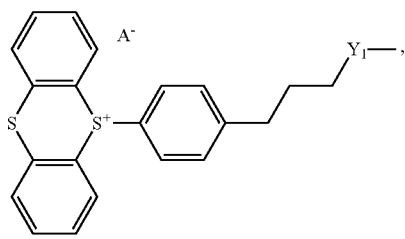
(G)

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH; and s is =0 or 1.

A suitable electrophilic reagent is any reagent capable of reacting with a group OH, SH, O⁻ or S⁻ in a substitution, addition or condensation reaction.

Examples for such suitable electrophilic reagents undergoing a substitution reaction are primary, secondary or tertiary alkyl halides (iodides, bromides or chlorides), benzyl halides or allyl halides, or activated aryl halides such as 2,4-dinitro-bromo benzene and the like. Examples for electrophilic reagents undergoing a condensation reaction are for example aliphatic or aromatic carboxylic acid halides (e.g. such corresponding to the halides of the carboxylic groups as defined above for $R_4$ if n is 1), carboxylic acid esters, carboxylic acid chlorides, carboxylic acid anhydrides, chloroformate esters, dialkyl carbonates, sulfonic acid chlorides. Other reagents undergoing a condensation reaction are for example (alkyl)siloxanes.

Examples for electrophilic reagents undergoing an addition reaction are for example α,β-unsaturated esters, ketones or sulfones (so called Michael acceptors) such as (meth)acrylates or vinyl sulfones. Other reagents undergoing an addition reaction are ring-opening reagents such as cyclic ethers such as epoxides or oxetanes (e.g. such corresponding to the respective groups as defined above for $R_4$ if n is 1), or isocyanate groups. The Michael addition reaction is especially suitable if —XH in the bisacylphosphinic acid 3, or —X⁻ in the bisacylphosphinic acid salts 4 is —SH or —S⁻, respectively.

If the electrophilic reagent is a cyclic ether, preferentially an epoxide, the corresponding reaction products with bisacylphosphinic acid 3 or the bisacylphosphinic acid salts 4 are ring-opening products possessing a hydroxy group on the RO substituent. These hydroxy groups can be further reacted with reagents that can react with alcohol. Examples of such reagents are isocyanate, epoxides, anhydrides, carboxylic acid derivatives and the like. As an example, the reaction with (meth)acrylic acid chloride give co-polymerizable bisacylphosphinic acid derivatives possessing a (meth)acrylate group in the molecule.

When the electrophilic reagent is an (alkyl)siloxane, bisacylphosphinic acid silyl esters are obtained. If (bisalkoxy) silanes are used as electrophilic agent in a molar ratio of 2:1, difunctional bisacylphosphinic acid silyl esters are obtained. Depending on the size of the siloxane moiety, it is easily possible to tune for example surface active properties of the photoinitiator obtained. It is obvious to the person skilled in the art that fine tuning of such properties is of outmost interest, for example for the preparation of self-stratifying photoinitiators that accumulate at the resin interface.

Under some conditions it may be advantageous to perform the substitution, addition or condensation reactions in the presence of a suitable catalyst or suitable co-reagent. A catalyst for a substitution reaction with a primary alkyl, benzyl or allyl chloride or bromide is an iodine salt, such as sodium iodide, potassium iodide or an ammonium iodide. A suitable co-reagent for a substitution reaction with a tertiary alkyl halide is silver nitrate. The latter reagent has to be used in stoichiometric amounts. If —X—$R_4$ is —OH or —SH, addition of a suitable base in catalytic or stoichiometric amounts may be advantageous. Suitable bases are for example inorganic alkali or earth alkali hydroxides, tertiary amines, or amidinium bases such as 1,5-Diazabicyclo(4.3.0) non-5-en (DBN), 1,8-Diazabicyclo[5.4.0]undec-7-ene (DBU) or guanidine.

If the electrophilic reagent is a Michael acceptor or a ring-opening reagent, tertiary amines or amidinium bases such as DBN, DBU or guanidine or trialkyl phosphines are useful to accelerate the addition reaction. These reagents can be used in catalytic or stoichiometric amounts.

If the electrophilic reagent undergoing a condensation reaction is a carboxylic acid, a carboxylic acid chloride, a carboxylic acid anhydride, or a chloroformate esters, addition of a base may be advantageous. Suitable bases are for example inorganic alkali or earth alkali hydroxides, tertiary amines, or amidinium bases such as DBN, DBU or guanidine. These bases are usually added in stoichiometric amounts. The condensation reaction may also be accelerated by the addition of a condensation agent such as dicyclohexyl carbodiimine or a catalyst such as 4-diemtahlyamino pyridine.

If the electrophilic reagent undergoing a condensation reaction is an isocyanate, any catalyst for urethane condensations known to the person skilled in the art can be used. These include for example organometallic compounds such as dibutyltin dilaurate or bases such as 1,4-Diazabicyclo[2.2.2]octan (DABCO). Suitable catalysts are known to the person skilled in the art and are subject in many textbooks of Chemistry.

If the electrophilic reagent undergoing a condensation reaction is a carboxylic acid ester, it may be advantageous to perform the condensation reaction under conditions where the liberated alcohol is removed from the reaction mixture, for example by distillation, possibly under vacuum, or by using a suitable two-phase system.

Since the substitution, addition or condensation reaction can be performed under mild conditions, a wider variety of functional groups are tolerated as part of the residue R"-R"". Examples are epoxy groups or isocyanate groups. The latter provide a functionality in compounds (5)-(9) that can be used for further transformations. Examples are the ring-opening reaction of an epoxide by (meth)acrylic acid or the reaction (meth)acrylic acid 2-hydroxyethyl ester with an isocyanate group, providing co-polymerizable bisacylphosphinic acid derivative photoinitiators. If the additional transformation steps are performed with suitable difunctional regents used in a molar ratio of 1:2 to the compound (5)-(9), the corresponding difunctional bisacylphosphinic acid derivatives, wherein n is 2, can be obtained. A suitable difunctional reagent is for example the diisocyanate Laromer 9000) providing low-migrating photoinitiator structures.

b. Substitution of the XH or X⁻ (X═O, S) of bisacylphosphinic acids 3 by suitable leaving groups (LG), possibly followed by exchange of the leaving group by a suitable nucleophilic reagent: (equation 3)

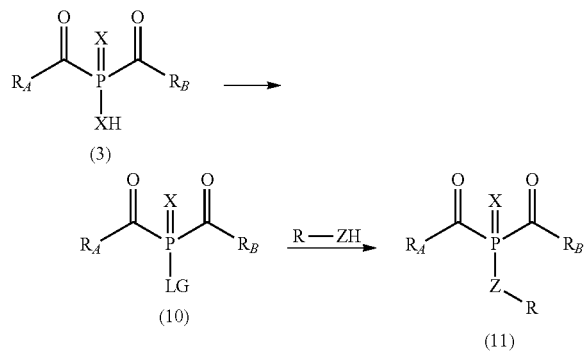

wherein X is O or S; Z is O, S or NR$_5$.

Various processes for the transformation of a group XH into a leaving group LG are known to the person skilled in the art. These include for example reaction of compounds of structure 3 with phosgene, thionyl chloride, sulfuryl chloride, phosphortrichloride, phosphoroxytrichloride, phosphorpentachloride, oxalylchloride, hydrogen chloride, chlorine or N-chlorocompounds such as N-chlorosuccinimide providing compounds 5 with LG=Cl; alkali fluorides, cobalt fluoride, halogene fluorides, antimony fluoride, molybdenium fluoride, hydrogen fluoride, fluorine or sulfur tetrafluoride providing compounds 5 with LG=F; iodine, iodine monochloride, phosphortriiodide, N-iodosuccinimide or N-iodoacetimide providing compounds 5 with LG=I; chlorcyan, cyanurchloride. Preferred are thionyl chloride, sulfuryl chloride and oxalylchloride.

Other suitable intermediates of structure (10) are for example mixed anhydrides between the bisacylphosphinic acid (3) and a suitable carboxylic acid. Such compounds can for example be prepared by the reaction of a bisacylphosphinic acid (3) with a carboxylic acid anhydride, such as for example acetic acid anhydride.

The leaving group LG in compound 10 can easily be exchanged by a proton-active compound R—ZH or a corresponding salt R—Z$^-$ cation$^+$. Suitable proton-active compounds are for example aliphatic or aromatic alcohols, aliphatic or aromatic primary or secondary amines, or aliphatic or aromatic thiols.

In certain cases it may be useful to perform the exchange reaction in the presence of a catalyst or a suitable reaction aid. Typical catalysts are for example tertiary amines such as triethylamine, the Hünig base and the like. These compounds are usually added in small (catalytic) amounts. Suitable reaction aids are for example silver nitrate (if LG=halogen). These compounds are added in stoichiometric amounts.

Compounds of structure (10) can be isolated and possibly purified by methods known to those skilled in the art. In many cases, however, it may be more convenient not to isolate the compounds of structure (10) but reacted them in situ with a suitable nucleophilic reagent. In some cases it is even not possible to isolate the compounds of structure (10). Specifically this is the case if compounds of structure (10) are produced in situ in only small quantities by a reagent that may be used in catalytic amounts. A typical example is the transesterification of bisacylphosphinic acids 3, e.g. with an alcohol in the presence of a suitable catalyst, such as a Lewis or Brö nsted acid. Typical examples for such catalysts are carboxylic acids such as acetic acid or trifluoroacetic acid, sulfonic acid derivative such as para-toluene sulfonic acid, inorganic acids such as hydrogen chloride, or metal catalysts such as zirconium acetoacetate, dibutyl tin dilaurate and the like. Other reaction aids that are used in stoichiometric amounts without isolating the intermediate compound (10) are for example condensation agents such as dicyclohexylcarbodiimide (DCC).

Depending on the size and structure of the substituent R, bisacylphosphinic acid derivatives possessing a wide variety of desirable properties can be achieved. As an example, if R—ZH is ethanol or, a solid crystalline material is obtained. If R—ZH is a higher alcohol such as for example nonanol, liquid compounds with an excellent compatibility in non-polar media are obtained. If R—ZH is a polyethylenglycol monoalkyl ether, liquid compounds with a good compatibility with both non-polar and polar medium such as waterborne formulations, are obtained. Especially the combination of the compatibility of the photoinitiator compound with non-polar (e.g. organic formulation) and polar media (e.g. water-borne formulations) is a highly required property. It is obvious to the person skilled in the art that such a fine tuning of application properties is of high value for many applications.

Since the exchange reaction can be performed under mild conditions, a wider variety of functional groups are tolerated as part of the residue R. Examples are suitable (meth) acryloxy-substituted compounds R—ZH, such as for example hydroxyethyl (meth)acrylate. The introduction of a (meth)acryl group via the exchange reaction results in copolymerizable bisacylphosphinic acid derivatives.

If difunctional proton-active groups of the general structure HZ—R'—ZH are used in a molar ratio of 1:2 to the compound 10, the corresponding difunctional bisacylphosphinic acid derivatives, wherein n is 2, can be obtained. If difunctional proton-active groups of the general structure HZ—R'—ZH are used in a molar excess (1:1 molar ratio), monofunctional bisacylphosphinic acid derivatives possessing a —ZH functional group on the substituent R are obtained. Further reactions of the —ZH group on the substituent R are possible. For example, it is possible to react the —ZH group with an isocyanate or a carboxylic acid derivative.

If X in 3 is oxygen, the substitution of LG in 4 by a thiol reagent or hydrogen sulfide (R—ZH, Z=S) gives bisacylphosphinic acid thioacid or thioesters. If X in 3 is sulfur, bisacylthiophosphinic acid or esters are obtained by the substitution of LG in 4 by an alcohol reagent or water (R—ZH, Z=O). If X in 3 is sulfur, the substitution of LG in 4 by a thiol reagent or hydrogen sulfide (R—ZH, Z=S), bisacylthiophosphinic thioacid or thioesters are obtained. Thus the synthetic protocol as reported by equation 3 gives an easy access to the whole palette of bisacylphosphinic acid, bisacylthiophosphinic acid, bisacylphosphinic thioacid, and bisacylthiophosphinic thioacid derivatives.

If X in 3 is oxygen or sulfur, the substitution of LG in 4 by an amine reagent or ammonia (RR'—ZH, Z=N) gives bisacylphosphinic acid amides or bisacylthiophosphinic amides.

If the residue R in R—ZH contains a photoinitiating functionality, for example a group (A), (B), (C), (D), (E) (F) or (G) as defined above or a second bisacyalphosphinic acid derivative as in structure (I) with n=2, bifunctional photoinitiator structures are obtained by the exchange reaction. The photoinitiating functionality can in turn be a bisacylphosphinic acid derivative, or it can be any other known photoinitiating structure. Such photoinitiating structurs are known to the person skilled in the art and are for example α-hydroxyketone photoinitiators, α-aminoketone photoinitiators, phenylglyoxylate photoinitiators, monoacylphosphine oxide photoinitiators, bisacylalkylphosphine oxide photoinitiators, benzophenone-type photoinitiators, or thioxanthone-type photoinitiators. Alternatively the photoinitiator moiety of R can be of another type than a radical photoinitiator. Examples are cationic photoinitiator moieties such as sulfonium or iodonium salts, photoacid generator (PAG) groups such as oxime sulfonates, or photolatent bases (PLB) such N-benzyl 1,5-diazabicyclo[4.3.0]nonan derivatives.

The combination of a bisacylphospinic acid moiety with a second radical photoinitiator moiety, or with another type of photoinitiator is interesting in combining the properties of two different photoactive moieties in one molecule.

Subject of the invention accordingly also is a process for the preparation of compounds of formula (I) or (II),

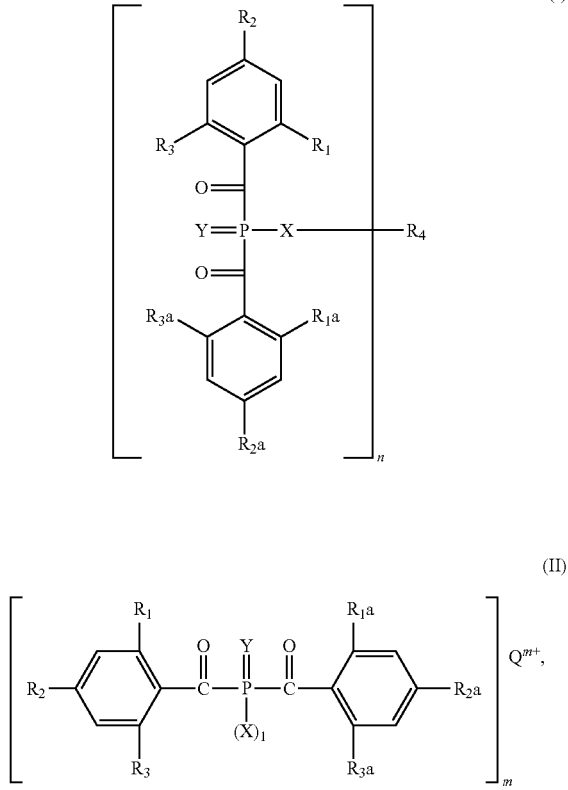

(I)

(II)

wherein $X$, $X_1$ and $Y$ are identical and are O or S;

$R_4$ is hydrogen;

$R_1$, $R_2$, $R_3$, $R_{1a}$, $R_{2a}$ and $R_{3a}$ independently of each other are $C_1$-$C_4$alkyl, $C_1$-$C_4$alkoxy or halogen;

n is 1 or 2;

m is 1, 2 or 3;

Q represents one or two inorganic or organic cations with a charge of m*;

by a1) reacting a metallized phosphine complex of the formula (X) or a phosphine of the formula (XI)

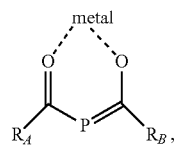

(X)

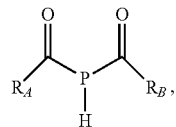

(XI)

wherein $R_A$ is a group

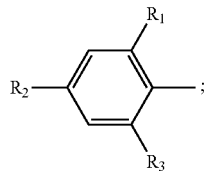

;

$R_B$ is a group

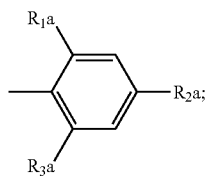

and $R_1$, $R_2$, $R_3$, $R_{1a}$, $R_{2a}$ and $R_{3a}$ are as defined above;

with an oxidation agent, to obtain a compound of formula (I), wherein $R_4$ is hydrogen and X and Y are O;

or a2) reacting a metallized phosphine complex of the formula (X) or a phosphine of the formula (XI) as defined above, with a sulfuration agent to obtain compounds of formula (I), wherein $R_4$ is hydrogen and X and Y are S;

or a3) reacting a metallized phosphine complex of the formula (X) or a phosphine of the formula (XI) as defined above, with an oxidation agent, in the presence of a base, to obtain compounds of formula (I), wherein X and Y are O;

or a4) reacting a metallized phosphine complex of the formula (X) or a phosphine of the formula (XI) as defined above, with a sulfuration agent in the presence of a base to obtain compounds of formula (II), wherein X and Y are S.

Another subject of the invention is a process for the preparation of bisacylphosphinic acid compounds and bisacylthiophosphinic acid compounds of formula (I)

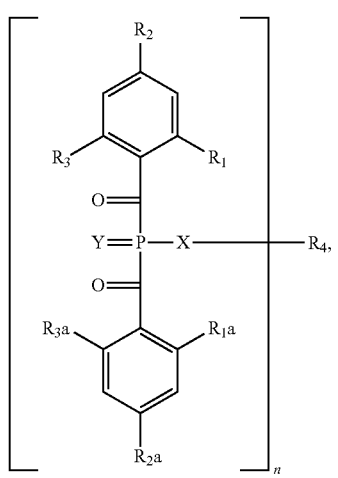

(I)

wherein
Y is O or S;
X is a direct bond;
$R_4$ is halogen; and
$R_1$, $R_2$, $R_3$, $R_1a$, $R_2a$, $R_3a$ and n are as defined above;
by reacting a compound
of formula (I), wherein $R_4$ is hydrogen and X and Y are O, or
of formula (I), wherein $R_4$ is hydrogen and X and Y are S, or
of formula (II), wherein $X_1$ and Y are O, or
of formula (II), wherein $X_1$ and Y are S,
with a halogenating agent to obtain a compound

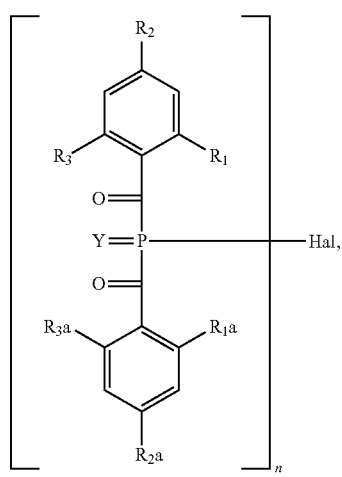

(Ia)

wherein n, $R_1$, $R_2$, $R_3$, $R_1a$, $R_2a$, $R_3a$ and Y are as defined above and Hal is Cl, Br or I, preferably Cl.

A further subject of the invention is a process for the preparation of compounds of the formula (I) or (II)

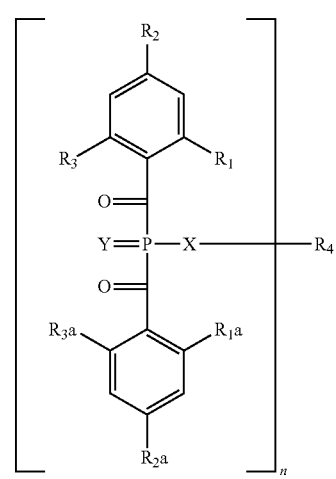

(I)

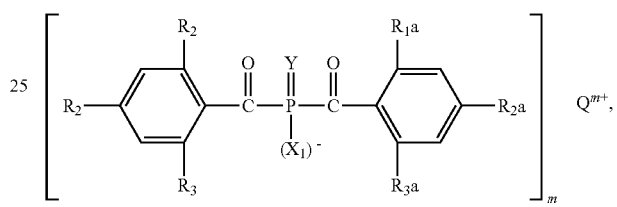

(II)

wherein
$R_1$, $R_2$, $R_3$, $R_{1a}$, $R_{2a}$, $R_{3a}$, Q and Y are as defined above;
X is O or S;
$X_1$ is O or S;
$R_4$, if n is 1, is $(CO)R_6$, $(CO)OR_6$, $(CO)NR_5R_6$, $(SO_2)$—$R_6$, $[Si(R_7)(R_8)]_o$—$Si(R_7)(R_8)(R_9)$, $[Si(R_7)(R_8)$—$O]_o$—$Si(R_7)(R_8)(R_9)$, $C_1$-$C_{28}$alkyl, $C_2$-$C_{28}$alkyl which is interrupted by one or more O, $NR_5$, S, (CO), (CO)O, or $SO_2$; wherein said $C_1$-$C_{28}$alkyl or interrupted $C_2$-$C_{28}$alkyl is unsubstituted or substituted by one or more substituents selected from the group consisting of OH, halide, $C_6$-$C_{14}$aryl, $[Si(R_7)(R_8)]_o$—$Si(R_7)(R_8)(R_9)$, $[Si(R_7)(R_8)$—$O]_o$—$Si(R_7)(R_8)(R_9)$, $N(R_5)_2$,

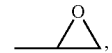

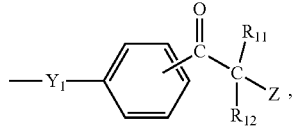

(A)

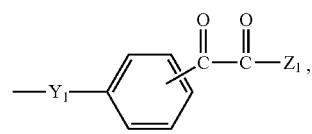

(B)

(C)

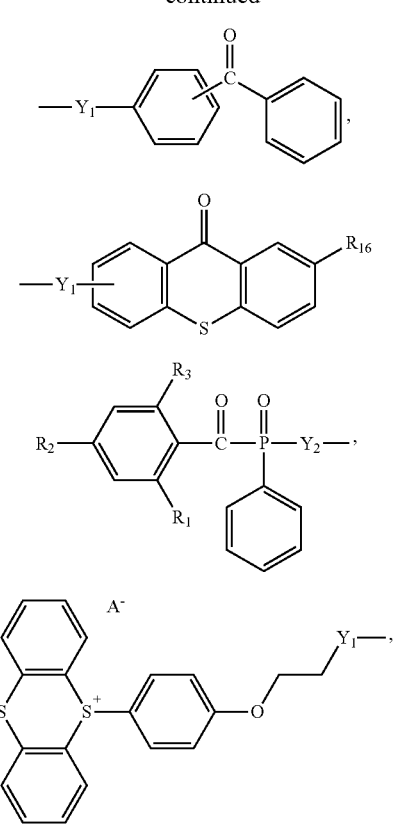

(D), (E), (F), (G)

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH;

or $R_4$, if n is 1, is $C_6$-$C_{10}$aryl which is unsubstituted or substituted by one or more $C_1$-$C_{12}$alkyl, $C_2$-$C_{20}$alkyl which is interrupted by one or more O, $C_1$-$C_{12}$-alkoxy or by OH;

or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by $C_1$-$C_4$alkyl, $C_1$-$C_4$alkoxy or by OH;

or $R_4$ if n is 1 is Cl, F or Br, provided that X is a direct bond;

$R_4$, if n=2, is $C_1$-$C_{18}$alkylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl or by naphthyl, $C_2$-$C_{18}$alkylene interrupted by one or more O, $NR_5$, S, (CO), O(CO)O, (NH)(CO)O, O(CO)(NH), O(CO) or (CO)O which interrupted $C_2$-$C_{18}$alkylene is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_2$-$C_{18}$alkenylene which is unsubstituted or substituted by one or more $C_1$-$C_4$alkyl, $C_1$-$C_4$alkoxy or by OH, $C_2$-$C_{18}$alkenylene which is interrupted by one or more O or $NR_5$ which interrupted $C_2$-$C_{18}$alkenylene is unsubstituted or substituted by one or more $C_1$-$C_4$alkyl, $C_1$-$C_4$alkoxy or by OH, $C_5$-$C_8$cycloalkylene which is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_5$-$C_8$cycloalkylene which is interrupted by one or more O or $NR_5$ which interrupted $C_5$-$C_8$cycloalkylene is unsubstituted or substituted by one or more $C_1$-$C_4$-alkyl, $C_1$-$C_4$alkoxy or by OH, $C_6$-$C_{10}$arylene which is unsubstituted or substituted by one or more $C_1$-$C_8$alkyl, $C_1$-$C_8$-alkoxy, OH, halogen, $C_2$-$C_6$alkenyl, $COOR_6$, $C_1$-$C_{20}$acyl, phenyl, naphthyl or by $C_1$-$C_8$hydroxyalkyl;

or $R_4$, if n=2, is $(CO)R_{10}(CO)$; $(CO)O$—$R_{10}$—$O(CO)$; $(CO)NR_5$—$R_{10}$—$NR_5(CO)$, $[Si(R_7)(R_8)]_p$; $[Si(R_7)(R_8)$—$O]_p$;

or $R_4$, if n=2, is $C_{10}$-$C_{50}$alkylene which is interrupted by one or more groups selected from the group consisting of O, (CO), $NR_5$ and $NR_{17}$, which interrupted $C_{10}$-$C_{50}$alkylene is substituted by one or more OH;

A is $PF_6$, $SbF_6$, $AsF_6$ or $B(C_6F_5)_4$;

$R_5$ is hydrogen, $(CO)R_6$, phenyl, $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$cycloalkyl, OH or by NCO, $C_3$-$C_{12}$cycloalkyl which is unsubstituted or substituted by one or more $C_1$-$C_4$alkyl, $C_1$-$C_4$alkoxy, OH or by NCO;

$R_6$ is $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$-cycloalkyl, OH, NCO or by phenyl which is substituted by NCO;

or $R_6$ is $C_3$-$C_{12}$cycloalkyl, $C_2$-$C_{10}$alkenyl which is unsubstituted or substituted by one or more $C_1$-$C_4$alkyl, OH or $C_1$-$C_4$alkoxy;

or $R_6$ is $C_6$-$C_{14}$aryl which is unsubstituted or substituted by $C_1$-$C_{12}$alkyl, $C_1$-$C_{12}$alkoxy, NCO or by NCO-substituted $C_1$-$C_{12}$alkyl;

or $R_5$ and $R_6$ together with the N-atom form a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;

$R_7$, $R_8$ and $R_9$ independently of each other are $C_1$-$C_4$alkyl, $C_6$-$C_{14}$aryl or $C_1$-$C_4$alkoxy;

$R_{10}$ is $C_2$-$C_{18}$alkylene, $C_2$-$C_{18}$alkylene which is interrupted by one or more O, $NR_5$ or S, wherein said $C_2$-$C_{18}$alkylene or interrupted $C_2$-$C_{18}$alkylene is unsubstituted or substituted by one or more $C_1$-$C_4$alkyl, $C_1$-$C_4$alkoxy or by OH;

m is 1, 2 or 3;

o is 0-10;

p is 1-10;

$Y_1$ is a bond, O, S, $NR_5$, O(CO)—* or O(CO)—$CH_2$—O—*, wherein the asterix denotes the bond to the phenyl ring of the group (A), (B), (D), or (E);

$Y_2$ is a bond, O, S or $NR_5$;

$R_{11}$ and $R_{12}$ independently of each other are $C_1$-$C_{10}$alkyl, $C_2$-$C_{10}$alkenyl or phenyl-$C_1$-$C_4$-alkyl which is unsubstituted or substituted by $C_1$-$C_4$alkyl, or $R_{11}$ and $R_{12}$ together with the C-atom to which they are attached are cyclohexyl or cyclopentyl;

Z is OH or $NR_{13}R_{14}$;

$Z_1$ is $C_1$-$C_{12}$alkoxy or $C_2$-$C_{12}$alkoxy which is interrupted by one or more O, wherein said $C_1$-$C_{12}$alkoxy or interrupted $C_2$-$C_{12}$alkoxy is unsubstituted or substituted by OH;

$R_{13}$ and $R_{14}$ independently of each other are $C_1$-$C_{12}$alkyl, $C_1$-$C_{12}$alkyl which is substituted by one or more OH or halogen; or $R_{13}$ and $R_{14}$ together with the N-atom to which they are attached form a 5- or 6-membered unsaturated or saturated ring, which ring is uninterrupted or interrupted by O or $NR_{15}$;

$R_{15}$ is $C_1$-$C_4$alkyl;

$R_{16}$ is hydrogen or $C_1$-$C_4$alkyl;

$R_{17}$ is (CO)—O—$CH_2CH_2$—O(CO)—CH=$CH_2$;

by reacting a compound
 of formula (I), wherein $R_4$ is hydrogen and X and Y are O, or
 of formula (I), wherein $R_4$ is hydrogen and X and Y are S, or
 of formula (II), wherein $X_1$ and Y are O, or
 of formula (II), wherein $X_1$ and Y are S,
with a suitable electrophilic reagent.

Subject of the invention further is a process for the preparation of compounds of the formula (I) or (II), as defined above, wherein
 $R_1$, $R_2$, $R_3$, $R_{1a}$, $R_{2a}$, $R_{3a}$, Q and Y are as defined above;
 X is O or S or $NR_5$;
 $R_4$ has one of the definitions as previously given;
by reacting a compound of the formula (Ia) as defined above with a suitable nucleophilic reagent.

The preparation of the phosphine metal complex compounds (X) is known from the prior art and e.g. described in WO 2006/056542.

The compounds

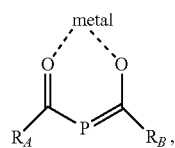
(X)

wherein $R_A$ and $R_B$ are as defined above, are for example prepared by
(i) contacting elemental phosphorus $[P]_\infty$ or preferably $P(Hal)_3$ with a reducing metal or metalloid, optionally in the presence of a catalyst or an activator, in a solvent to obtain metal phosphides $Me_vP_w$; where for example v is 1-6 and w is 1-16;
(ii) adding a proton source, for example a sterically hindered alcohol, optionally in the presence of a catalyst or an activator, to obtain metal or metalloid dihydrogen phosphides $MePH_2$;
(iii) subsequent reaction with z acid halides of formula (XX), or/and (XX') or/and (2-z) carboxylic acid esters of formula (XXI) or/and (XXI')

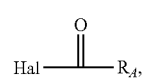
(XX)

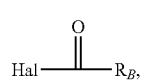
(XX')

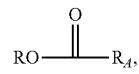
(XXI)

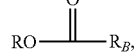
(XXI')

wherein R is the residue of an alcohol and $R_A$ and $R_B$ are as defined above, and z is 0, 1 or 2.

The compounds of formula (XI)

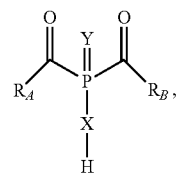
(XI)

are for example obtained from reacting the compounds of formula (X) with a proton source followed by oixidation or sulfuration of the resulting hydride

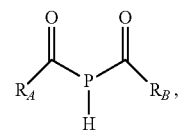

Accordingly, subject of the invention also is a process for the preparation of compounds of the formula (I) or (II), wherein
 X, $X_1$ and Y are identical and are O or S;
 $R_4$ is $(CO)R_6$, $(CO)OR_6$, $(CO)NR_5R_6$, $(SO_2)$—$R_6$, $[Si(R_7)(R_8)]_o$—$Si(R_7)(R_8)(R_9)$, $[Si(R_7)(R_8)$—$O]_o$—$Si(R_7)(R_8)(R_9)$, $C_1$-$C_{28}$alkyl, $C_2$-$C_{28}$alkyl which is interrupted by one or more O, $NR_5$, S, (CO), (CO)O, or $SO_2$; wherein said $C_1$-$C_{28}$alkyl or interrupted $C_2$-$C_{28}$alkyl is unsubstituted or substituted by one or more substituents selected from the group consisting of
 OH, halide, $C_6$-$C_{14}$aryl, $[Si(R_7)(R_8)]_o$—$Si(R_7)(R_8)(R_9)$, $[Si(R_7)(R_8)$—$O]_o$—$Si(R_7)(R_8)(R_9)$, $N(R_5)_2$,

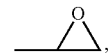
(A)

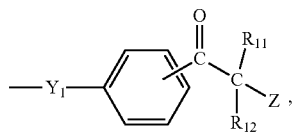
(B)

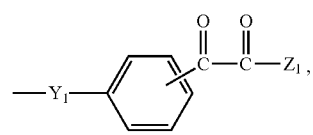
(C)

-continued

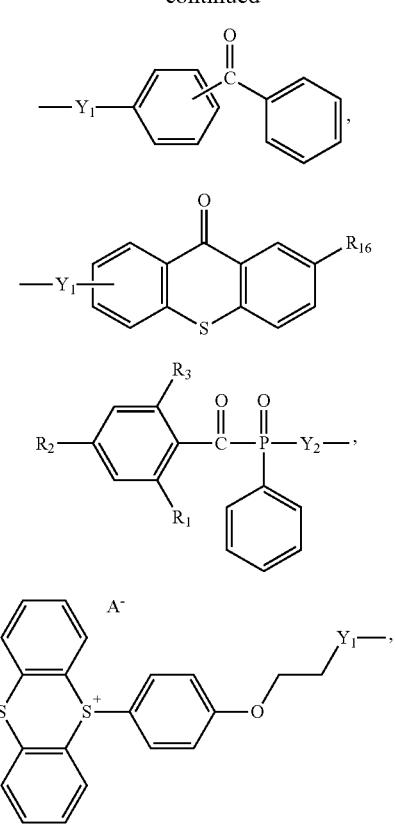

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH,
and $C_6$-$C_{14}$aryl which is unsubstituted or substituted by $C_1$-$C_4$alkyl, $C_1$-$C_4$alkoxy or by OH;
or $R_4$, if n is 1, is $C_6$-$C_{10}$aryl which is unsubstituted or substituted by one or more $C_1$-$C_{12}$alkyl, $C_2$-$C_{20}$alkyl which is interrupted by one or more O, $C_1$-$C_{12}$-alkoxy or by OH;
or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH,
or $R_4$ if n is 1 is Cl, F or Br, provided that X is a direct bond;
$R_4$, if n=2, is
$C_1$-$C_{18}$alkylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl or by naphthyl, $C_2$-$C_{18}$alkylene interrupted by one or more O, $NR_5$, S, (CO), O(CO)O, (NH)(CO)O, O(CO)(NH), O(CO) or (CO)O which interrupted $C_2$-$C_{18}$alkylene is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl,
$C_2$-$C_{18}$alkenylene which is unsubstituted or substituted by one or more $C_1$-$C_4$alkyl, $C_1$-$C_4$alkoxy or by OH, $C_2$-$C_{18}$alkenylene which is interrupted by one or more O or $NR_5$ which interrupted $C_2$-$C_{18}$alkenylene is unsubstituted or substituted by one or more $C_1$-$C_4$alkyl, $C_1$-$C_4$alkoxy or by OH,
$C_5$-$C_8$cycloalkylene which is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_5$-$C_8$cycloalkylene which is interrupted by one or more O or $NR_5$ which interrupted $C_5$-$C_8$cycloalkylene is unsubstituted or substituted by one or more $C_1$-$C_4$-alkyl, $C_1$-$C_4$alkoxy or by OH,
$C_6$-$C_{10}$arylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl, naphthyl or by $C_1$-$C_8$hydroxyalkyl;
or $R_4$, if n=2, is (CO)$R_{10}$(CO); (CO)O—$R_{10}$—O(CO); (CO)$NR_5$—$R_{10}$—$NR_5$(CO), [Si($R_7$)($R_8$)]$_p$; [Si($R_7$)($R_8$)—O]$_p$;
or $R_4$, if n=2, is $C_{10}$-$C_{50}$alkylene which is interrupted by one or more groups selected from the group consisting of O, (CO), $NR_5$ and $NR_{17}$, which interrupted $C_{10}$-$C_{50}$alkylene is substituted by one or more OH;
A is $PF_6$, $SbF_6$, $AsF_6$ or $B(C_6F_5)_4$;
$R_5$ is hydrogen, (CO)$R_6$, phenyl, $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$cycloalkyl, OH or by NCO,
$C_3$-$C_{12}$cycloalkyl which is unsubstituted or substituted by one or more $C_1$-$C_4$alkyl, $C_1$-$C_4$alkoxy, OH or by NCO;
$R_6$ is $C_1$-$C_{12}$alkyl, $C_2$-$C_{12}$alkyl which is interrupted by one or more 0, wherein said $C_1$-$C_{12}$alkyl or interrupted $C_2$-$C_{12}$alkyl is unsubstituted or substituted by one or more $C_3$-$C_7$-cycloalkyl, OH, NCO or by phenyl which is substituted by NCO;
or $R_6$ is $C_3$-$C_{12}$cycloalkyl, $C_2$-$C_{10}$alkenyl which is unsubstituted or substituted by one or more $C_1$-$C_4$alkyl, OH or $C_1$-$C_4$alkoxy;
or $R_6$ is $C_6$-$C_{14}$aryl which is unsubstituted or substituted by $C_1$-$C_{12}$alkyl, $C_1$-$C_{12}$alkoxy, NCO or by NCO-substituted $C_1$-$C_{12}$alkyl;
or $R_5$ and $R_6$ together with the N-atom form a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;
$R_7$, $R_8$ and $R_9$ independently of each other are $C_1$-$C_4$alkyl, $C_6$-$C_{14}$aryl or $C_1$-$C_4$alkoxy;
$R_{10}$ is $C_2$-$C_{18}$alkylene, $C_2$-$C_{18}$alkylene which is interrupted by one or more O, $NR_5$ or S, wherein said $C_2$-$C_{18}$alkylene or interrupted $C_2$-$C_{18}$alkylene is unsubstituted or substituted by one or more $C_1$-$C_4$alkyl, $C_1$-$C_4$alkoxy or by OH;
m is 1, 2 or 3;
o is 0-10;
p is 1-10;
Q represents one or two inorganic or organic cations with a charge of m;
$Y_1$ is a bond, O, S, $NR_5$, O(CO)—* or O(CO)—$CH_2$—O—*, wherein the asterix denotes the bond to the phenyl ring of the group (A), (B), (D), or (E);
$Y_2$ is a bond, O, S or $NR_5$;
$R_{11}$ and $R_{12}$ independently of each other are $C_1$-$C_{10}$alkyl, $C_2$-$C_{10}$alkenyl or phenyl-$C_1$-$C_4$-alkyl which is unsubstituted or substituted by $C_1$-$C_4$alkyl, or $R_{11}$ and $R_{12}$ together with the C-atom to which they are attached are cyclohexyl or cyclopentyl;

Z is OH or $NR_{13}R_{14}$;

$Z_1$ is $C_1$-$C_{12}$alkoxy or $C_2$-$C_{12}$alkoxy which is interrupted by one or more O, wherein said $C_1$-$C_{12}$alkoxy or interrupted $C_2$-$C_{12}$alkoxy is unsubstituted or substituted by OH;

$R_{13}$ and $R_{14}$ independently of each other are $C_1$-$C_{12}$alkyl, $C_1$-$C_{12}$alkyl which is substituted by one or more OH or halogen; or $R_{13}$ and $R_{14}$ together with the N-atom to which they are attached form a 5- or 6-membered unsaturated or saturated ring, which ring is uninterrupted or interrupted by O or $NR_{15}$;

$R_{15}$ is $C_1$-$C_4$alkyl;

$R_{16}$ is hydrogen or $C_1$-$C_4$alkyl; and $R_{17}$ is (CO)—O—$CH_2CH_2$—O(CO)—CH=$CH_2$;

(i) by contacting elemental phosphorus $[P]_\infty$ or preferably $P(Hal)_3$ with a reducing metal, optionally in the presence of a catalyst or an activator, in a solvent to obtain metal phosphides $Me_vP_w$; wherein for example v is 4-6 and w is 4-6;

(ii) adding a proton source, for example a sterically hindered alcohol, optionally in the presence of a catalyst or an activator, to obtain metal dihydrogen phosphides $MePH_2$;

(iii) subsequent reaction with z acid halides of formula (XX), or/and (XX') or/and (2-z) carboxylic acid esters of formula (XXI) or/and (XXI')

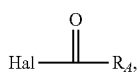
(XX)

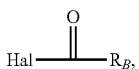
(XX')

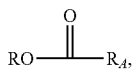
(XXI)

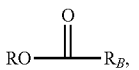
(XXI')

wherein R is the residue of an alcohol and $R_A$ and $R_B$ are as defined above, and z is 0, 1 or 2 to obtain a metallated compound of formula

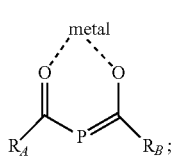
(X)

a1) reacting the obtained metallized phosphine complex of the formula (X) or a phosphine of the formula (XI)

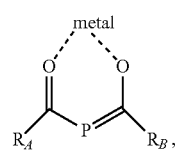
(X)

wherein $R_A$

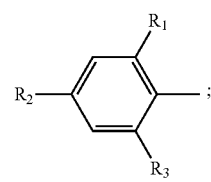

$R_B$ is a group

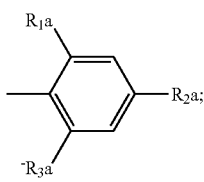

and $R_1$, $R_2$, $R_3$, $R_{1a}$, $R_{2a}$ and $R_{3a}$ are as defined above;

with an oxidation agent, to obtain a compound of formula (I), wherein $R_4$ is hydrgen and X and Y are O;

or a2) reacting a metallized phosphine complex of the formula (X) or a phosphine of the formula (XI) as defined above, with a sulfuration agent to obtain compounds of formula (I), wherein $R_4$ is hydrogen and X and Y are S;

or a3) reacting a metallized phosphine complex of the formula (X) or a phosphine of the formula (XI) as defined above, with an oxidation agent, in the presence of a base, to obtain compounds of formula (I), wherein $X_1$ and Y are O;

or a4) reacting a metallized phosphine complex of the formula (X) or a phosphine of the formula (XI) as defined above, with a sulfuration agent in the presence of a base to obtain compounds of formula (II), wherein X and Y are S.

Subject of the invention further is a process for the preparation of compounds of the formula (I), as defined above, wherein Q denotes a metal cation, as for example Cu, Ag or Au, or an organic cation as for example ammonium cations such as

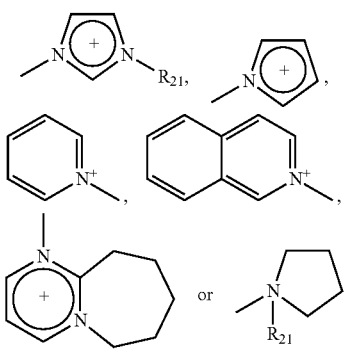

or methyl(trisoctyl)ammonium, characterized in that after any of the processes as defined above a corresponding ion exchange reaction is performed.

Subject of the invention further is a process for the preparation of compounds of the formula (II), as defined above, wherein Q denotes a metal cation, as for example Cu, Ag or Au, characterized in that in any of the processes as defined above the intermediate wherein X is O and $R_4$ is hydrogen is directly reacted with a metal salt or metal complex salt, as for example $CuSO_4 \cdot 5H_2O$, provided that the anion and/or additional ligands of the metal salt is capable to accept protons.

Preferred are compounds of the formula (I) or (II), wherein $R_1$, $R_2$, $R_3$, $R_{1a}$, $R_{2a}$ and $R_{3a}$ independently of each other are $C_1$-$C_4$alkyl;

X is O, $NR_5$ or S; or, if $R_4$ is Cl, X is a direct bond;

Y is O or S;

n is 1 or 2;

$R_4$, if n is 1, is hydrogen, $(CO)NR_5R_6$, $[Si(R_7)(R_8)—O]_o—Si(R_7)(R_8)(R_9)$, $C_1$-$C_{28}$alkyl, $C_2$-$C_{28}$alkyl which is interrupted by one or more O; wherein said $C_1$-$C_{28}$alkyl or interrupted $C_2$-$C_{28}$alkyl is unsubstituted or substituted by one or more substituents selected from the group consisting of OH,

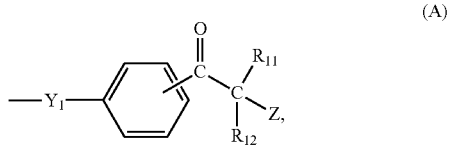

(A)

and $C_3$-$C_{12}$cycloalkyl;

or $R_4$, if n is 1, is $C_6$-$C_{10}$aryl;

or $R_4$ if n is 1 is Cl, provided that X is a direct bond;

$R_4$, if n=2, is $[Si(R_7)(R_8)—O]_p$ or $C_2$-$C_{18}$alkylene interrupted by one or more O;

$R_5$ is hydrogen;

$R_6$ is $C_3$-$C_{12}$cycloalkyl;

$R_7$, $R_8$ and $R_9$ independently of each other are $C_1$-$C_4$alkyl or $C_1$-$C_4$alkoxy;

$X_1$ is O or S;

m is 1;

o is 0;

p is 1;

Q as an inorganic or organic cation is an alkali metal, $Cu^{2+}$, (tetra($C_1$-$C_8$alkyl)ammonium, tris($C_1$-$C_4$alkyl)ammonium, cyclohexylammonium or 1H-diazole;

$Y_1$ is a bond, O, S or $NR_5$;

$R_{11}$ and $R_{12}$ independently of each other are $C_1$-$C_{10}$alkyl or phenyl-$C_1$-$C_4$-alkyl;

Z is OH or $NR_{13}R_{14}$;

$R_{13}$ and $R_{14}$ independently of each other are $C_1$-$C_{12}$alkyl;

or $R_{13}$ and $R_{14}$ together with the N-atom to which they are attached form a 6-membered saturated ring, which ring is interrupted by O;

provided that (i) if n is 1, $R_1$, $R_2$ and $R_3$ as $C_1$-$C_4$alkyl are $CH_3$ and X is O, $R_4$ as $C_1$-$C_{28}$alkyl is not methyl, ethyl, n-propyl, 2-propyl, n-butyl, 1-methyl-prop-1-yl, tert-butyl, n-hexyl.

Interesting are compounds of the formula (I) or (II) as defined above with provisos (i'), (ii), (iii), where proviso (i') is (i') if n is 1, $R_1$, $R_2$ and $R_3$ as $C_1$-$C_4$alkyl are $CH_3$ and X is O, $R_4$ as $C_1$-$C_{28}$alkyl is not $C_1$-$C_{18}$alkyl;

and provisos (ii) and (iii) are as defined above.

Further interesting are compounds of the formula (I) as defined above, wherein $R_4$ is halogen, in particular Cl and X is a direct bond.

Emphasis has to be laid on compounds of the formula (I) as defined above.

In particular interesting are compounds of the formula (I), wherein n is 1.

Other interesting compounds of formula (I) are such, wherein n is 2, X is O an $R_4$ is $C_2$-$C_{18}$alkylene interrupted by one or more O, which is unsubstituted or substituted by OH, in particular $R_4$ is $C_2$-$C_{18}$alkylene interrupted by one or more O, which is by OH.

Further of interest are compounds of the formula (I), wherein n is 1 or 2;

X is O and $R_4$ is $C_2$-$C_{28}$alkylene interrupted by one or more O, which is unsubstituted or substituted by OH, in particular $R_4$ is $C_2$-$C_{18}$alkylene interrupted by one or more O, which is by OH;

or wherein X is S or $NR_5$ and $R_4$, if n is 1, is hydrogen, $(CO)R_6$, $(CO)OR_6$, $(CO)NR_5R_6$, $(SO_2)$—$R_6$, $[Si(R_7)(R_8)]_o$—$Si(R_7)(R_8)(R_9)$, $[Si(R_7)(R_8)—O]_o$—$Si(R_7)(R_8)(R_9)$, $C_1$-$C_{28}$alkyl, $C_2$-$C_{28}$alkyl which is interrupted by one or more O, $NR_5$, S, (CO), (CO)O, or $SO_2$; wherein said $C_1$-$C_{28}$alkyl or interrupted $C_2$-$C_{28}$alkyl is unsubstituted or substituted by one or more substituents selected from the group consisting of OH, halide, $C_6$-$C_{14}$aryl, $[Si(R_7)(R_8)]_o$—$Si(R_7)(R_8)(R_9)$, $[Si(R_7)(R_8)—O]_o$—$Si(R_7)(R_8)(R_9)$, $N(R_5)_2$,

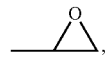

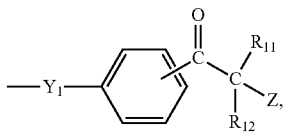

(A)

(B)

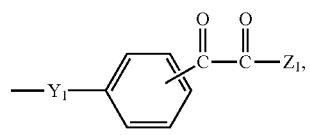

(C)

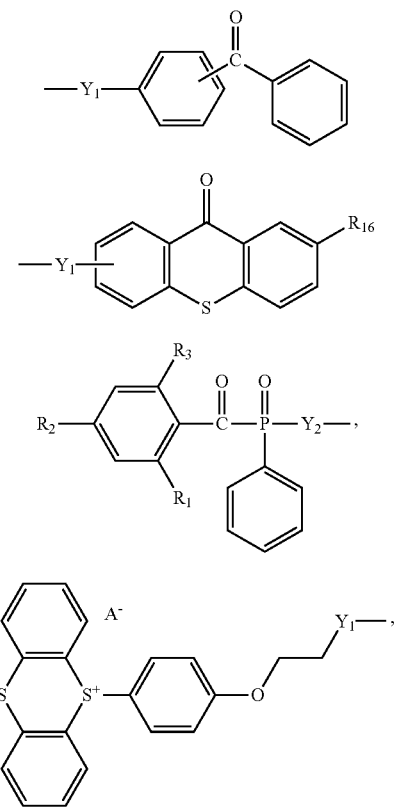

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH;

or $R_4$, if n is 1, is $C_6$-$C_{10}$aryl which is unsubstituted or substituted by one or more $C_1$-$C_{12}$alkyl, $C_2$-$C_{20}$alkyl which is interrupted by one or more O, $C_1$-$C_{12}$-alkoxy or by OH;

or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;

or $R_4$ if n is 1 is Cl, F or Br, provided that X is a direct bond;

$R_4$, if n=2, is $C_1$-$C_{18}$alkylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl or by naphthyl, $C_2$-$C_{18}$alkylene interrupted by one or more O, $NR_5$, S, (CO), O(CO)O, (NH)(CO)O, O(CO)(NH), O(CO) or (CO)O which interrupted $C_2$-$C_{18}$alkylene is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_2$-$C_{18}$alkenylene which is unsubstituted or substituted by one or more $C_1$-$C_4$alkyl, $C_1$-$C_4$alkoxy or by OH, $C_2$-$C_{18}$alkenylene which is interrupted by one or more O or $NR_5$ which interrupted $C_2$-$C_{18}$alkenylene is unsubstituted or substituted by one or more $C_1$-$C_4$alkyl, $C_1$-$C_4$alkoxy or by OH, $C_5$-$C_8$cycloalkylene which is unsubstituted or substituted by one or more $C_1$-$C_8$alkyl, $C_1$-$C_8$alkoxy, OH, halogen, $C_2$-$C_8$alkenyl, $COOR_6$, $C_1$-$C_{20}$acyl, phenyl, naphthyl or by $C_1$-$C_8$hydroxyalkyl, $C_5$-$C_8$cycloalkylene which is interrupted by one or more O or $NR_5$ which interrupted $C_5$-$C_8$cycloalkylene is unsubstituted or substituted by one or more $C_1$-$C_4$-alkyl, $C_1$-$C_4$alkoxy or by OH, $C_6$-$C_{10}$arylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl, naphthyl or by $C_1$-$C_8$hydroxyalkyl;

or $R_4$, if n=2, is $(CO)R_{10}(CO)$; $(CO)O-R_{10}-O(CO)$; $(CO)NR_5-R_{10}-NR_5(CO)$, $[Si(R_7)(R_8)]_p$; $[Si(R_7)(R_8)-O]_p$;

or $R_4$, if n=2, is $C_{10}$-$C_{50}$alkylene which is interrupted by one or more groups selected from the group consisting of O, (CO), $NR_5$ and $NR_{17}$, which interrupted $C_{10}$-$C_{50}$alkylene is substituted by one or more OH;

A is $PF_6$, $SbF_6$, $AsF_6$ or $B(C_6F_5)_4$;

$R_5$ is hydrogen, $(CO)R_6$, phenyl, $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$cycloalkyl, OH or by NCO, $C_3$-$C_{12}$cycloalkyl which is unsubstituted or substituted by one or more $C_1$-$C_4$alkyl, $C_1$-$C_4$alkoxy, OH or by NCO;

$R_6$ is $C_1$-$C_{12}$alkyl, $C_2$-$C_{12}$alkyl which is interrupted by one or more O, wherein said $C_1$-$C_{12}$alkyl or interrupted $C_2$-$C_{12}$alkyl is unsubstituted or substituted by one or more $C_3$-$C_7$-cycloalkyl, OH, NCO or by phenyl which is substituted by NCO;

or $R_6$ is $C_3$-$C_{12}$cycloalkyl, $C_2$-$C_{10}$alkenyl which is unsubstituted or substituted by one or more $C_1$-$C_4$alkyl, OH or $C_1$-$C_4$alkoxy;

or $R_6$ is $C_6$-$C_{14}$aryl which is unsubstituted or substituted by $C_1$-$C_{12}$alkyl, $C_1$-$C_{12}$alkoxy, NCO or by NCO-substituted $C_1$-$C_{12}$alkyl;

or $R_5$ and $R_6$ together with the N-atom form a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;

$R_7$, $R_8$ and $R_9$ independently of each other are $C_1$-$C_4$alkyl, $C_6$-$C_{14}$aryl or $C_1$-$C_4$alkoxy;

$R_{10}$ is $C_2$-$C_{18}$alkylene, $C_2$-$C_{18}$alkylene which is interrupted by one or more O, $NR_5$ or S, wherein said $C_2$-$C_{18}$alkylene or interrupted $C_2$-$C_{18}$alkylene is unsubstituted or substituted by one or more $C_1$-$C_4$alkyl, $C_1$-$C_4$alkoxy or by OH;

m is 1, 2 or 3, preferably 1 or 2;
o is 0-10;
p is 1-10;
$Y_1$ is a bond, O, S, $NR_5$, $O(CO)$—* or $O(CO)$—$CH_2$—O—*, wherein the asterix denotes the bond to the phenyl ring of the group (A), (B), (D), or (E);

$Y_2$ is a bond, O, S or $NR_5$;

$R_{11}$ and $R_{12}$ independently of each other are $C_1$-$C_{10}$alkyl, $C_2$-$C_{10}$alkenyl or phenyl-$C_1$-$C_4$-alkyl which is unsubstituted or substituted by $C_1$-$C_4$alkyl, or $R_{11}$ and $R_{12}$ together with the C-atom to which they are attached are cyclohexyl or cyclopentyl;

Z is OH or $NR_{13}R_{14}$;

$Z_1$ is $C_1$-$C_{12}$alkoxy or $C_2$-$C_{12}$alkoxy which is interrupted by one or more O, wherein said $C_1$-$C_{12}$alkoxy or interrupted $C_2$-$C_{12}$alkoxy is unsubstituted or substituted by OH;

$R_{13}$ and $R_{14}$ independently of each other are $C_1$-$C_{12}$alkyl, $C_1$-$C_{12}$alkyl which is substituted by one or more OH or halogen; or $R_{13}$ and $R_{14}$ together with the N-atom to which they are attached form a 5- or 6-membered unsaturated or saturated ring, which ring is uninterrupted or interrupted by O or $NR_{15}$;

$R_{15}$ is $C_1$-$C_4$alkyl;

$R_{16}$ is hydrogen or $C_1$-$C_4$alkyl; and $R_{17}$ is (CO)—O—$CH_2CH_2$—O(CO)—CH=$CH_2$;

provided that (iii) if n is 1, R, and $R_3$ as $C_1$-$C_4$alkoxy are methoxy, $R_2$ is hydrogen and X is $NR_5$, and $R_4$ together with $R_5$ and the N-atom forms a 5 or 6-membered saturated ring, said ring is not piperid-1-yl.

Further of interest are compounds of the formula (II), wherein m is 1, 2 or 3, in particular 2;

$R_1$, $R_2$, $R_3$, $R_{1a}$, $R_{2a}$ and $R_{3a}$ are as defined above;

$X_1$ is O; and

Q is Ag, Au, Cu, in particular Cu.

$R_1$, $R_2$, $R_3$, $R_{1a}$, $R_{2a}$ and $R_{3a}$ for example independently of each other are $C_1$-$C_4$alkyl, $C_1$-$C_4$alkoxy or halogen; in particular $C_1$-$C_4$alkyl. For example $R_1$, $R_2$ and $R_3$ are identical. Or for example $R_{1a}$, $R_{2a}$ and $R_{3a}$ are identical. Preferably $R_1$, $R_2$ and $R_3$, and $R_{1a}$, $R_{2a}$ and $R_{3a}$ are identical.

Most preferred is $R_1$, $R_2$ and $R_3$ are $CH_3$

X is for example O, $NR_5$ or S; or, if $R_4$ is Cl, F or Br, X is a direct bond; X in particular is O or, if $R_4$ is Cl, F or Br, X is a direct bond. For example X is O.

Interestingly X is for example a direct bond and $R_4$ is Cl.

X is for example S or $NR_5$.

X is for example S.

Y is O or S; in particular Y is O.

$R_4$, if n is 1, is for example hydrogen, (CO)$R_6$, (CO)O$R_6$, (CO)$NR_5R_6$, ($SO_2$)$R_6$, $C_1$-$C_{28}$alkyl, $C_2$-$C_{28}$alkyl which is interrupted by one or more O, $NR_5$ or S; wherein said $C_1$-$C_{28}$alkyl or interrupted $C_2$-$C_{28}$alkyl is unsubstituted or substituted by one or more substituents selected from the group consisting of OH, N($R_5$)$_2$,

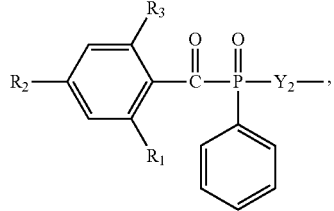

(F)

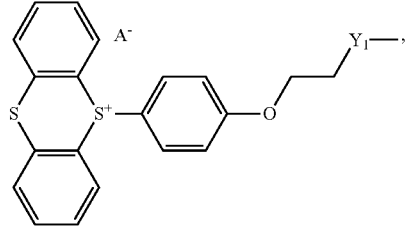

(G)

propenoyloxy and 2-methylpropenoyloxy; or $R_4$, if n is 1, is $C_6$-$C_{10}$aryl which is unsubstituted or substituted by one or more $C_1$-$C_{12}$alkyl; or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH; or $R_4$ if n is 1 is Cl, F or Br, provided that X is a direct bond.

Or $R_4$, if n is 1, is for example $C_1$-$C_{28}$alkyl or $C_2$-$C_{28}$alkyl which is interrupted by one or more O, $NR_5$ or S; wherein said $C_1$-$C_{28}$alkyl or interrupted $C_2$-$C_{28}$alkyl is unsubstituted or substituted by one or more substituents selected from the group consisting of OH, halide, $C_6$-$C_{14}$aryl, [Si($R_7$)($R_8$)]$_o$—Si($R_7$)($R_8$)($R_9$), [Si($R_7$)($R_8$)—O]$_o$—Si($R_7$)($R_8$)($R_9$), N($R_5$)$_2$,

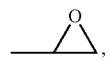

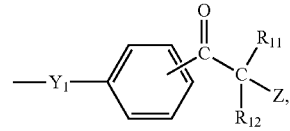

(A)

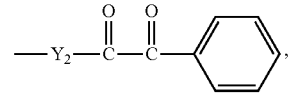

(C)

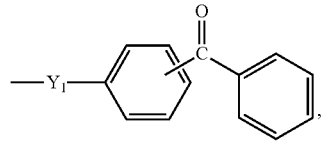

(D)

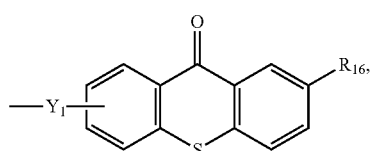

(E)

propenoyloxy, 2-methylpropenoyloxy, $C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH.

Or $R_4$, if n is 1, is for example hydrogen, $(CO)R_6$, $(CO)OR_6$, $(CO)NR_5R_6$, $(SO_2)$—$R_6$, $[Si(R_7(R_8)]_o$—$Si(R_7)(R_8)(R_9)$, $[Si(R_7)(R_8)$—$O]_o$—$Si(R_7)(R_8)(R_9)$, $C_1$-$C_{28}$alkyl, $C_2$-$C_{28}$alkyl which is interrupted by one or more O, $NR_5$, S, (CO), (CO)O, or $SO_2$; wherein said $C_1$-$C_{28}$alkyl or interrupted $C_2$-$C_{28}$alkyl is unsubstituted or substituted by one or more substituents selected from the group consisting of
OH, halide, $C_6$-$C_{14}$aryl, $[Si(R_7)(R_8)]_o$—$Si(R_7)(R_8)(R_9)$, $[Si(R_7)(R_8)$—$O]_o$—$Si(R_7)(R_8)(R_9)$, $N(R_5)_2$,

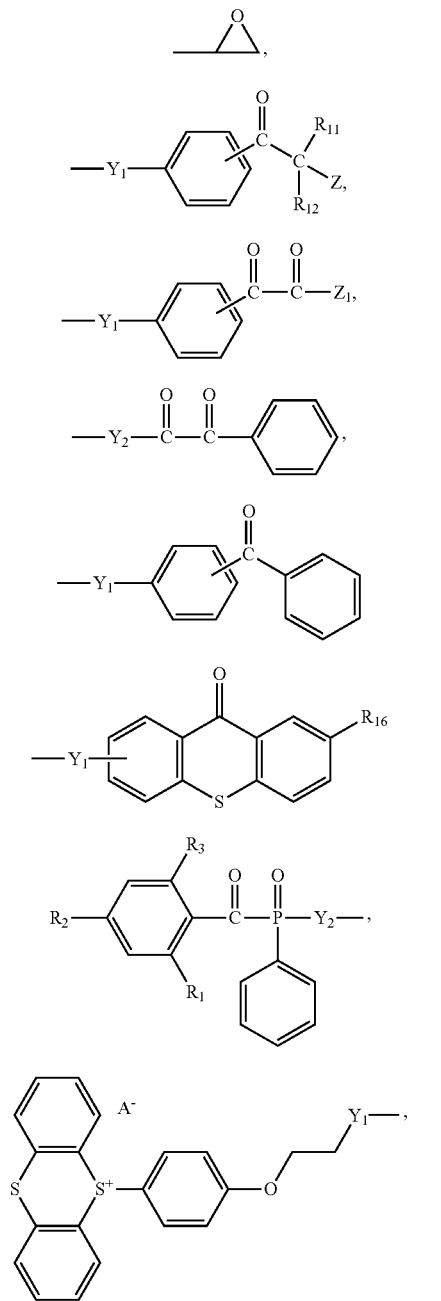

$C_3$-$C_{12}$cycloalkyl which is unsubstituted or substituted by $C_1$-$C_4$-alkyl, $C_1$-$C_4$alkoxy or by OH, $C_3$-$C_{12}$cycloalkyl which is interrupted by one or more O, $NR_5$ or S and which interrupted $C_3$-$C_{12}$cycloalkyl is unsubstituted or substituted by $C_1$-$C_4$alkyl, $C_1$-$C_4$-alkoxy or by OH, and $C_6$-$C_{14}$aryl which is unsubstituted or substituted by $C_1$-$C_4$alkyl, $C_1$-$C_4$alkoxy or by OH;

or $R_4$, if n is 1, is $C_6$-$C_{10}$aryl which is unsubstituted or substituted by one or more $C_1$-$C_{12}$alkyl, $C_2$-$C_{20}$alkyl which is interrupted by one or more O, $C_1$-$C_{12}$-alkoxy or by OH;

or $R_4$ if n is 1 and X is $NR_5$, together with $R_5$ and the N-atom forms a 5 or 6-membered saturated ring which is uninterrupted or interrupted by O or $NR_5$ and which uninterrupted or interrupted ring is unsubstituted or substituted by one or more $C_1$-$C_4$alkyl, $C_1$-$C_4$alkoxy or by OH;

or $R_4$ if n is 1 is Cl, F or Br, provided that X is a direct bond.

Or $R_4$, if n is 1, is for example $C_1$-$C_{28}$alkyl or $C_2$-$C_{28}$alkyl which is interrupted by one or more O, $NR_5$ or S; wherein said $C_1$-$C_{28}$alkyl or interrupted $C_2$-$C_{28}$alkyl is unsubstituted or substituted by one or more substituents selected from the group consisting of

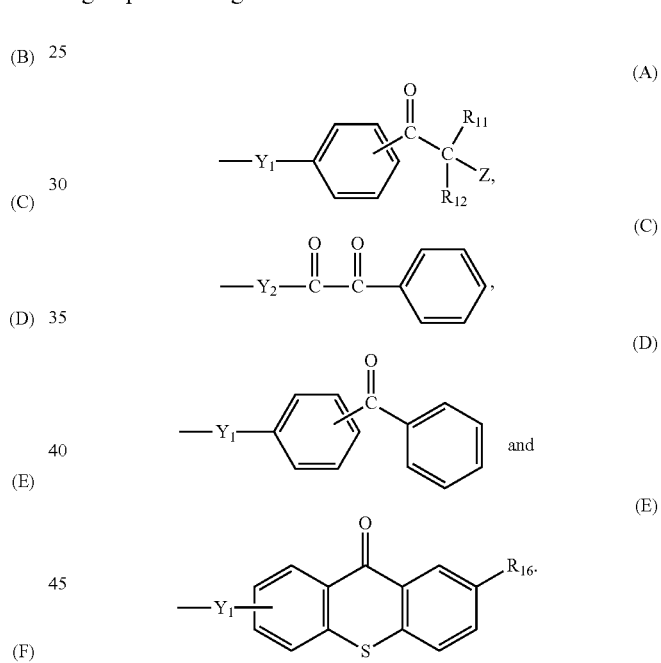

Or $R_4$, if n is 1, is for example $C_2$-$C_{28}$alkyl which is interrupted by one or more O and is unsubstituted or substituted by OH.

$R_4$, if n=2, is for example $C_1$-$C_{18}$alkylene which is unsubstituted or substituted by one or more $C_1$-$C_8$alkyl, $C_1$-$C_8$-alkoxy, OH, halogen, $C_2$-$C_8$alkenyl, $COOR_6$, $C_1$-$C_{20}$acyl, phenyl or by naphthyl; or $R_4$, if n=2, is (CO)$R_{10}$(CO); (CO)O—$R_{10}$—O(CO); (CO)$NR_5$—$R_{10}$—$NR_5$(CO), $[Si(R_7)(R_8)]_p$; $[Si(R_7)(R_8)$—$O]_p$; or $R_4$, if n=2, is $C_4$-$C_{50}$alkylene which is interrupted by one or more groups selected from the group consisting of O, (CO), $NR_5$ and $NR_{17}$, which interrupted $C_{10}$-$C_{50}$alkylene is substituted by one or more OH.

Or $R_4$, if n is 2, is for example $C_4$-$C_{50}$alkylene which is interrupted by one or more O and is unsubstituted or substituted by OH.

Or $R_4$, if n is 2, is for example $C_2$-$C_{18}$alkylene interrupted by one or more O, which is unsubstituted or substituted by OH. In particular $R_4$ is $C_2$-$C_{18}$alkylene interrupted by one or more O, which is unsubstituted or substituted by OH.

$R_5$ is for example hydrogen, phenyl or $C_1$-$C_{12}$alkyl.

Or $R_5$ is for example hydrogen or $C_1$-$C_{12}$alkyl, in particular hydrogen.

$R_6$ is for example $C_1$-$C_{12}$alkyl or $C_3$-$C_{12}$cycloalkyl; or $R_5$ and $R_6$ together with the N-atom form a 5 or 6-membered saturated ring which is uninterrupted or interrupted by O or $NR_5$.

Or $R_6$ is for example $C_1$-$C_{12}$alkyl or $C_3$-$C_{12}$cycloalkyl; or $R_5$ and $R_6$ together with the N-atom form a morpholino ring.

Or $R_6$ is for example $C_1$-$C_{12}$alkyl or $C_3$-$C_{12}$cycloalkyl, in particular $C_3$-$C_{12}$cycloalkyl, e.g. cyclohexyl.

$R_7$, $R_8$ and $R_9$ independently of each other are $C_1$-$C_4$alkyl, $C_6$-$C_{14}$aryl or $C_1$-$C_4$alkoxy; in particular are $C_1$-$C_4$alkyl or $C_1$-$C_4$alkoxy, preferably are methyl or methoxy.

$R_{10}$ is for example $C_2$-$C_{18}$alkylene, $C_2$-$C_{18}$alkylene which is interrupted by one or more O, $NR_5$ or S, wherein said $C_2$-$C_{18}$alkylene or interrupted $C_2$-$C_{18}$alkylene is unsubstituted or substituted by one or more $C_1$-$C_4$alkyl, $C_1$-$C_4$alkoxy or by OH; in particular $C_2$-$C_{18}$alkylene.

$X_1$ is O or S; in particular O.

m is 1 or 2; preferably m is 1.

Interesting also are compounds of the formula (II), wherein m is 2.

o is 0-10; or for example 0-5.

p is 1-10; or for example 1-5.

$Y_1$ is a bond, O, S, $NR_5$, O(CO)—* or O(CO)—$CH_2$—O—*, wherein the asterix denotes the bond to the phenyl ring of the group (A), (B), (D), or (E). In particular $Y_1$ denotes a bond, O, S, $NR_5$, preferably a bond, O or $NR_5$.

$R_{11}$ and $R_{12}$ for example independently of each other are $C_1$-$C_{10}$alkyl, $C_2$-$C_{10}$alkenyl or phenyl-$C_1$-$C_4$-alkyl which is unsubstituted or substituted by $C_1$-$C_4$alkyl or $R_{11}$ and $R_{12}$ together with the C-atom to which they are attached are cyclohexyl or cyclopentyl.

Or $R_{11}$ and $R_{12}$ for example independently of each other are $C_1$-$C_4$alkyl, $C_2$-$C_5$alkenyl or benzyl, which is unsubstituted or substituted by methyl, or $R_{11}$ and $R_{12}$ together with the C-atom to which they are attached are cyclohexyl.

Z is OH or $NR_{13}R_{14}$; in particular OH.

$Z_1$ is for example $C_1$-$C_{12}$alkoxy or $C_2$-$C_{12}$alkoxy which is interrupted by one or more O, wherein said $C_1$-$C_{12}$alkoxy or interrupted $C_2$-$C_{12}$alkoxy is unsubstituted or substituted by OH.

$Z_1$ is $C_1$-$C_{12}$alkoxy, in particular $C_1$-$C_4$alkoxy.

$R_{13}$ and $R_{14}$ for example independently of each other are $C_1$-$C_{12}$ alkyl; or $R_{13}$ and $R_{14}$ together with the N-atom to which they are attached form a 5- or 6-membered unsaturated or saturated ring, which ring is uninterrupted or interrupted by O or $NR_{15}$.

Or $R_{13}$ and $R_{14}$ for example independently of each other are $C_1$-$C_{12}$alkyl, in particular $C_1$-$C_4$alkyl; or $R_{13}$ and $R_{14}$ together with the N-atom to which they are attached form a 6-membered unsaturated or saturated ring, which ring is uninterrupted or interrupted by O or $NR_{15}$, in particular said ring is a morpholino ring.

$R_{15}$ is $C_1$-$C_4$alkyl, in particular methyl.

$R_{16}$ is hydrogen or $C_1$-$C_4$alkyl, in particular hydrogen or methyl, preferably hydrogen, In accordance with the invention, the photoinitiator can be used as photoinitiator for the photopolymerization of ethylenically unsaturated compounds or of mixtures which comprise such compounds.

The invention therefore also relates to photopolymerizable compositions comprising (a) at least one ethylenically unsaturated photopolymerizable compound, e.g. a monomeric or oligomeric ethylenically unsaturated compound, and (b) as photoinitiator, at least one compound of the formula (I) or (II) as defined above, including the defined provisos.

The composition may comprise additionally to the components (a) and (b) at least one further photoinitiator (c) and/or other (customary) additives (d). In other words the composition comprises components (a) and (b) and a component selected from the group consisting of further photoinitiators (c) and other (customary) additives (d).

The unsaturated compounds (a) for example contain one or more olefinic double bonds. They are of low molecular weight (monomeric) or higher molecular weight (oligomeric).

Examples of monomers containing a double bond are (meth)acrylic acid and salts thereof, (meth)acrylic acid esters, e.g. alkyl esters such as methyl, ethyl, 2-chloroethyl, N-dimethylaminoethyl, n-butyl, isobutyl, pentyl, hexyl, cyclohexyl, 2-ethylhexyl, octyl, isobornyl[2-exobornyl]ester, phenyl, benzyl and o-, m- and p-hydroxyphenyl ester, hydroxyalkyl esters, e.g. 2-hydroxyethyl, 2-hydroxypropyl, 4-hydroxybutyl, 3,4-dihydroxybutyl or glycerol[1,2,3-propanetriol]ester, epoxyalkyl esters, e.g. glycidyl, 2,3-epoxybutyl, 3,4-epoxybutyl, 2,3-epoxycyclohexyl, 10,11-epoxyundecyl ester, (meth)acrylamides, N-substituted (meth)acrylamides, e.g. N-methylolacrylamide, N-methylolmethacrylamide, N-ethylacrylamide, N-ethylmethacrylamide, N-hexylacrylamide, N-hexylmethacrylamide, N-cyclohexylacrylamide, N-cyclohexylmethacrylamide, N-hydroxyethylacrylamide, N-phenylacrylamide, N-phenylmethacrylamide, N-benzylacrylamide, N-benzylmethacrylamide, N-nitrophenylacrylamide, N-nitrophenylmethacrylamide, N-ethyl-N-phenylacrylamide, N-ethyl-N-phenylmethacrylamide, N-(4-hydroxyphenyl)acrylamide and N-(4-hydroxyphenyl)methacrylamide, IBMAA (N-isobutoxymethylacrylamide), (meth)acrylonitriles, unsaturated acid anhydrides such as itaconic anhydride, maleic anhydride, 2,3-dimethylmaleic anhydride, 2-chloromaleic anhydride, unsaturated esters such as maleic acid esters, phthalic acid esters, itaconic acid esters [methylenesuccinic acid esters], styrenes such as methylstyrene, chloromethylstyrene and o-, m- and p-hydroxystyrene, divinylbenzene, vinyl ethers such as isobutyl vinyl ether, ethyl vinyl ether, 2-chloroethyl vinyl ether, hydroxyethyl vinyl ether, propyl vinyl ether, butyl vinyl ether, isobutyl vinyl ether, octyl vinyl ether and phenyl vinyl ether, vinyl and allyl esters such as vinyl acetate, vinyl acrylate, vinyl chloroacetate, vinyl butyrate and vinyl benzoate, divinyl succinate, diallyl phthalate, triallyl phosphate, vinyl chloride and vinylidene chloride, isocyanurates such as triallyl isocyanurate and tris(2-acryloylethyl) isocyanurate, N-vinylheterocyclic compounds such as N-vinylpyrrolidones or substituted N-vinylpyrrolidones, N-vinylcaprolactam or substituted N-vinylcaprolactams, N-vinylcarbazole, N-vinylpyridine.

Further examples of suitable esters are:

diacrylate esters such as 1,6-hexanediol diacrylate (HDDA), ethylene glycol diacrylate, propylene glycol diacrylate, dipropylene glycol diacrylate, tripropylene glycol diacrylate, neopentyl glycol diacrylate, hexamethylene glycol diacrylate and bisphenol A diacrylate, trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having molecular weights of from 200 to 1500, or mixtures thereof.

Frequently also used are acrylic acid esters of alkoxylated alcohols, e.g. glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Examples of higher-molecular-weight unsaturated compounds (oligomers, prepolymers) are esters of ethylenically unsaturated mono- or poly-functional carboxylic acids and polyols or polyepoxides, and polymers having ethylenically unsaturated groups in the chain or in side groups such as, for example, unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more of such polymers.

Examples of suitable mono- or poly-functional unsaturated carboxylic acids are acrylic acid, methacrylic acid, crotonic acid, cinnamic acid, maleic acid, fumaric acid, itaconic acid, unsaturated fatty acids such as linolenic acid or oleic acid. Acrylic and methacrylic acid are preferred.

However, saturated di- or poly-carboxylic acids in admixture with unsaturated carboxylic acids may also be used. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

As polyols, aromatic and especially aliphatic and cycloaliphatic polyols are suitable. Examples of aromatic polyols are hydroquinone, 4,4'-dihydroxydiphenyl, 2,2-di(4-hydroxyphenyl)propane, and also novolaks and resols. Examples of polyepoxides are those based on the mentioned polyols, especially aromatic polyols and epichlorohydrin. Also suitable as polyols are polymers and copolymers that contain hydroxyl groups in the polymer chain or in side groups such as, for example, polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of polyurethanes are those composed of saturated diisocyanates and unsaturated diols or unsaturated diisocyanates and saturated diols.

Preference is given to (meth)acrylated epoxy esters, (meth)acrylated polyesters, polyesters carrying vinyl groups, (meth)acrylated polyurethanes, (meth)acrylated polyethers and polyols, in particular to the acrylated corresponding components.

Suitable components (a) are also acrylates which have been modified by reaction with primary or secondary amines, as described, for example, in U.S. Pat. No. 3,844,916, in EP280222, in U.S. Pat. No. 5,482,649 or in U.S. Pat. No. 5,734,002. Such amine-modified acrylates are also termed amine acrylates. Amine acrylates are obtainable, for example, under the name EBECRYL 80, EBECRYL 81, EBECRYL 83, EBECRYL 7100 from UCB Chemicals, under the name Laromer PO 83F, Laromer PO 84F, Laromer PO 94F from BASF, under the name PHOTOMER 4775 F, PHOTOMER 4967 F from Cognis or under the name CN501, CN503, CN550 from Cray Valley and GENOMER 5275 from Rahn.

Some acrylate binders expecially designed for low extractables and odour applications can also be used in the formulation. Such resins are commercially available for example under the tradename Ebecryl LEO resins.

Furthermore, cationically UV-curable compositions may be used as part of component (a) for hybrid cationic/radical UV-curing. Such systems typically comprise aliphatic and/or aromatic epoxides, at least one polyol or polyvinyl polyol or oxetane and also at least one photoinitiator that generates cations. The said epoxides, polyols and polyvinyl polyols are known in the art and commercially available. The customarily used photoinitiators are iodonium and sulfonium salts as described, for example, in U.S. Pat. No. 6,306,555. In addition, ethylenically unsaturated compounds may be added to the said cationically UV-curable compositions.

The use cationically curable components and ethylenically unsatured compounds is especially useful, when the bisacylphosphinic acid derivatives of formula (I) contain an additional cationic photoinitiator moiety, as it is for example the case for structures of formula (I) carrying a sulfonium salt photoactive moiety as described by formula (G).

It is also possible to add solvents or water to the compositions used in the process according to the invention. Suitable solvents are solvents which are known to the person skilled in the art and are conventional especially in surface-coating technology. Examples are various organic solvents such as, for example, ketones, e.g. methyl ethyl ketone, cyclohexanone; aromatic hydrocarbons, e.g. toluene, xylene or tetramethylbenzene; glycol ethers, e.g. diethylene glycol monoethyl ether, dipropylene glycol diethyl ether; esters, e.g. ethyl acetate; aliphatic hydrocarbons, e.g. hexane, octane, decane; or petroleum solvents, e.g. petroleum ether.

The invention relates also to compositions comprising, as component (a), at least one ethylenically unsaturated photopolymerisable compound dissolved or emulsified in water.

Such radiation-curable aqueous prepolymer dispersions are obtainable commercially in many variations. They are to be understood as being a dispersion consisting of water and at least one prepolymer dispersed therein. The concentration of the water in those systems is, for example, from 5 to 80% by weight, especially from 30 to 60% by weight. The radiation-curable prepolymer or prepolymer mixture is present in concentrations of, for example, from 95 to 20% by weight, especially from 70 to 40% by weight. The sum of the indicated percentages for water and prepolymer in those compositions is in each case 100; auxiliaries and additives, which are present in varying amounts depending on the intended use, are in addition thereto.

The radiation-curable film-forming prepolymers, which are dispersed or in many cases dissolved in water, are mono- or poly-functional ethylenically unsaturated prepolymers capable of initiation by free radicals and known per se for aqueous prepolymer dispersions; for example, they have a content of from 0.01 to 1.0 mol of polymerisable double bonds per 100 g of prepolymer and an average molecular weight of, for example, at least 400, especially from 500 to 10 000, although depending on the intended use prepolymers having higher molecular weights also come into consideration.

Used are, for example, polyesters containing polymerisable C—C double bonds and having an acid number of at most 10, polyethers containing polymerisable C—C double bonds, hydroxyl-group-containing reaction products of a polyepoxide containing at least two epoxide groups per molecule with at least one α,β-ethylenically unsaturated carboxylic acid, polyurethane (meth)acrylates and also acrylic copolymers containing α,β-ethylenically unsaturated acrylic radicals as described, for example, in EP012339. Mixtures of those prepolymers may also be used. Also suitable are, for example, the polymerisable prepolymers described in EP033896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on particular (meth) acrylic acid alkyl ester polymerisation products are described in EP041125; suitable water-dispersible, radiation-curable prepolymers obtained from urethane acrylates are to be found in, for example, DE2936039.

The photopolymerisable compounds (a) are used singly or in any desired mixture.

Component (a) may also comprise binders, that being especially advantageous when the photopolymerisable compounds are liquid or viscous substances. The amount of the binder may be, for example, from 5 to 95% by weight, preferably from 10 to 90% by weight and especially from 40 to 90% by weight, based on the total solid material. The binder is selected according to the field of use and the properties required therefor such as, for example, developability in aqueous and organic solvent systems, adhesion to substrates and sensitivity to oxygen.

Suitable binders are, for example, polymers having molecular weights of about 5 000-2 000 000, preferably 10 000-1 000 000. Examples are: homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, e.g. cellulose acetate, cellulose acetate butyrate, methylcellulose, ethylcellulose; polyvinyl butyral, polyvinyl formal, cyclised rubber, polyethers, e.g. polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers, e.g. polycaprolactam und poly(hexamethylene adipamide), polyesters, e.g. poly(ethylene glycol terephthalate) and poly(hexamethylene glycol succinate).

The unsaturated compounds may also be used in admixture with non-photopolymerisable film-forming components. The latter are, for example, physically drying polymers or solutions thereof in organic solvents, e.g. nitrocellulose or cellulose acetobutyrate, but may also be chemically or thermally curable resins, e.g. polyisocyanates, polyepoxides or melamine resins. Melamine resins are to be understood as including not only condensation products of melamine (=1,3,5-triazine-2,4,6-triamine) but also those of melamine derivatives. In general, the binder is a film-forming binder based on a thermoplastic or thermocurable resin, mainly a thermocurable resin. Examples thereof are alkyd, acrylic, polyester, phenol, melamine, epoxy and polyurethane resins and mixtures thereof. The concomitant use of thermally curable resins is of importance for use in so-called hybrid systems, which are both photopolymerised and also thermally crosslinked.

Component (a) may also comprise film-forming binders based on a thermoplastic or thermocurable resin, mainly a thermocurable resin. Examples thereof are alkyd, acrylic, polyester, phenol, melamine, epoxy and polyurethane resins and mixtures thereof. Examples thereof are described in, for example, Ullmann's Encyclopedia of Industrial Chemistry, 5th Ed., Vol. A18, pp. 368-426, VCH, Weinheim 1991.

The binder may be a binder that fully cures at cold or hot temperatures, for which the addition of a curing catalyst may be advantageous. Suitable catalysts which accelerate full curing of the binder are described in, for example, Ullmann's Encyclopedia of Industrial Chemistry, Vol. A18, p. 469, VCH Verlagsgesellschaft, Weinheim 1991.

WO99/03930; WO2000/010974 and WO2000/020517 describe maleimide-modified binders. Maleimide-modified binders of that kind may likewise be present in the photocurable composition of the present invention.

Examples of binders are:
1. surface-coatings based on cold- or hot-crosslinkable alkyd, acrylate, polyester, epoxy or melamine resins or mixtures of such resins, optionally with the addition of a curing catalyst;
2. two-component polyurethane surface-coating compositions based on hydroxyl-group-containing acrylate, polyester or polyether resins and aliphatic or aromatic isocyanates, isocyanurates or polyisocyanates;
3. two-component polyurethane surface-coating compositions based on thiol-group-containing acrylate, polyester or polyether resins and aliphatic or aromatic isocyanates, isocyanurates or polyisocyanates;
4. single-component polyurethane surface-coating compositions based on blocked isocyanates, isocyanurates or polyisocyanates, which are unblocked during stoving; optionally, the addition of melamine resins is also possible;
5. single-component polyurethane surface-coating compositions based on aliphatic or aromatic urethanes or polyurethanes and hydroxyl-group-containing acrylate, polyester or polyether resins;
6. single-component polyurethane surface-coating compositions based on aliphatic or aromatic urethane acrylates or polyurethane acrylates having free amine groups in the urethane structure, and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides and polyepoxides;
12. two-component surface-coating compositions based on (poly)oxazolines and anhydride-group-containing acrylate resins or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically crosslinking acrylate resins, in combination with etherified melamine resins;
15. surface-coating systems, especially clearcoats, based on malonate-blocked isocyanates with melamine resins (e.g. hexamethoxymethyl melamine) as crosslinkers (acidcatalysed);
16. UV-curable systems based on oligomeric urethane acrylates and/or acylate acrylates, optionally with the addition of other oligomers or monomers;
17. dual-cure systems, which are first cured thermally and then UV-cured, or vice versa, wherein constituents of the surface-coating composition contain double bonds which can be made to react by UV light and photoinitiators and/or by electron-beam curing.

Both 1-component (1C) and 2-component (2C) systems may be used as binder. Examples of such systems are described in Ullmann's Encyclopedia of Industrial Chemistry, Vol. A18, Paints and Coatings, page 404-407, VCH Verlagsgesellschaft mbH, Weinheim (1991).

The composition can be optimised by specifically modifying the formulation, e.g. by varying the binder/crosslinker ratio. The person skilled in the art of coating or ink technology will be familiar with such measures.

The photopolymerizable composition of the invention for example additionally comprises a binder polymer (e), in particular a copolymer of methacrylate and methacrylic acid.

In addition to the photoinitiator, the photopolymerisable mixtures may comprise various additives (d). Examples thereof are thermal inhibitors, which are intended to prevent premature polymerisation, e.g. 2,2,6,6-tetramethyl-4-hydroxy-piperidin-1-oxyl (4-hydroxy-TEMPO) and derivatives thereof, e.g. bis(2,2,6,6-tetramethylpiperidin-1-oxyl-4-yl)decanedioate or polyalkyl-piperidin-N-oxyl radicals, 3-aryl-benzofuran-2-one and derivatives thereof, e.g. 5,7-di-tert-butyl-3-phenyl-3H-benzofuran-2-one (as described in, for example, WO01/42313), hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen.

As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS). Such compounds are widely known to the person skilled in the art.

Examples of such UV absorbers and light stabilisers are disclosed in WO04/074328, page 12, line 9 to page 14, line 23, said disclosure hereby is incorporated by reference.

Further, additives that are customary in the art such as, for example, antistatics, flow improvers and adhesion promoters may be used.

In accordance with the invention, if the formulation comprises binder, thermal drying or curing catalysts may additionally be added to the formulation as additional additives (d). Possible drying catalysts, or thermal curing catalysts, are, for example, organic metal compounds, amines or/and phosphines. Organic metal compounds are, for example, metal carboxylates, especially those of the metals Pb, Mn, Hf, Co, Zn, Zr or Cu, or metal chelates, especially those of the metals Hf, Al, Ti or Zr, or organometal compounds, such as e.g. organotin compounds. Examples of metal carboxylates are the stearates of Pb, Mn or Zn, the octoates of Co, Zn or Cu, the naphthenates of Mn and Co or the corresponding linoleates or tallates (tall oil, which contains rosin acids, oleic and linoleic acids). Examples of metal chelates are the aluminium, titanium or zirconium chelates of acetyl acetone, ethylacetyl acetate, salicylaldehyde, salicylaldoxime, o-hydroxyacetophenone or ethyltrifluoroacetyl acetate and the alkoxides of those metals. Examples of organotin compounds are dibutyltin oxide, dibutyltin dilaurate and dibutyltin dioctoate. Examples of amines are especially tertiary amines such as, for example, tributylamine, triethanolamine, N-methyldiethanolamine, N-dimethylethanolamine, N-ethylmorpholine, N-methylmorpholine and diazabicyclooctane (triethylenediamine) and the salts thereof. Further examples are quaternary ammonium salts, such as e.g. trimethylbenzylammonium chloride. It is also possible to use phosphines such as, for example, triphenylphosphine, as curing catalysts. Suitable catalysts are also described in, for example, J. Bielemann, Lackadditive, Wiley-VCH Verlag GmbH, Weinheim, 1998, pages 244-247. Examples are carboxylic acids such as, for example, p-toluenesulfonic acid, dodecylbenzenesulfonic acid, dinonylnaphthalenesulfonic acid and dinonylnaphthalenedisulfonic acid. There may also be used, for example, latent or blocked sulfonic acids, it being possible for the blocking of the acid to be ionic or non-ionic.

Such catalysts are used in concentrations customary in the art and known to the skilled person.

In order to accelerate photopolymerisation, amines may be added as further additives (d), especially tertiary amines, e.g. tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 18-diazabicyclo[5.4.0]undec-7-ene (DBU), 1,5-diazabicyclo[4.3.0]non-5-ene (DBN) and salts thereof. Further examples are quaternary ammonium salts, e.g. trimethylbenzylammonium chloride. The action of the amines may be reinforced by adding aromatic ketones of the benzophenone type. Amines that are suitable as oxygen capture agents are, for example, N,N-dialkylanilines as described in EP339841. Further accelerators, coinitiators and autooxidisers are thiols, thioethers, disulfides and phosphines as described in, for example, EP438123 and GB2180358.

It is also possible for chain transfer reagents customary in the art to be added to the compositions according to the invention. Examples are mercaptans, amines and benzothiazole.

Photopolymerisation can also be accelerated by addition, as further additives (d), of photosensitisers, which shift or broaden the spectral sensitivity. These include especially aromatic carbonyl compounds such as, for example, benzophenone derivatives, thioxanthone derivatives, including especially isopropyl thioxanthone, anthraquinone derivatives and 3-acylcoumarin derivatives, terphenyls, styryl ketones, and 3-(aroylmethylene)-thiazolines, camphorquinone and also eosin, rhodamine and erythrosine dyes.

The amines mentioned above, for example, may also be regarded as photosensitisers. Examples of suitable sensitizer compounds (d) are disclosed in WO06/008251, page 36, line 30 to page 38, line 8, the disclosure of which is hereby incorporated by reference. Subject of the invention therefore also is a photopolymerizable composition as described above, as further additive (d) comprising a photosensitizer.

The curing process, especially of pigmented (e.g. pigmented with titanium dioxide) compositions, can also be assisted by adding an additional additive (d) which under thermal conditions is a free-radical-forming component, for example an azo compound, e.g. 2,2'-azobis(4-methoxy-2,4-dimethylvaleronitrile), a triazene, a diazo sulfide, a pentazadiene or a peroxy compound such as a hydroperoxide or peroxycarbonate, e.g. tert-butyl hydroperoxide as described in, for example, EP245639.

Further customary additives (d) are—depending on the intended use—fluorescent whitening agents, fillers, e.g. kaolin, talc, barite, gypsum, chalk or silicate-type fillers, wetting agents or flow improvers.

For curing thick and pigmented coatings, the addition of glass microspheres or powdered glass fibres is suitable, as described in, for example, U.S. Pat. No. 5,013,768.

The formulations may also comprise dyes and/or white or coloured pigments [as further additive (d)]. Depending on the intended use, both inorganic and organic pigments may be used. Such additives will be known to the person skilled in the art; a few examples are titanium dioxide pigments, e.g. of the rutile or anatase type, carbon black, zinc oxide, e.g. zinc white, iron oxides, e.g. iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments.

The pigments may be used in the formulations singly or in admixture.

The pigments are added to the formulations, in accordance with the intended use, in amounts customary in the art, for example in an amount of from 1 to 60% by weight, or from 10 to 30% by weight, based on the total mass.

The formulations may also comprise, for example, organic dyes from a very wide variety of classes. Examples are azo dyes, methine dyes, anthraquinone dyes or metal complex dyes. Customary concentrations are, for example, from 0.1 to 20%, especially from 1 to 5%, based on the total mass.

Selection of the additives is based on the particular field of use of the photopolymerizable composition and the properties desired in that field.

Subject of the invention also is a photopolymerizable composition as described above as further additive (d) comprising a pigment or dye or a mixture of pigments or dyes.

Subject of the invention also is a photopolymerizable composition as described above as further additive (d) comprising a pigment or a mixture of pigments or a mixture of one or more pigments with one or more dyes.

Subject of the invention also is a photopolymerizable composition as described above as further additive (d) comprising a dispersant or a mixture of dispersants.

The additives (d) described hereinbefore are customary in the art and are accordingly used in amounts customary in the art.

It is, of course, possible to use mixtures of the compound of the invention with known photoinitiators (c), for example mixtures with camphor quinone; benzophenone, benzophenone derivatives, such as 2,4,6-trimethylbenzophenone, 2-methylbenzophenone, 3-methylbenzophenone, 4-methylbenzophenone, 2-methoxycarbonylbenzophenone 4,4'-bis (chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoylbenzoate, 3-methyl-4'-phenylbenzophenone, 2,4,6-trimethyl-4'-phenylbenzophenone, 4,4'-bis (dimethylamino)benzophenone, 4,4'-bis(diethylamino) benzophenone; ketal compounds, as for example benzildimethylketal; acetophenone, acetophenone derivatives, for example α-hydroxycycloalkyl phenyl ketones or α-hydroxyalkyl phenyl ketones, such as for example 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl) phenoxy]-phenyl}-2-methyl-propan-1-one; oligomeric α-hydroxy ketones; dialkoxyacetophenones, α-hydroxy- or α-aminoacetophenones, e.g. (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyi)aminobenzoyl)-1-benzyl-1-dimethylaminopropane), (3,4-dimethoxybenzoyl)1-benzyl-1-dimethylaminopropane; 4-aroyl-1,3-dioxolanes, benzoin alkyl ethers and benzil ketals, e.g. dimethyl benzil ketal, phenylglyoxalic esters and derivatives thereof, e.g. methyl α-oxo benzeneacetate, oxo-phenyl-acetic acid 2-(2-hydroxy-ethoxy)-ethyl ester, dimeric phenylglyoxalic esters, e.g. oxo-phenyl-acetic acid 1-methyl-2-[2-(2-oxo-2-phenyl-acetoxy)-propoxy]-ethyl ester; oximeesters, e.g. 1,2-octanedione 1-[4-(phenylthio)phenyl]-2-(O-benzoyloxime), ethanone 1-[9-ethyl-6-(2-methylbenzoyl)-9H-carbazol-3-yl]-1-(O-acetyloxime), 9H-thioxanthene-2-carboxaldehyde 9-oxo-2-(O-acetyloxime), or for example a combination of oxime esters with ca-amino ketones, e.g. a combination of (4-morpholinobenzoyl)-1-benzyl-1-dimethylaminopropane with [4-(2-methylphenylcarboxy)phenyl]-bis[4-(O-acetyloximine)phenyl]amine; peresters, e.g. benzophenone tetracarboxylic peresters as described for example in EP126541, monoacyl phosphine oxides, e.g. (2,4,6-trimethylbenzoyl)diphenylphosphine oxide, ethyl (2,4,6-trimethylbenzoyl phenyl) phosphinic acid ester; bisacylphosphine oxides, e.g. bis(2,6-dimethoxy-benzoyl)-(2,4,4-trimethylpentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, hexaaryl-bisimidazole/coinitiator systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl)titanium. Further, borate compounds can be used as coinitiators.

Mixtures of the compounds of the invention with known photoinitiators (c) are especially attractive, if the mixture of the compound of the invention with the photoinitiator(s) is a liquid, since such liquids can easily be handled and incorporated into the formulation. Especially attractive are mixtures where either the compound of the invention or the photoinitiator (c) are liquids, since this allows the compounds to be mixed over a large ratio. Most preferred are mixtures where both the compound of the invention and the photoinitiator (c) are liquids, since this allows the components to mixed in any ratio.

Many of said additional photoinitiators (c) are commercially available, for example under the tradenames Darocur® and Irgacure® from BASF SE.

Subject of the invention accordingly also is a photopolymerizable composition as described above, wherein the additional photoinitiator (c) is selected from the group consisting of alpha-hydroxy ketones, benzophenone, substituted benzophenone compounds, benzildimethylketal, phenylglyoxylate compounds and alpha-amino ketone compounds.

Preferably the additional photoinitiator (c) is selected from the group consisting of benzophenone, 2,4,6-trimethylbenzophenone, 2-methylbenzophenone, 3-methylbenzophenone, 4-methylbenzophenone, 2-methoxycarbonylbenzophenone 4,4'-bis(chloromethyl)benzophenone, 4-chlorobenzophenone, 4-phenylbenzophenone, 3,3'-dimethyl-4-methoxy-benzophenone, [4-(4-methylphenylthio) phenyl]-phenylmethanone, methyl-2-benzoylbenzoate, 3-methyl-4'-phenylbenzophenone, 2,4,6-trimethyl-4'-phenylbenzophenone, 4,4'-bis(dimethylamino)benzophenone, 4,4'-bis(diethylamino)benzophenone, benzildimethylketal, acetophenone, 2-hydroxy-2-methyl-1-phenyl-propanone, 1-hydroxy-cyclohexyl-phenyl-ketone, 1-(4-dodecylbenzoyl)-1-hydroxy-1-methyl-ethane, 1-(4-isopropylbenzoyl)-1-hydroxy-1-methyl-ethane, 1-[4-(2-hydroxyethoxy)-phenyl]-2-hydroxy-2-methyl-1-propan-1-one; 2-hydroxy-1-{4-[4-(2-hydroxy-2-methyl-propionyl)-benzyl]-phenyl}-2-methyl-propan-1-one; 2-hydroxy-1-{4-[4-(2-hydroxy-2-methyl-propionyl)phenoxy]-phenyl}-2-methyl-propan-1-one, (4-methylthiobenzoyl)-1-methyl-1-morpholinoethane, (4-morpholinobenzoyl)-1-benzyl-1-dimethylaminopropane, (4-morpholinobenzoyl)-1-(4-methylbenzyl)-1-dimethylaminopropane, (4-(2-hydroxyethyl)aminobenzoyl)-1-benzyl-1-dimethylaminopropane), (3,4-dimethoxybenzoyl)-1-benzyl-1-dimethylaminopropane, methyl c-oxo benzeneacetate, oxo-phenyl-acetic acid 2-(2-hydroxy-ethoxy)-ethyl ester and oxo-phenyl-acetic acid 1-methyl-2-[2-(2-oxo-2-phenyl-acetoxy)propoxy]-ethyl ester, Esacure®KIP150.

Further preferred examples of additional photoinitiators (c) are selected from the group consisiting of 2-hydroxy-2-methyl-1-phenyl-propanone, 1-hydroxy-cyclohexyl-phenyl-ketone, 2-hydroxy-1-{4-[4-(2-hydroxy-2-methyl-propionyl)-benzyl]-phenyl}-2-methyl-propan-1-one, Esacure KIP® 150, methyl a-oxo benzeneacetate, oxo-phenyl-acetic acid 2-(2-hydroxy-ethoxy)-ethyl ester and oxo-phenyl-acetic acid 1-methyl-2-[2-(2-oxo-2-phenyl-acetoxy)-propoxy]-ethyl ester.

In particular preferred additional photoinitiators (c) are selected from the group consisting of 2-hydroxy-2-methyl-1-phenyl-propanone, 1-hydroxy-cyclohexyl-phenyl-ketone and 2-hydroxy-1-{4-[4-(2-hydroxy-2-methyl-propionyl)-benzyl]-phenyl}-2-methyl-propan-1-one.

The photopolymerizable composition as described above for example comprises 0.05 to 15% by weight, preferably 0.1 to 5% by weight, of the photoinitiator (b) or the photoinitiators (b)+(c), based on the composition.

The compositions according to the invention can be used for various purposes, for example in overprint coatings, as printing ink, e.g. screen printing ink, ink for offset- or flexo printing, inkjet ink, ink for sheet-fed printing, electrophotography ink, intaglio ink, as clearcoats, white coats or colour-pigmented coats, e.g. for wood or metal, as powder coatings, as paints, inter alia for paper, wood, metal or plastics, as daylight-curable paints for marking structures and roads, paints for buildings, constructions, vehicles, aircraft, etc., for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as etch resists or permanent resists, both liquid and dry films, as photostructurable dielectrics, and as solder masks for electronic circuits, as resists in the production of colour filters for any type of display screen or in the creation of structures during the manufacture of plasma displays and electroluminescent displays, in the production of optical switches, optical gratings (interference gratings), in the manufacture of three-dimensional articles by curing in the mass (UV curing in transparent moulds) or according to the stereolithography process, as described in, for example, U.S. Pat. No. 4,575,330, in the manufacture of composite materials (e.g. styrene polyesters which may include glass fibres and/or other fibres and other adjuvants) of gel coats and thick-layered compositions, in the coating or sealing of electronic components or as coatings for optical fibres. The compositions are also suitable for the production of optical lenses, e.g. contact lenses or Fresnel lenses, and also in the manufacture of medical apparatus, aids or implants. The compositions can also be used for the preparation of gels having thermotropic properties. Such gels are described in, for example, DE19700064 and EP678534.

Photocuring further is of great importance for printing applications, since the drying time of the ink is a critical factor for the production rate of graphic products, and should be in the order of fractions of seconds. UV-curable inks are particularly important for screen printing, offset inks, ink-jet inks, flexographic printing inks, intaglio inks, electrophotographic inks, sheetfed inks, overprint varnishes or primers.

As already mentioned above, the photoinitiator is suitable also for producing printing plates e.g. flexo printing plates or offset printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions.

Printing inks are known to the person skilled in the art, are used widely in the art and are described in the literature.

They are, for example, pigmented printing inks and printing inks coloured with dyes.

A printing ink is, for example, a liquid or paste-form dispersion that comprises colorants (pigments or dyes), binders and also optionally solvents and/or optionally water and additives. In a liquid printing ink, the binder and, if applicable, the additives are generally dissolved in a solvent. Customary viscosities in the Brookfield viscometer are, for example, from 20 to 5000 mPa·s, for example from 20 to 1000 mPa·s, for liquid printing inks. For paste-form printing inks, the values range, for example, from 1 to 100 Pa·s, preferably from 5 to 50 Pa·s. The person skilled in the art will be familiar with the ingredients and compositions of printing inks.

Suitable pigments, like the printing ink formulations customary in the art, are generally known and widely described.

Printing inks comprise pigments advantageously in a concentration of, for example, from 0.01 to 40% by weight, preferably from 1 to 25% by weight, especially from 5 to 15% by weight, based on the total weight of the printing ink.

The printing inks can be used, for example, for intaglio printing, gravure printing, flexographic printing, screen printing, offset printing, lithography or continuous or dropwise ink-jet printing on material pretreated in accordance with the process of the invention using generally known formulations, for example in publishing, packaging or shipping, in logistics, in advertising, in security printing or in the field of office equipment.

Suitable printing inks are both solvent-based printing inks and water-based printing inks. Of interest are, for example, printing inks based on aqueous acrylate. Such inks are to be understood as including polymers or copolymers that are obtained by polymerisation of at least one monomer containing a group

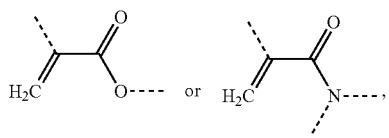

and that are dissolved in water or a water-containing organic solvent. Suitable organic solvents are water-miscible solvents customarily used by the person skilled in the art, for example alcohols, such as methanol, ethanol and isomers of propanol, butanol and pentanol, ethylene glycol and ethers thereof, such as ethylene glycol methyl ether and ethylene glycol ethyl ether, and ketones, such as acetone, ethyl methyl ketone or cyclo, for example isopropanol. Water and alcohols are preferred.

Suitable printing inks comprise, for example, as binder primarily an acrylate polymer or copolymer and the solvent is selected, for example, from the group consisting of water, $C_1$-$C_5$alcohols, ethylene glycol, 2-($C_1$-$C_5$alkoxy)-ethanol, acetone, ethyl methyl ketone and any mixtures thereof.

In addition to the binder, the printing inks may also comprise customary additives known to the person skilled in the art in customary concentrations.

For intaglio or flexographic printing, a printing ink is usually prepared by dilution of a printing ink concentrate and can then be used in accordance with methods known per e.

The printing inks may, for example, also comprise alkyd systems that dry oxidatively.

The printing inks are dried in a known manner customary in the art, optionally with heating of the coating.

A suitable aqueous printing ink composition comprises, for example, a pigment or a combination of pigments, a dispersant and a binder.

Subject of the invention therefore also is a photopolymerizable composition as described above as further additive (d) comprising a dispersant or a mixture of dispersants.

Dispersants that come into consideration include, for example, customary dispersants, such as water-soluble dispersants based on one or more arylsulfonic acid/formaldehyde condensation products or on one or more water-soluble oxalkylated phenols, non-ionic dispersants or polymeric acids. Such dispersants are known and are described, for example, in U.S. Pat. No. 5,186,846 and DE19727767. Suitable oxalkylated phenols are likewise known and are described, for example, in U.S. Pat. No. 4,218,218 and DE19727767. Suitable non-ionic dispersants are, for example, alkylene oxide adducts, polymerisation products of vinylpyrrolidone, vinyl acetate or vinyl alcohol and co- or ter-polymers of vinyl pyrrolidone with vinyl acetate and/or vinyl alcohol.

It is also possible, for example, to use polymeric acids which act both as dispersants and as binders.

Examples of suitable binder components that may be mentioned include (meth)-acrylategroup-containing, vinyl-group-containing and/or, depending on the intended application, epoxy-group-containing monomers, prepolymers and polymers and mixtures thereof. Further examples are melamine acrylates and silicone acrylates. The acrylate compounds may also be non-ionically modified (e.g. provided with amino groups) or ionically modified (e.g. provided with acid groups or ammonium groups) and used in the form of aqueous dispersions or emulsions (e.g. EP704469, EP012339). Furthermore, in order to obtain the desired viscosity the solventless acrylate polymers can be mixed with so-called reactive diluents, for example vinyl-group-containing monomers. Further suitable binder components are epoxy-group-containing compounds.

The printing ink compositions may also comprise as additional component, for example, an agent having a water-retaining action (humectant), e.g. polyhydric alcohols, polyalkylene glycols, which renders the compositions especially suitable for ink-jet printing.

It will be understood that the printing inks may comprise further auxiliaries, such as are customary especially for (aqueous) ink-jet inks and in the printing and coating industries, for example preservatives (such as glutardialdehyde and/or tetramethylolacetyleneurea, anti-oxidants, degassers/defoamers, viscosity regulators, flow improvers, anti-settling agents, gloss improvers, lubricants, adhesion promoters, anti-skin agents, matting agents, emulsifiers, stabilisers, hydrophobic agents, light stabilisers, handle improvers and anti-statics. When such agents are present in the compositions, their total amount is generally ≤1% by weight, based on the weight of the preparation.

Printing inks include, for example, those comprising a dye (with a total content of dyes of e.g. from 1 to 35% by weight, based on the total weight of the ink). Dyes suitable for colouring such printing inks are known to the person skilled in the art and are widely available commercially, e.g. from BASF SE.

Such printing inks may comprise organic solvents, e.g. water-miscible organic solvents, for example $C_1$-$C_4$alcohols, amides, ketones or ketone alcohols, ethers, nitrogen-containing heterocyclic compounds, polyalkylene glycols, $C_2$-$C_6$alkylene glycols and thioglycols, further polyols, e.g. glycerol and $C_1$-$C_4$alkyl ethers of polyhydric alcohols, usually in an amount of from 2 to 30% by weight, based on the total weight of the printing ink.

The printing inks may also, for example, comprise solubilisers, e.g. $\in$-caprolactam.

The printing inks may, inter alia for the purpose of adjusting the viscosity, comprise thickeners of natural or synthetic origin. Examples of thickeners include commercially available alginate thickeners, starch ethers or locust bean flour ethers. The printing inks comprise such thickeners e.g. in an amount of from 0.01 to 2% by weight, based on the total weight of the printing ink.

It is also possible for the printing inks to comprise buffer substances, for example borax, borate, phosphate, polyphosphate or citrate, in amounts of e.g. from 0.1 to 3% by weight, in order to establish a pH value of e.g. from 4 to 9, especially from 5 to 8.5.

As further additives, such printing inks may comprise surfactants or humectants. Surfactants that come into consideration include commercially available anionic and non-ionic surfactants. Humectants that come into consideration include, for example, urea or a mixture of sodium lactate (advantageously in the form of a 50 to 60% aqueous solution) and glycerol and/or propylene glycol in amounts of e.g. from 0.1 to 30% by weight, especially from 2 to 30% by weight, in the printing inks.

Furthermore, the printing inks may also comprise customary additives, for example foam-reducing agents or especially substances that inhibit the growth of fungi and/or bacteria. Such additives are usually used in amounts of from 0.01 to 1% by weight, based on the total weight of the printing ink.

The printing inks may also be prepared in customary manner by mixing the individual components together, for example in the desired amount of water.

As already mentioned, depending upon the nature of the use, it may be necessary for e.g. the viscosity or other physical properties of the printing ink, especially those properties which influence the affinity of the printing ink for the substrate in question, to be adapted accordingly.

The printing inks are also suitable, for example, for use in recording systems of the kind in which a printing ink is expressed from a small opening in the form of droplets which are directed towards a substrate on which an image is formed.

Suitable substrates are, for example, textile fibre materials, paper, plastics or aluminium foils pretreated by the process according to the invention. Suitable recording systems are e.g. commercially available ink-jet printers.

Preference is given to printing processes in which aqueous printing inks are used.

Preferred in ink-jet ink formulations comprise (meth)acrylated epoxy esters; (meth)acrylated polyesters or vinyl-ether-group-containing polyesters, (meth)acrylated polyurethanes, polyethers and polyols.

A preferred component used in UV-curable inkjet are acrylates which have been modified by reaction with primary or secondary amines, as described, for example, in U.S. Pat. No. 3,844,916, EP280222, U.S. Pat. No. 5,482,649 or U.S. Pat. No. 5,734,002. Such amine-modified acrylates are also termed aminoacrylates. Examples are already given hereinbefore. It is known that in the presence of aminoacrylates UV-curable systems show an increased curing performance. They are useful to overcome the oxygen inhibition typically observed for radical induced polymerization reactions, especially for low viscous systems like UV-curable inkjet.

It will be clear that mixtures of all these cited monomers, prepolymers, polymers and oligomers can be used in the ink compositions comprising the photoinitiator according to the present invention.

The amount of the photopolymerizable monomer, oligomer or prepolymer in this connection is for example 10 to 80 wt %, preferably 10 to 60 wt %.

The inks comprising the photoinitiator of the present invention may besides to radically polymerizable components also comprise cationic-curable compositions having a low viscosity which comprise at least one aliphatic or aromatic epoxide, at least one polyol or polyvinyl polyols as mentioned above, and at least one cation-generating photoinitiator. A number of these epoxides are well known in the art and are commercially available. Photoinitiators that can be used in the cationic photocurable compositions are, for example, aryl iodonium salts and aryl sulfonium salts.

Emphasized are such hybrid systems that contain cationically and radically polymerisable and photopolymerisable raw materials. Examples of cationically polymerisable systems include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. Radiation curable resins contain ethylenically unsaturated compounds, especially (meth)acrylate resins. Examples are also as given above.

Furthermore interesting are hybrid systems that are photopolymerized in a first stage and then crosslinked through thermal post-treatment in a second stage or vice versa. Such hybrid systems comprise an unsaturated compound in admixture with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins.

Other compositions suitable as for example ink-jet inks are dual cure compositions, which are cured first by heat and subsequently by UV or electron irradiation, or vice versa, and whose components contain ethylenic double bonds as described above capable to react on irradiation with UV light in presence of a photoinitiator, in the context of the invention the photoinitiator as described above.

Ink jet inks for example contain a colorant. A wide variety of organic and inorganic dyes and pigments, alone or in combination may be selected for use in ink jet ink compositions; the person skilled in the art is familiar with the appropriate choice. The pigment particles should be sufficiently small (0.005 to 15 μm) to permit free flow of the ink at the ejecting nozzles. The pigment particles should preferably be 0.005 to 1 μm.

Very fine dispersions of pigments and their preparation are disclosed in e.g. U.S. Pat. No. 5,538,548. The inks preferably comprise a total content of colorant of 1 to 35% by weight, in particular 1 to 30% by weight, and preferably 1 to 20% by weight, based on the total weight of ink. A limit of 2.5% by weight, in particular 5% by weight, and preferably 7.5% by weight, is preferred here as the lower limit.

Suitable colorants are for example pure pigment powders such as Cyan IRGALITE® Blue GLO (BASF SE) or pigment preparations such as MICROLITH-pigment preparations.

Ink jet inks may include a variety of further additives such as for example surfactants, biocides, buffering agents, anti-mould agents, pH adjustment agents, electric conductivity adjustment agents, chelating agents, anti-rusting agents, polymerisation inhibitors, light stabilizers, and the like. Such additives may be included in the ink jet inks in any effective amount, as desired.

A preferred field of use comprises overprint coatings and also pigmented thin coatings (layer thickness <20 μm), for example printing inks that are used in printing methods such as, for example, flexographic printing, offset printing, screen printing, intaglio printing, gravure printing, letterpress printing, tampon printing and inkjet printing.

Overprint coatings typically comprise ethylenically unsaturated compounds such as oligomeric and/or monomeric acrylates. Amine acrylates may also be included.

As mentioned hereinbefore, the overprint coatings and printing inks may also comprise further photoinitiators and coinitiators.

Subject of the invention therefore also is a photopolymerizable composition as described above, which is a printing ink, in particular an offset printing ink.

The photoinitiators of the present invention are also suitable for use in UV-curable adhesives; e.g. in the preparation of pressure-sensitive adhesives, laminating adhesives, hot-melt adhesives, moisture-cure adhesives, silane reactive adhesives or silane reactive sealants and the like, and related applications. Said adhesives can be hot melt adhesives as well waterborne or solvent borne adhesives, liquid solventless adhesives or 2-part reactive adhesives. In particular suitable are pressure-sensitive adhesives (PSA), for example uv-curable hot melt pressure sensitive adhesives. Said adhesives for example comprise at least one rubber component, at least one resin component as tackyfier and at least one oil component, for example in the weight ratio 30:50:20. Suitable tackyfiers are natural or synthetic resins. The person skilled in the art is aware of suitable corresponding compounds as well as of suitable oil components or rubbers.

The pre-polymerized adhesives containing the isocyanates, for example in blocked form, can for example be processed at high temperature and coated onto the substrate following the hotmelt process, afterwards full cure is achieved by an additional curing step involving the blocked isocyanates, which is realized by photoactivation of the photolatent catalyst.

The photoinitiators according to the invention may also be used as initiators for emulsion, bead or suspension polymerisation processes or as initiators of polymerisation for the fixing of orientation states of liquid-crystalline monomers and oligomers, or as initiators for the fixing of dyes on organic materials.

The photoinitiators according to the invention may also be used as free-radical photoinitiators or photoinitiating systems for radiation-curable powder coatings. The powder coatings may be based on solid resins and monomers containing reactive double bonds, for example maleates, fumarates, vinyl ethers, (meth)acrylates, (meth)acrylamides and mixtures thereof. A free-radical UV-curable powder coating may be formulated by mixing unsaturated polyester resins with solid acrylamides (e.g. methylacrylamido-glycolate methyl ester) and a free-radical photoinitiator according to the invention, for example as described in the lecture "Radiation Curing of Powder Coating", Conference Proceedings, Radtech Europe 1993 by M. Wittig and Th. Gohmann. Free-radical UV-curable power coatings may also be formulated by mixing unsaturated polyester resins with solid acrylates, methacrylates or vinyl ethers and a photoinitiator according to the invention. The powder coatings may also comprise binders, as described in, for example, DE4228514 and EP636669. The powder coating formulations described in EP636669 comprise, for example, 1) an unsaturated resin from the group of (semi-)crystalline or amorphous unsaturated polyesters, unsaturated polyacrylates or mixtures thereof with unsaturated polyesters, with special preference being given to those derived from maleic acid or fumaric acid; 2) an oligomeric or polymeric cross-linking agent containing vinyl ether-, vinyl ester- or (meth)acrylate-functional groups, with special preference being given to vinyl ether oligomers, for example divinyl ether-functionalised urethanes; 3) the photoinitiator.

The UV-curable powder coatings may also comprise white or coloured pigments. Accordingly, for example, there may preferably be used rutile titanium dioxide in concentrations of up to 50% by weight in order to obtain a cured powder coating with good hiding power. The process normally comprises electrostatic or tribostatic spraying of the powder onto the substrate, e.g. metal or wood, melting of the powder as a result of heating and, after a smooth film has been formed, radiation-curing of the coating using ultraviolet and/or visible light, for example using medium-pressure mercury lamps, metal halide lamps or xenon lamps. A particular advantage of radiation-curable powder coatings compared to corresponding thermally curable coatings is that the flow time after melting of the powder particles can be extended as desired in order to ensure the formation of a smooth high-gloss coating. In contrast to thermally curable systems, radiation-curable powder coatings can be formulated so that they melt at relatively low temperatures, without the undesirable effect of a reduction in shelf-life. For that reason they are also suitable as coatings for heat-sensitive substrates, for example wood or plastics. However, if the powder coatings are to be applied to non-heat-sensitive substrates, for example metals (vehicle coatings), it is also possible to make available "dual cure" powder coating formulations using the photoinitiators according to the invention. Such formulations will be known to the person skilled in the art; they are cured both thermally and also by means of UV and can be found in, for example, U.S. Pat. No. 5,922,473.

The photoinitiator according to the invention may also be used in the form of an aqueous, for example 0.5-5%, preferably 0.5-2%, dispersion in polymer dispersions, for example in aqueous polyurethane dispersions, so-called PUDs.

The photocurable compositions according to the invention are suitable, for example, as coating substances for substrates of all kinds, e.g. wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which a protective layer or, by means of image-wise exposure, an image is to be applied.

The substrates can be coated by applying a liquid composition, a solution or a suspension or a powder to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents are, for example, ketones, ethers and esters, e.g. methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by printing methods such as flexography printing, lithography printing, inkjet, screen printing, spin-coating, immersion, roller application, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Ed., Vol. A18, pp. 491-500.

The amount applied (layer thickness) and the nature of the substrate (layer support) are dependent on the desired field of use.

A further field of use comprises compositions that are suitable for the coating of glass fibres, both for the inner and also for the middle and outer layers (optical fibre coating, OPC). The coated glass fibres may also be gathered into bundles giving a further coating. Such coating layers comprise UV-curable oligomers, UV-curable monomers and also at least one photoinitiator and additives.

Any UV-curable oligomer is suitable for the coating of glass fibres.

Further fields of use of photocuring are metal coating, for example the application of a finish to sheet metals and tubes, cans or bottle closures, and also photocuring on plastics coatings, for example PVC-based floor or wall coverings.

Examples of the photocuring of paper coatings are the application of a colourless finish to labels, packaging materials or book covers.

The photosensitivity of the compositions according to the invention usually extends from approximately 150 nm into the IR range. Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium-pressure, high-pressure and low-pressure mercury radiators doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED, OLED), electron beams and X-rays. The distance between the lamp and the substrate to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible and infrared or NIR range may also be used.

As already mentioned, curing according to the invention can be carried out solely by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a heating plate or by irradiation with IR lamps. Unassisted curing at room temperature is also possible, depending on the binder system used. The curing temperatures are generally between room temperature and 150° C., for example from 25 to 150° C. or from 50 to 150° C. In the case of powder coatings or coil coatings, the curing temperatures may be even higher, e.g. up to 350° C.

The invention relates to the use of the photoinitiators as described above as photoinitiators for the photopolymerization of compounds containing ethylenically unsaturated double bonds and to a process for the photopolymerization of compounds containing ethylenically unsaturated double bonds, which comprises irradiating a photopolymerizable composition as defined above with electromagnetic radiation in the range from 150 to 600 nm, or with electron beam or with X-rays.

Interesting is the use of the composition as described above for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; in particular the use of a photopolymerizable composition as described above for producing pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

The photoinitiator according to the invention, or blends of the photoinitiators according to the invention with other photoinitiators, may also be used as free-radical photoinitiators or photoinitiating systems in formulations used for rapid prototyping or additive manufacturing processes based on photolithographic techniques.

Such processes are well-known to the one skilled in the art and include for example stereolithography using a moving laser (SLA process), digital light processing (DLP) or large area maskless photopolymerization (LAMP). Common to all these techniques is the stepwise build-up of three-dimensional objects by a layer-by-layer image-wise curing process using one of the aforementioned techniques, followed by the removal of uncured material by a suitable washing or development process. The image-wise curing process can be combined with a full-exposure irradiation step, or with a thermal curing process, in order to achieve the desired final properties. The aforementioned post curing processes are subsequently applied, preferably minutes to few hours after completion of the preceding layer wise form giving process. In the irradiation step various light sources, e.g. mercury lamps, xenon and fluorescent lamps or light emitting diodes (LEDs) may be used.

It is also possible to combine the radically curing material with a second material curing by an alternative mechanism. An example is the combination of the radically curing formulation with a cationically curing material. For example, acrylate moieties contained in a formulation are preferably polymerized using radical initiators, whereas the polymerization of epoxy moieties is preferably triggered by cationic initiators. Both processes can be applied simultaneously or can be combined in a subsequent manner.

Alternatively rapid prototyping or additive manufacturing can also be performed using 3D printing respectively polyjetting technologies. Corresponding equipment is commercially available from e.g. 3D Systems Inc. under their ProJet™ brand or from Stratasys offering their PolyJet 3D printers under their brands Dimension, Connex, Eden and Pro. These examples are intended for reference only, but should not limit the scope of the invention to related 3D printing technologies. In these technologies the three-dimensional objects are build-up by layer-by-layer jetting of the photocurable material, followed by immediate curing using a suitable radiation source. Suitable radiation sources are for example irradiation systems commonly used in radiation curing, such as mercury lamps, doped mercury lamps, electrodeless lamps and the like, or LED lamps of suitable wavelengths.

In these rapid prototyping or additive manufacturing applications, the photoinitiators according to the invention can be used in the photopolymer material used for the production of the three-dimensional object, or in the support material used as an intermediate support for the build-up of three-dimensional structures. The support material is designed in a way that it can easily be removed after the build-up of the three-dimensional object without affecting the latter, e.g. by a suitable washing or development process.

The photoinitiators according to the invention, or blends of the photoinitiators according to the invention with other photoinitiators, may also be used as free-radical photoinitiators or photoinitiating systems in formulations used for applications using LED (light-emitting diode) light sources for curing. LED lights sources find for example use for the curing of UV inkjet inks, for example in high-speed single pass applications, sheetfed applications, narrow web applications, flat bed application, or wide format applications. Especially designed LED curable inks are also used in prototyping or additive manufacturing processes using the photopolymer jetting technology. LED light sources are also used in industrial applications, such as e.g. wood coatings or optical fibre coatings (OFC). Other applications using LED light sources are field applications, such as repair applications, e.g. automotive or industrial repair coatings, or construction side applications such as flooring applications. Other applications are adhesives both for professional and do-it-yourself applications. Still other applications are found in light curable nail polishes and the like.

LED light sources emitting at different wavelengths extending form the visible to the short UV are available. However in view of the price/performance level of the different LED diodes and process safety considerations, LED emitting in the visible or UV-A are preferred. LED light sources emitting in the visible, for example at 470 nm, are especially preferred for dental or medical applications. LED light sources emitting in the visible or UV-A range, for example at 405 nm, 395 nm, 385 nm or 365 nm are preferred for technical applications. Especially preferred are LEDs emitting at 405 nm, 395 nm or 385 nm. Since the liquid photoinitiator mixtures according to the invention have good absorption in this range and undergo a photobleaching process, they are especially suited for use in such applications.

When using LED light sources for curing, it can be advantageous to use the photoinitiator mixtures according to the invention in combination with another photoinitiator compound (C). Preferred is the combination with (substituted) benzophenone derivatives, phenyl glyoxylate derivatives or thioxanthone derivatives. Especially preferred is the combination of liquid photoinitiator mixtures according to the invention with thioxanthone derivatives.

The invention also relates to the use of the photoinitiators as described above as photolatent reducing agents for the reduction of metal cations to metal cations of a lower oxidation state, or to metals in the form of metal nanoparticles or metal patterns. Photochemical routes for the reduction of metal salts, for example Ag+ or $Au^{3+}$ salts (Scaiano et al., *Pure App. Chem* 2009, 81, 635) or $Cu^{2+}$ salts (Paconi et al. *Photochem. Photobiol Sci.* 2010, 9 766; Zhu et al, *Langmuir* 2012, 28, 14461) have been reported in the literature and are of high interest for example for the imagewise preparation of nanostructures containing metal nanoparticles. The selective photoinduced reduction of $Cu^{2+}$ to $Cu^+$ has also been reported (Adzima et al. *Nat. Chem.* 2011, 3, 256). The photochemically generated $Cu^+$ is useful for example as catalyst for the copper(I)-catalyzed azide-alkyne cycloaddition reaction ("click reaction"), or as catalyst for the atom transfer radical polymerization (ATRP), allowing to apply the advantages of the spatiotemporal control of a light-induced reaction to these processes.

The metal cations to be reduced are usually used in form of a corresponding salt, for example a silver halide or triflate, a copper(II) sulfate salt or $HAuCl_4$. These salts are soluble in polar solvents or water. Thus photoinitiators with sufficient solubility in a polar, or even aqueous environment, are required. Since the photoinduced reduction is often performed in a matrix material absorbing light of shorter wavelengths, or in the presence of photolabile compounds such as azides in the case of the "click reaction", photoinitiators absorbing in the UV-A or visible range are preferred.

Thus, especially suitable for these applications are the photoinitiators of structure (II) of the present invention, which are soluble in polar solvents or water and absorb light in the UV-A and visible range. In a special form of this application, especially preferred are photoinitiator of structures (II) where the cation $Q^{m+}$ itself is a cation of the metal to be reduced. Examples are the monovalent (m=1) photoinitiators of structure (II) with $Q^{m+}$ being $Ag^*$, divalent (m=2) photoinitiators of structure (II) with $Q^{m+}$ being $Cu^{2+}$, or trivalent (m=3) photoinitiators of structure (II) with $Q^{m+}$ being $Au^{3+}$.

If the metal cation to be reduced has an oxidation state of +1, such as for example $Ag^+$, the result of the photoinduced reduction is the metal, such as for example {Ag}. If the metal to be reduced has an oxidation state higher than +1, for example $Cu^{+2}$, the result of the photoinduced reduction is, depending on the reduction conditions, a metal cation of a lower oxidation state, for example $Cu^+$, or the metal, for example {Cu(0)}. It is possible to control the reduction by the stoichiometry of the added photocatalyst, or by addition of certain complexing agents such as amines or polyvinylpyrrolidone (PVP).

The use of a photoinduced reduction of $Cu^{2+}$ to $Cu^{1+}$ as a photolatent trigger of copper(I) catalysed crosslinking reactions or polymerization reactions has been reported. Photogenerated $Cu^{1+}$ can be used to catalyse the cycloaddition of alkyne groups to azide groups known as a "click" reaction. In this reaction sequence it is of outermost importance to activate the copper reduction process at the longest wavelengths possible, in order to avoid photochemical decomposition of the azide groups. This has been achieved in the literature using monoacylphosphine oxide photoinitiators. It is obvious that with the new bisacylphosphine oxide type compounds of the present invention, a better separation of the two photochemical processes can be achieved, since the bisacylphosphine oxide of the present invention absorb light of longer wavelengths than the monoacylphosphine oxide. Thus the copper reduction can be initiated with visible light of longer wavelengths, which does not affect the azide groups absorbing in the UV only. As a consequence a cleaner and more efficient crosslinking is achieved using the new photocatalysts of the invention.

Further it has been shown in the literature that the use of suitable monoacylphosphonic acid copper salts is advantageous for such applications (Gong et al., *Chem. Commun.* 2013, 49, 7950). The use of bisacylphosphonic acid copper salts of the present invention (divalent (m=2) photoinitiators of structure (II) with $Q^{m+}$ being $Cu^{2+}$) gives the additional advantage of a higher selectivity due to the possible use of light of longer wavelengths. It is possible to prepare and isolate such bisacylphosphonic acid copper salts by a metathesis reaction of an bisacylphosphonic acid salt, for example an ammonium salt, with a copper(II) salt, for example copper(II) sulfate. It is also possible to prepare the bisacylphosphonic acid copper salts in situ by mixing solutions of a bisacylphosphonic acid salt, for example an ammonium salt, with a solution of a copper(II) salt, for example copper(II) sulfate without isolation of the bisacylphosphonic acid copper salt. It is further possible to obtain the bisacylphosphonic acid copper salts by direct reaction of a bisacylphosphonic acid of structure (I) (n=1, Y=O and $R_4$=H) with a suitable copper salt such as $CuSO_4.5\ H_2O$.

Similarly, the photogenerated $Cu^{+1}$ can be used for example as catalyst for copper mediated ATRP-polymerizations. Again the longer absorbance of the photolatent compounds of this invention allows for a better selectivity.

The photoinduced reduction of metal cations to metal is useful for example for the production of conductive materials or metal nanoparticles finely dispersed in a matrix material. Since light is used to control the process, imagewise conductive structures can be obtained. Production of metallic copper is preferred for many applications compared to other metals, due to the lower costs of copper salts as compared to silver or gold salts.

Further of interest is a process as described above for producing pigmented and nonpigmented paints and varnishes, powder coatings, printing inks, printing plates, adhesives, pressure sensitive adhesives, dental compositions, gel coats, photoresists for electronics, electroplating resists, etch resists, both liquid and dry films, solder resists, resists to manufacture color filters for a variety of display applications, resists to generate structures in the manufacturing processes of plasma-display panels, electroluminescence displays and LCD, spacers for LCD, for holographic data storage (HDS), as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, as image recording material, for holographic recordings, microelectronic circuits, decolorizing materials, decolorizing materials for image recording materials, for image recording materials using microcapsules, as a photoresist material for a UV and visible laser direct imaging system, as a photoresist material used for forming dielectric layers in a sequential build-up layer of a printed circuit board; in particular a process for the preparation of pigmented and nonpigmented paints and varnishes, powder coatings, printing inks, e.g. screen printing inks, inks for offset-, flexo- or inkjet printing, printing plates, adhesives, sealings, potting components, dental compositions, foams, moulding compounds, composite compositions, glass fibre cable coatings, screen printing stencils, for producing three-dimensional objects by means of stereolithography, and as image recording material, photoresist compositions, decolorizing materials, decolorizing materials for image recording materials, for image recording materials using microcapsules.

Preferred is a process as described above for the production of pigmented and nonpigmented surface coatings, overprint coatings, powder coatings, printing inks, inkjet inks, gel coats, composite materials or glass fibre coatings.

The invention relates also to a coated substrate which is coated on at least one surface with a composition as described above and irradiated with electromagnetic radiation, as well as a polymerized or crosslinked composition obtained by curing a polymerizable composition as described above.

In particular of interest is the use of a composition as described above as a surface coating for food packaging materials, as well as a process as described above for the production of a surface coating for food packaging materials employing a composition as described above.

The ease of further transformations of the bisacylphosphinic acid of the present invention allows a facile access to a wide variety of bisacylphosphinic acid derivatives possessing very different application properties. For example, derivatives with excellent solubility or compatibility with a highly polar environment such as aqueous formulations are accessible as well as compounds compatible with resins of very low polarity. Further, by simple variations of reagents in the exchange or addition reaction step, physical properties can be varied from high melting compounds to liquid derivatives of low viscosity. Further, the mild reaction conditions required for the modification of the bisacylphosphinic acid derivatives tolerate a wide variety of functional groups. Thus derivatives with reactive groups suitable for further reactions or co-polymerizable derivatives are easily accessible. Moreover the incorporation of other photoinitiator moieties or other additives into the bisacylphosphinic acid structure is possible.

An easy variation of properties in the art is highly desirable for the development of tailor-made photoinitiators.

Monoacyl- and bisacyalphosphine oxides are known to have a limited chemical stability in the presence of nucleophiles such as primary or secondary amines, or in a basic medium. This inherent property considerably limits the application of such photoinitiators to formulations which do neither contain such nucleophiles or bases. However, the use of amines, or amine-modified oligomers, is desirable for applications, e.g. if oxygen inhibition is an important issue. Surprisingly it was found that the bisacylphosphinic acid derivatives of the present invention exhibit a much higher stability towards nucleophiles or basic conditions. Thus they can be used as photoinitiators in formulations containing for example amines, or in aqueous basic systems without compromising on the chemical stability of the photoinitiator.

The fine tuning of absorption properties to the requirements of the application is another important issue for the development of efficient photoinitiators. Since the long-wavelengths absorption is due to the interaction between the phosphinoyl and the carbonyl groups, the influence of substituents on the aroyl group or the P-alykl or P-aryl substituent on the absorption spectra are only of minor importance. It is well known that monoacylphosphine oxides have a more blue-shifted absorption than bisacylphosphine oxides, thereby implying less yellowing in the cured article, but said mono acylphosphine oxides are less efficient as photoinitiators. Surprisingly it is found that modification of the heterosubstituent in the bisacylphosphinic acid derivatives of the present invention has a significant influence on the long-wavelength absorption band of the photoinitiator. Both the type of the hetero atom and the substitution pattern, including steric crowding, has influence on the absorption characteristics.

As an example, simple bisacylphosphinic acid esters exhibit absorption bands that are more blue-shifted than those in P C-substituted bisacylphosphine oxides. Bisacylphosphine oxides with absorption and yellowing properties similar to monoacylphosphine oxides, but the curing performance of bisacylphosphine oxides due to the ability to produce four initiating radicals, become available. Such properties are desirable in applications where high curing efficiency and low yellowing are required, as for example for the curing of white pigmented coatings.

On the other hand, bisacylphosphinic acid amides possessing sterically crowded amine substituents exhibit a more red-shifted absorption spectrum. Thus they provide a higher curing efficiency if light of long wavelengths is used. Such properties are desirable for example for the curing with LED light sources, where narrow banded emission lines of 405 nm or longer wavelenghts are used.

Thus, by suitable selection of the type of substituent on phosphorous, it is possible to finetune the absorption properties of bisacylphosphinic acid to the desired spectral region. Compounds of the present invention, which comprise moieties of polyethyleneglycol, in general liquid compounds with a good compatibility with both non-polar and polar medium such as water-borne formulations, are obtained. Especially the combination of the compatibility of the photoinitiator compound with non-polar (e.g. organic formulation) and polar media (e.g. water-borne formulations) is a highly required property.

The following examples illustrate the invention in more detail, although it is not intended that the invention be limited to the examples. As in the remaining description and in the patent claims, parts or percentages are by weight, unless otherwise stated.

General: Solvents are used as received (without any treatment) or dried over molecular sieves or by azeotropic distillation. The course of the reaction is monitored by 31P-NMR spectroscopy.

EXAMPLE 1

Preparation of bis(2,4,6-trimethyl-benzoyl)-phosphinic acid

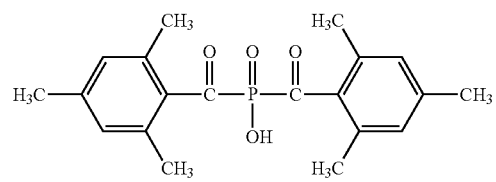

1a) Preparation of Na$_3$P 3.45 g of sodium sand (150 mmol, 3 eq., M=22.99 g/mol), 1.55 g of purified red phosphorous (50.0 mmol, 1 eq., M=30.97 g/mol) and 125 mg of naphthalene (1.0 mmol, M=128.17 g/mol) are suspended in 120 ml of dimethoxyethane (DME). The suspension is heated up to 75° C. and kept at this temperature for 20 h while stirring. A color change from green over red-brown into black takes place.

1b) Preparation of NaPH$_2$

The reaction mixture of step 1a) is cooled down to −10 to −15° C. 10 ml of tert-butanol (0.1 mol, 2 eq., M=74.12 g/mol) in 10 ml DME is added within 20 min while stirring. A nearly clear brown solution is obtained, containing a small amount of unreacted sodium. Stirring is continued for another 20 min.

1c) Preparation of sodium bis(mesitoyl)phosphidexDME, {Na[P(COMes)$_2$]×DME}

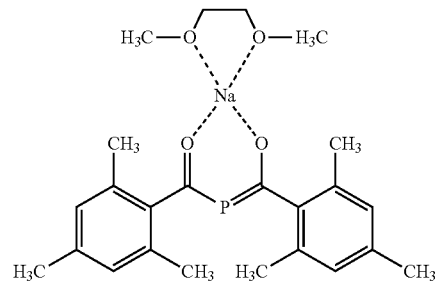

16.8 ml of 2,4,6-trimethylbenzoyl chloride (TMBCl) (0.1 mol, 2 eq., M=182.65 g/mol) are quickly added to the reaction mixture of step 1b), resulting in a color change to yellow. The reaction mixture is stirred for another 20 min under ice cooling, followed by stirring for one hour at room temperature. The $^{31}$P NMR spectrum shows a signal for sodium bis(mesitoyl)phosphidexDME {Na[P(COMes)$_2$]× DME} at 82 ppm (>95%).

1c-1) Isolation of {Na[P(COMes)$_2$]×DME}

The reaction mixture of step 1c) is concentrated under high vacuum. The resulting orange-yellow foam is taken up in 100 ml of toluene and then filtered. The filter cake is washed with toluene providing a clear orange-yellow filtrate solution. The filtrate solution is concentrated under vacuum to a volume of about 70 ml, and then carefully overlaid with hexane (30 ml). Yellow cubic crystals separate from the solution and are identified as sodium bis(mesitoyl)phosphide×DME {Na[P(COMes)$_2$]×DME}(C$_{24}$H$_{32}$NaO$_4$P, M=438.47 g/mol) by $^{31}$P-, $^1$H- and $^{13}$C-NMR spectroscopy. Furthermore, single-crystal X-ray structural analysis shows that the crystals are composed of an ion pair complex of the formula [Na$_3$[P(COMes)$_2$]$_4$][Na(DME)$_3$].

M.p.=208° C. $^{31}$P{H}-NMR (C$_6$D$_6$, 25° C.): δ=84.1 (br.).

1c-2) A DME-free product is obtained if the toluene filtrate solution from step 1c-1) is completely concentrated under vacuum first. The residue is suspended in n-hexane (80 ml), the resulting yellow solid filtered off and then dried under high vacuum. According to NMR spectroscopy measurements, the product consists of DME-free {Na[P(COMes)$_2$]}(C$_{20}$H$_{22}$NaO$_2$P, M=348.35 g/mol).

Alternatively, sodium (bis(mesitoyl)phosphide)×DME can be prepared via acylation with 2,4,6-trimethylbenzoyl chloride of different types of phosphine metal complexes, prepared by one of the following methods described in WO 2006056541:

1. from red phosphorus, lithium powder and naphthalene as a catalyst, but without a proton source (example 2a-c),
2. from red phosphorus, lithium powder, naphthalene and 3-methyl-3-pentanol (example 5a-c),
3. from red phosphorus, lithium granulate, naphthalene and 3-methyl-3-pentanol (example 7a-c)
4. from phosphorus trichloride, sodium and 3-methyl-3-pentanole (example 4a-c) and e) from sodium phosphide and sodium tert-butoxide (examples 12 and 13)].

1d) Bis(2,4,6-trimethyl-benzoyl)-phosphinic acid 5.33 g (15.3 mmol) Sodium bis(mesitoyl)phosphide (prepared according to 1c-1) are dissolved in 20 ml dimethoxyethane in a 150 ml Schlenk flask under inert atmosphere. Acetic acid (0.875 ml, 15.3 mmol) is added while stirring the solution at room temperature. After 3 hours the solvent is removed in vacuo and 30 ml toluene are added to the remaining solid to give a yellow suspension. Sodium acetate is removed by filtration over celite, providing a clear yellowish solution of HP(COMes)$_2$. Subsequently 4 ml of a 30% solution of aqueous hydrogen peroxide (35.2 mmol) are added over 15 minutes at 0° C. under exclusion of light. The mixture is stirred at room temperature overnight, the solution subsequently concentrated and the precipitate isolated by filtration. The white precipitate is washed with hexane (3×10 ml), dissolved in 50 ml THF and the solution dried over sodium sulfate. After filtration the solvent is removed in vacuo, and the residual solid dissolved in 75 ml toluene at 60° C. After slow cooling to −15° C. 4.353 g (12.15 mmol, 80%) bis(2,4,6-trimethyl-benzoyl)-phosphinic acid are obtained as an off-white solid with a melting point of 133° C.

$^1$H-NMR (CDCl3): δ=7.9 (s, 14 H, P—OH), 6.65 (s, 4 H, Mes CH), 2.38 (s, 12 H, Mes o-CH3), 2.13 (s, 6 H, Mes p-CH$_3$).

$^{31}$P-NMR (121.5 MHz, CDCl$_3$): δ=−1.86 ppm.

EXAMPLE 2

Preparation of bis(2,4,6-trimethyl-benzoyl)-phosphinic acid sodium salt

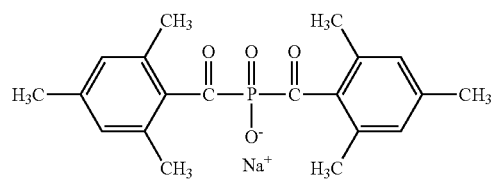

150 mg (0.42 mmol) bis(2,4,6-trimethyl-benzoyl)-phosphinic acid (example 1d) are dissolved in 5 ml ethanol. 35.2 mg (0.42 mmol) sodium hydrogencarbonat are added to this solution while stirring. Stirring is continued for one hour at room temperature and the solvent subsequently removed in vacuo, providing bis(2,4,6-trimethyl-benzoyl)-phosphinic acid sodium salt as a yellow solid.

$^{31}$P-NMR (D$_2$O): δ=0.58 ppm.

EXAMPLE 3

Preparation of bis(2,4,6-trimethyl-benzoyl)-phosphinic acid cyclohexylammonium salt

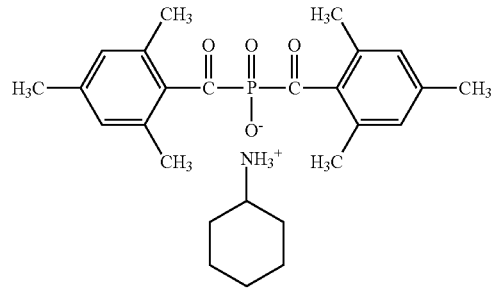

100 mg (0.28 mmol) bis(2,4,6-trimethyl-benzoyl)-phosphinic acid (example 1d) are dissolved in 12 ml methanol. 32 μl (0.28 mmol) cyclohexylamine are added and the solution is stirred for one hour at room temperature. The solvent is removed in vacuo to give bis(2,4,6-trimethyl-benzoyl)-phosphinic acid cyclohexylammonium salt as a yellow solid.

$^{31}$P-NMR (CDCl$_3$): δ=3.55 ppm.

EXAMPLE 4

Preparation of bis(2,4,6-trimethyl-benzoyl)-phosphinic acid imidazolium salt

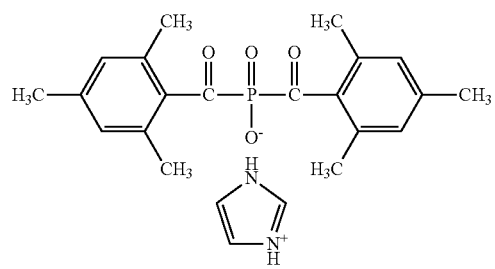

Following the procedure of example 3, but using one equivalent of imidazole instead of cyclohexylamine, (2,4,6-trimethyl-benzoyl)-phosphinic acid imidazolium is obtained as yellowish solid.

<sup>31</sup>P-NMR (CDCl<sub>3</sub>): δ=1.33 ppm.

EXAMPLE 5

Preparation of a mixture of bis(2,4,6-trimethyl-benzoyl)-phosphinic acid 2-hydroxy-prop-1-yl ester and bis(2,4,6-trimethyl-benzoyl)-phosphinic acid 2-hydroxy-2-prop-2-yl ester

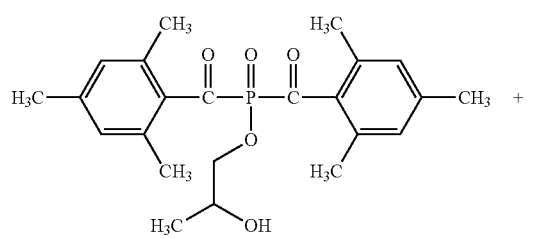

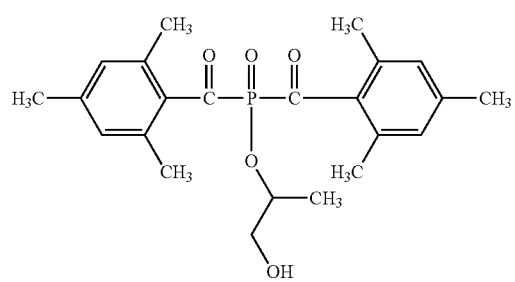

30 mg (0.084 mmol) bis(2,4,6-trimethyl-benzoyl)-phosphinic acid (example 1d) are suspended in 0.5 ml benzene. 48.6 μl (0.084 mmol) 1,2-propylene oxide are added to the suspension while stirring. After 10 minutes of stirring, the reaction mixture becomes a clear yellow solution. $^1$H- and $^{31}$P-NMR analysis of the solution indicates the presence of the two isomeric compounds bis(2,4,6-trimethyl-benzoyl)-phosphinic acid 2-hydroxy-prop-1-yl ester (5a) and bis(2,4,6-trimethyl-benzoyl)-phosphinic acid 2-hydroxy-2-prop-2-yl ester (5b). The product mixture is isolated by evaporation of the solvent in vacuo.

$^{31}$P-NMR (C<sub>6</sub>D<sub>6</sub>): δ=0.0 ppm (4a); δ=−0.03 ppm (4b).

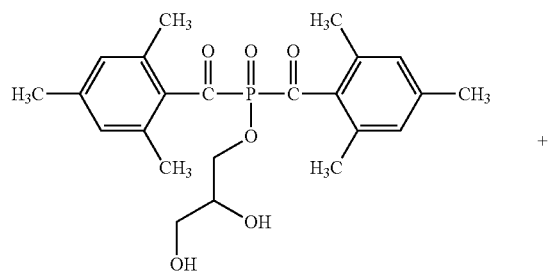

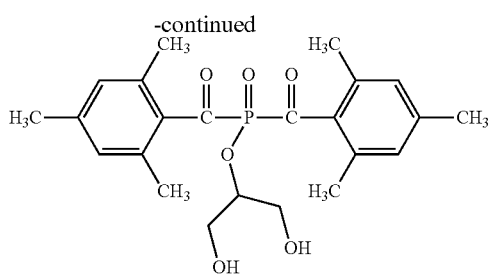

Following the procedure for example 5, but using 3-hydroxy-1,2-propylene oxide (glycidol) instead of 1,2-propylene oxide, a mixture of bis(2,4,6-trimethyl-benzoyl)-phosphinic acid 2,3-dihydroxy-prop-1-yl ester and bis(2,4,6-trimethyl-benzoyl)-phosphinic acid 1,3-dihydroxy-2-prop-2-yl ester is obtained.

$^{31}$P-NMR (CDCl<sub>3</sub>): δ=0.16 ppm (6a); δ=0.18 ppm (6b).

EXAMPLE 7

Preparation of bis(2,4,6-trimethyl-benzoyl)-phosphinic O-[bis(2,4,6-trimethylbenzoyl)phosphinoyl]-N-cyclohexyl urethane

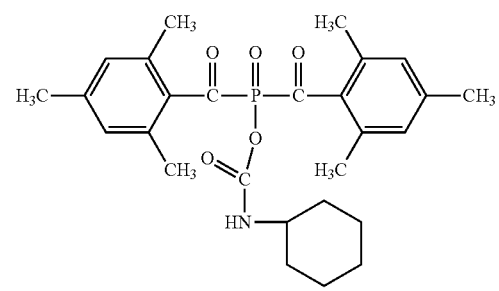

360 mg (1 mmol) bis(2,4,6-trimethyl-benzoyl)-phosphinic acid (example 1d) are dissolved in 10 ml THF. Subsequently 0.13 ml (1 mmol) cyclohexylisocyanate are added while stirring. The addition product which slowly precipitates from the reaction solution as a pale yellow solid is collected by filtration, washed with hexane and dried in vacuo.

$^{31}$P-NMR (d<sub>6</sub>-DMSO): δ=4.47 ppm.

EXAMPLE 8

Preparation of [bis(2,4,6-trimethylbenzoyl)phosphinoyloxy]-ethoxy-dimethyl-silane and di[bis(2,4,6-trimethylbenzoyl)phosphinoyloxy]-dimethyl-silane

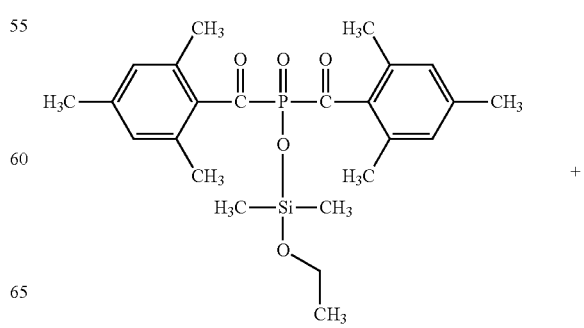

-continued

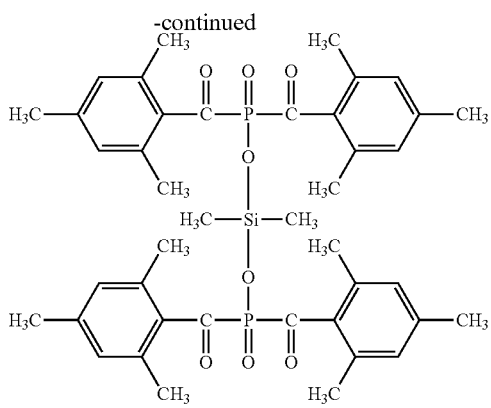

30 mg (0.084 mmol) bis(2,4,6-trimethyl-benzoyl)-phosphinic acid (example 1d) are dissolved in 0.5 ml chloroform and mixed with 14.5 µl (0.084 mmol) diethoxy dimethylsilane. After stirring the solvent is evaporated in vacuo to give the crude product. The NMR spectra indicate the presence of minor amounts of di[bis(2,4,6-trimethyl-benzoyl)]-phosphinyl-dimethyl silane (8b) besides bis(2,4,6-trimethyl-benzoyl)phosphineyl-ethyoxy-dimethyl silane (8a).
$^{31}$P-NMR (CDCl$_3$), 8a: δ=−9.9 ppm

EXAMPLE 9

Preparation of bis(2,4,6-trimethyl-benzoyl)-phosphinic acid chloride with thionyl chloride

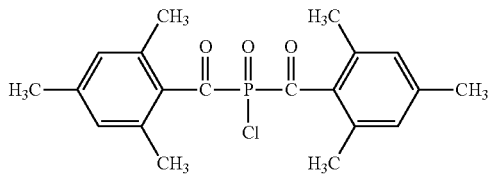

200 mg (0.56 mmol) bis(2,4,6-trimethyl-benzoyl)-phosphinic acid (example 1d) are dissolved in 15 ml toluene. 49 µl (0.67 mmol) Thionyl chloride are added, and the reaction mixture is vigorously stirred over night at room temperature. The solvent is subsequently removed in vacuo to give bis(2,4,6-trimethyl-benzoyl)-phosphinic acid chloride as a pale yellow solid.
$^{31}$P-NMR (CD$_2$Cl$_2$): δ=11.35 ppm.

EXAMPLE 10

Preparation of bis(2,4,6-trimethyl-benzoyl)-phosphinic acid chloride with oxalyl chloride

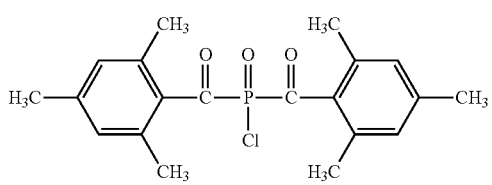

To a solution of 2.15 g (6 mmol) of bis(2,4,6-trimethyl-benzoyl)-phosphinic acid (example 1d) in 30 ml dry THF at 0° C. under argon 2.05 ml (3.1 g, 24 mmol) of oxallyl chloride is added dropwise over 5 minutes. A slight increase in temperature is observed. The reaction mixture is allowed to warm to ambient temperature and stirred for 2.5 h to remove all volatiles under vacuum. The acid chloride is characterized by a peak at 10.1 ppm in the $^{31}$P NMR (CDCl$_3$) spectrum. The product is not isolated but used in situ for the reaction of example 12.

EXAMPLE 11

Preparation of bis(2,4,6-trimethyl-benzoyl)-phosphinic acid chloride from bis(2,4,6-trimethyl-benzoyl)-phosphinic acid sodium salt

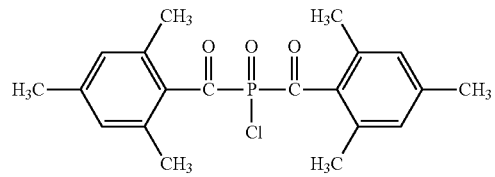

Bis(2,4,6-trimethyl-benzoyl)-phosphinic acid (example 1d) (1.9503 g, 5.44 mmol, 1 eq.) is dissolved in ethanol (15 ml) in a 50 mL Schlenk flask. Subsequently, NaHCO$_3$ (0.548 g, 6.53 mmol, 1.2 eq.) is added to the stirred solution at room temperature. After 1 h, the solvent is removed in vacuo and the yellow solid obtained is dried under high vacuum. The product is suspended in THF (50 mL) under argon and oxalyl chloride (1.5 mL, 17.47 mmol, 3.2 eq.) and DMF (50 µl, 0.65 mmol, 12 mol-%) are added dropwise. The reaction mixture is stirred vigorously at room temperature for 12 h and concentrated in vacuo to remove excess oxalyl chloride. The product thus obtained is not isolated but used in situ for the reactions of examples 14 and 20-23.

EXAMPLE 12

Preparation of bis(2,4,6-trimethyl-benzoyl)-phosphinic acid ethyl ester

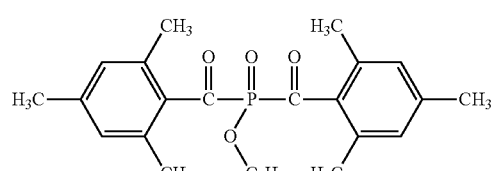

To a solution of the crude bis(2,4,6-trimethyl-benzoyl)-phosphinic acid chloride (example 9) in 40 ml of dry toluene and 1.1 ml (0.8 g, 8 mmol) of triethylamine is added dropwise at ambient temperature 3.5 ml (2.76 g, 60 mmol) of ethanol over 5 minutes. An increase in temperature is observed. After stirring for 15 h, the reaction mixture is poured into water and extracted with ethyl acetate (3×20 ml). The combined organic extracts are washed with brine, dried (MgSO$_4$) and concentrated to give 2.2 g of a yellow oil which crystallized slowly at room temperature. Recrystallization from 10:1 heptane/ethylacetate gives 0.52 g (22%) of a white solid. Column chromatography of the concentrated mother liquor on silica with 6:1 hexane:ethylacetate gives an additional 0.75 g (total yield 57%) of the white solid: mp 114-118° C.

$^1$H-NMR (CDCl$_3$): δ=6.88 (s, 4), 4.01 (pentet, 2, J=7.2 Hz), 2.35 (s, 12), 2.30 (s, 6) and 1.14 (t, 3, J=5.2 Hz) ppm; $^{31}$P-NMR (CDCl$_3$): δ=−0.43 ppm.

EXAMPLE 13

Preparation of bis(2,4,6-trimethyl-benzoyl)-phosphinic acid 3-[4-{2'-hydroxy-2'-methyl-propanoyl}phenyl]-propyl ester

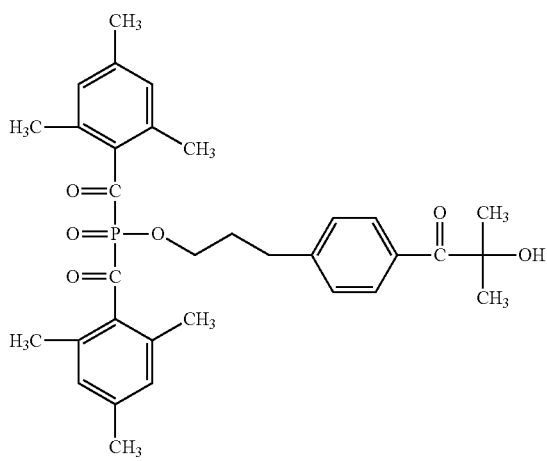 [SMILES: Cc1cc(C)c(C(=O)P(=O)(OCCCc2ccc(C(=O)C(C)(C)O)cc2)C(=O)c2c(C)cc(C)cc2C)c(C)c1]

210 mg (0.56 mmol) bis(2,4,6-trimethyl-benzoyl)-phosphinic acid chloride (example 9) are dissolved in 4 ml dichloromethane. This solution is added dropwise using a teflon syringe filter to a solution of 24 mg (0.56 mmol) [4'-(3"-hydroxypropyl)-phenyl]-2-hydroxy-2-methyl-propan-1-one in 4 ml dichloromethane at 0° C. The reaction mixture is allowed to warm-up to room temperature and stirred overnight, while evolving gaseous hydrogen chloride is drained off from the reaction vessel. Bis(2,4,6-trimethyl-benzoyl)-phosphinic acid 3-[4-{2'-hydroxy-2'-methyl-propanoyl}phenyl]-propyl ester is isolated as a yellow solid. The structure is confirmed by an X-ray analysis. $^{31}$P-NMR (CH$_2$Cl$_2$): δ=0.28 ppm.

EXAMPLE 14

Preparation of bis(2,4,6-trimethyl-benzoyl)-phosphinic acid 2-[4-{2'-hydroxy-2'-methyl-propanoyl}phenyloxy]-ethyl ester

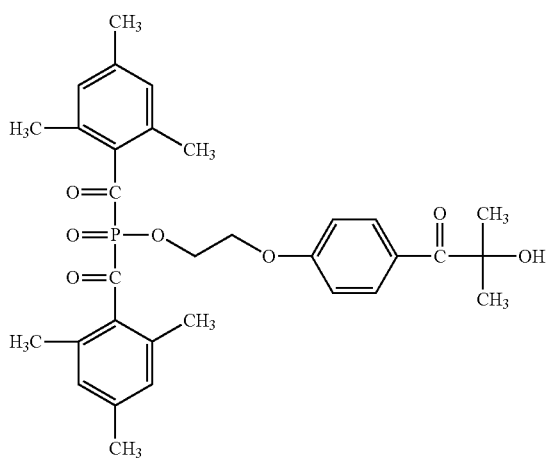 [SMILES: Cc1cc(C)c(C(=O)P(=O)(OCCOc2ccc(C(=O)C(C)(C)O)cc2)C(=O)c2c(C)cc(C)cc2C)c(C)c1]

The crude bis(2,4,6-trimethyl-benzoyl)-phosphinic acid chloride (5.45 mmol, 1 eq.), prepared according to example 11, is dissolved in dichloromethane (20 ml) and the solution is subsequently added dropwise at room temperature to a solution of Irgacure® 2959 (=4[(2-hydroxyethoxy)-benzoyl]-1-hydroxy-1-methyl ethan) (1.595 g, 7.12 mmol, 1 eq.) in dichloromethane (40 ml). The reaction mixture is stirred at room temperature for 12 h. The solvent is removed under reduced pressure. After recrystallization from a toluene/hexane mixture (10 ml/5 ml, −15° C.), bis(2,4,6-trimethyl-benzoyl)-phosphinic acid 2-[4-{2'-hydroxy-2'-methyl-propanoyl}phenyloxy]-ethyl ester is obtained as a pale yellow (3.66 g, 91%).

$^{31}$P-NMR (C$_6$D$_6$): δ=0.710 ppm.

EXAMPLE 15

Preparation of bis(2,4,6-trimethyl-benzoyl)-phosphinic acid N-cyclohexylamide 1-[bis(2,4,6-trimethyl-benzoyl-phosphinyl]-piperidine

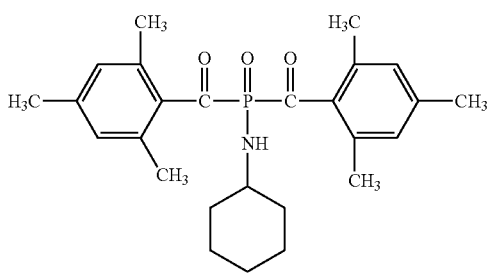

217 mg (0.575 mmol) bis(2,4,6-trimethyl-benzoyl)-phosphinic acid chloride (example 8) are dissolved in 4 ml dichloromethane. To the clear yellow solution thus obtained, 67 μl (0.575 mmol) cyclohexylamine and 80 μl triethylamine (0.575 mmol) in 2 ml dichloromethane are added dropwise while stirring. After 12 hours at room temperature the solvent is removed in vacuo to give bis(2,4,6-trimethyl-benzoyl)-phosphinic acid N-cyclohexylamide as yellow solid. The structure is confirmed by an X-ray analysis.

$^{31}$P-NMR (C$_6$D$_6$): δ=4.40 ppm.

EXAMPLE 16

Preparation of bis(2,4,6-trimethyl-benzoyl)-phosphinothionic acid S-phenyl ester

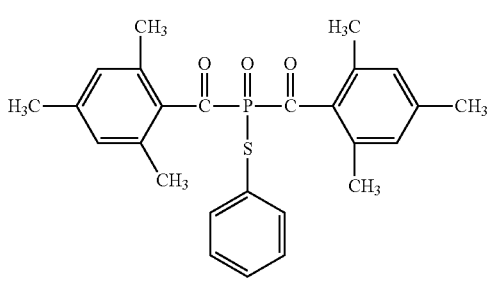

210 mg (0.56 mmol) bis(2,4,6-trimethyl-benzoyl)-phosphinic acid chloride (example 8) are dissolved in 4 ml dichloromethane. The solution is added dropwise through a teflon syringe filter to 68.5 μl (0.56 mmol) sodium thiophenolate dissolved in 4 ml dichloromethane. The reaction mixture is stirred at room temperature during 12 hours while sodium chloride precipitates. After filtration, the solvent is removed in vacuo, to give bis(2,4,6-trimethyl-benzoyl)-phosphinothionic acid S-phenyl ester as a yellow solid.

$^{31}$P-NMR (CH$_2$Cl$_2$): δ=−0.39 ppm.

EXAMPLE 17

Preparation of bis(2,4,6-trimethyl-benzoyl)-phosphinodithioic acid triethylammonium salt

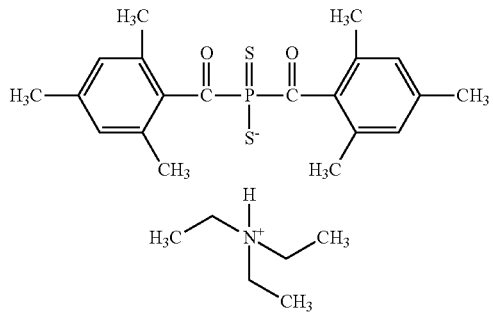

A mixture of 0.664 g (2.03 mmol) HP(COMes)$_2$ (Mes=mesityl; prepared as reported in example 1d) and 0.283 ml (2.03 mol) triethylamine in 8 ml toluene is prepared in a 50 ml Schlenk tube under argon atmosphere. Subsequently 0.143 g (4.46 mmol) elemental sulfur are added to the mixture while stirring at room temperature. After one hour, excess sulfur is removed by filtration, and the solvent is evaporated from the filtrate in vacuo to give 0.92 g (1.87 mmol) of bis(2,4,6-trimethyl-benzoyl)-phosphinodithioic acid triethylammonium salt as yellow salt.

$^1$H NMR (C$_6$D$_6$,): δ=9.13 (s, 1 H, N—H); 6.83 (s, 4 H, Mes CH), 2.93 (s, 12 H, Mes o-CH$_3$), 2.40 (q, 6 H, NCH$_2$ CH$_3$), 2.21 (s, 6 H, Mes p-CH$_3$) 0.71 (t, 9 H, NCH$_2$ CH$_3$), $^{31}$P-NMR (C$_6$D$_6$): δ=63.54 ppm.

EXAMPLE 18

Preparation of bis(2,4,6-trimethyl-benzoyl)-phosphinic acid 2-[2-(2-methoxyethyloxy)ethyloxy]ethyl ester

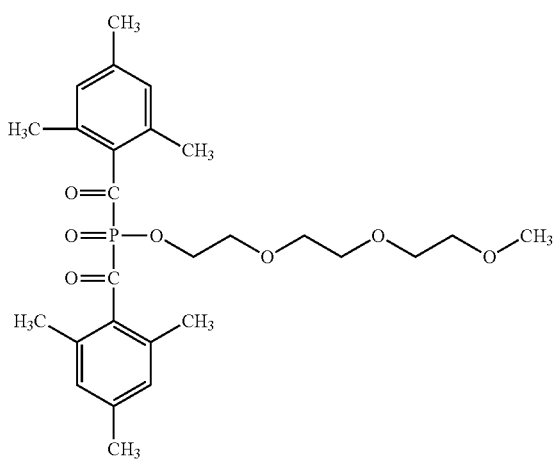

The crude yellow bis(2,4,6-trimethyl-benzoyl)-phosphinic acid chloride prepared as example 11 is dissolved in dichloromethane (20 ml). A solution of triethylene glycol monomethyl ether (0.853 mL, 5.44 mmol, 1 eq.) and triethylamine (0.756 ml, 5.44 mmol, 1 eq.) in dichloromethane (10 ml) is added dropwise to solution of bis(2,4,6-trimethyl-benzoyl)phosphinic acid chloride. The reaction mixture is stirred at room temperature for 12 h, the solution subsequently diluted with dichloromethane (100 mL) and extracted with aq. HCl (0.1 M, 2×50 ml). The organic phase is dried over NaSO$_4$, filtered and concentrated in vacuo to yield bis(2,4,6-trimethyl-benzoyl)-phosphinic acid 2-[2-(2-methoxyethyloxy)ethyloxy]ethyl ester as an orange oil.

$^{31}$P-NMR (CH$_2$Cl$_2$): δ=−4.984 ppm.

EXAMPLE 19

Preparation of bis(2,4,6-trimethyl-benzoyl)-phosphinic acid ester of Pluriol A 350

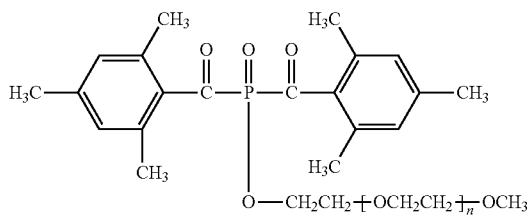

n = appropximately 6

The compound of this example is prepared as example 18 except that Pluriol A 350 (available from BASF SE, a technical mixture of polyethylene glycol monomethyl ethers with an average of six ethylene glycol moieties and an average molecular weight of approximately 680 D) is used instead of triethylene glycol monomethyl ether. The bis(2,4,6-trimethyl-benzoyl)-phosphinic acid ester of Pluriol A 350 is obtained as an orange oil. $^{31}$P-NMR (CDCl$_3$): δ=0.01 ppm.

EXAMPLE 20

Preparation of bis(2,4,6-trimethyl-benzoyl)-phosphinic hexyl ester

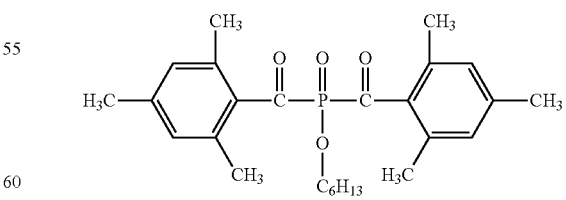

The compound of example 20 is prepared as described in example 18, except that n-hexanol is used instead of triethylene glycol monomethyl ether. The bis(2,4,6-trimethyl-benzoyl)-phosphinic acid hexyl ester is obtained as an yellow solid. $^{31}$P-NMR (CDCl$_3$): δ=−0.51 ppm.

EXAMPLE 21

Preparation of bis(2,4,6-trimethyl-benzoyl)-phosphinic acid dodecyl-thioester

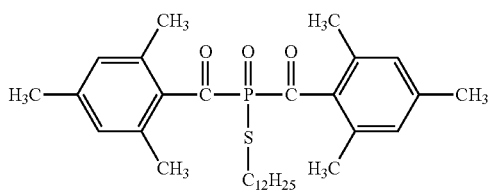

The crude yellow bis(2,4,6-trimethyl-benzoyl)-phosphinic acid chloride (5.45 mmol, 1 eq.), prepared according to example 11, is dissolved in dichloromethane (20 mL). A solution of 1-dodecanethiol (1.305 ml, 5.45 mmol, 1 eq.) and triethylamine (0.758 ml, 5.45 mmol, 1 eq.) in dichloromethane (10 ml) is added dropwise to solution of phosphinic acid chloride. The reaction mixture is stirred at room temperature for 12 h, followed (15 ml), the precipitate of $N(C_2H_5)_3 \cdot HCl$ is removed by filtration and the solvent evaporated in vacuo to yield bis(2,4,6-trimethyl-benzoyl)-phosphinic acid dodecylthioester as an orange oil.

$^{31}$P-NMR ($CH_2Cl_2$): δ=21.836 ppm.

EXAMPLE 22

Preparation of bis(2,4,6-trimethyl-benzoyl)-phosphinic acid trioctylmethyl ammonium salt

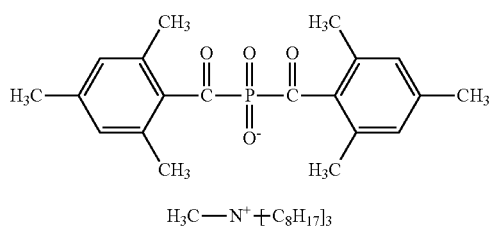

The compound of example 22 is prepared by a salt methathesis reaction of bis(2,4,6-trimethyl-benzoyl)-phosphinic acid sodium salt (example 2) with trioctylmethyl ammonium chloride (Aliquat 336, Sigma-Aldrich). Equimolar amounts of the sodium salt and Aliquat 336 are supended in dichloromethane while stirring. After 12 hours at room temperature the precipitated sodium chloride is filtered off and the solvent is evaporated in vacuo, in dihloromethane. The yellowish bis(2,4,6-trimethl-enzoyl-benzoyl)-phosphinic acid trioctylmethyl ammonium salt thus obtained has the typical properties of an ionic liquid, being a high viscous semi-solid at room temperature, but becoming a low viscous liquid at elevated temperature.

$^{31}$P-NMR ($CDCl_3$): δ=2.73 ppm.

EXAMPLE 23

Preparation of tetraethylene glycol bis(2,4,6-trimethylbenzoyl)-phosphinic acid diester
(a)

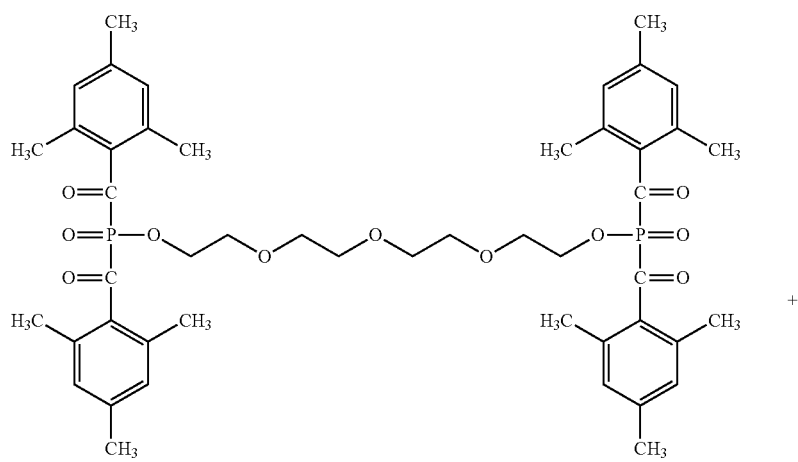

(a)

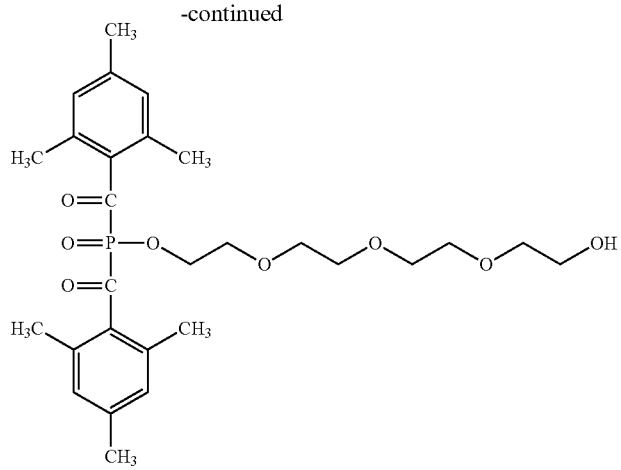

(b)

The compound of this example is prepared as the one of example 18, except that 0.5 equivalents of tetraethylene glycol are used instead of 1 equivalent triethylene glycol monomethyl ether. The tetraethylene glycol bis(2,4,6-trimethyl-benzoyl)-phosphinic acid diester a is obtained as a yellow oil. According to NMR analysis, the material contains minor amounts of bis(2,4,6-trimethyl-benzoyl)-phosphinic acid 2-{2-[2-(2-hydroxyethyloxy)ethyloxy]ethyloxy}ethyl ester b.

$^{31}$P-NMR (CDCl$_3$): δ=−0.37 ppm (compound a), −3.02 (compound b).

EXAMPLE 24

Preparation of copper(II) bis(2,4,6-trimethyl-benzoyl)-phosphinate

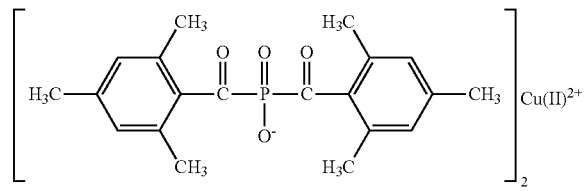

The compound of example 24 is prepared by mixing in a 10 mL round-bottom flask CuSO$_4$.5H$_2$O (41 mg, 0.165 mmol, 1 eq.) and bis(2,4,6-trimethyl-benzoyl)-phosphinic acid sodium salt (example 2, 118 mg, 0.33 mmol) in 5 ml of water. The suspension is kept in an ultrasound bath for 1 hour before heating the mixture to 60° C. whilst stirring for 2 hours. The precipitated greenish-yellow solid of is filtered off and dried in vacuo for 6 hours to give 120 mg (89%) copper(III) bis(2,4,6-trimethyl-benzoyl)-phosphinate.

$^{31}$P-NMR (D$_2$O): 6=0.81 ppm.

APPLICATION EXAMPLES

Example A1

Curing of a White Urethane Acrylate Varnish Formulation

1% w/w of the photoinitiator of example 9 is dissolved together with 3% of Irgacure® 184 (=phenyl-1-hydroxycyclohexyl ketone, BASF SE) at 60° C. in a aliphatic urethane acrylate formulation consisting of 80% Laromer LR 8987 (urethane acrylate, BASF), 0.025% Byk 307 (silicon surface additive) and 0.2% disperbyk (dispersing agent). When all photoinitiator is dissolved 20% titanium dioxide (CL2300) are incorporated and dispersed during three hours with glass pearls in a Skandex shaking apparatus. Subsequently the white varnish formulation is applied as a 4 μm film on an aluminum foil. The sample is passed under a mercury medium pressure lamp (80 W/cm).

Complete curing is tested in a REL curing tester immediately after the irradiation. In this, an aluminum cylinder over which fabric is stretched is placed on the printed sample and rotated once around its own axis under a pressure of 220 g/cm$^2$ in the course of 10 seconds. If thereby visible damage is caused to the sample, the formulation has not completely cured sufficiently. The maximum rate of transportation at which the REL test is still passed is determined.

The lacquer is fully cured at a belt speed of 70 m/min.

Example A2

Photoinitiator Performance in a White Pigmented Photocurable Polyetheracrylate Formulation The following white pigmented Formulations 2a-2c are prepared;

The basic white photocurable formulation is prepared by mixing:
- 58.3 g of an amine modified polyetheracrylate (PO94F provided by BASF)
- 16.0 g of a polyester acrylate (Laromer® PE9079, provided by BASF SE)
- 0.2 g of a slip aid (EFKA® 3030, provided by BASF SE)
- 0.5 g of a wetting aid (EFKA® 5220, provided by BASF SE)
- 21.0 g of titanium dioxide To the basic formulation the following amounts of photoinitiators are added:

Formulation 2a: 1.0 g of the photoinitiator according to example 17 and 3.0 g Irgacure® 184 (provided by BASF SE)

Formulation 2b: 1.0 g of the photoinitiator according to example 19 and 3.0 g Irgacure® 184 (provided by BASF SE)

Formulation 2c: 1.0 g of the photoinitiator according to example 23 and 3.0 g Irgacure® 184 (provided by BASF SE)

A2.1: Reactivity

The formulation to be tested is applied with a bar coater on white coil with a thickness of 24 μm. Curing of the formulation is achieved by moving the sample on a belt under a UV Hg high pressure lamp (200 W/cm) with a defined speed. The highest speed which can be used to fully cure the formulation is determined (Full cure is determined by finger nail scratching). The results are collected in the following table 1.

A2.2: Yellowing

The formulation to be tested is applied on white coil with a thickness of 100 μm. Curing of the formulation is achieved by moving the sample on a belt under a high pressure Hg lamp (200 W/cm) at a belt speed of 5 m/min. The yellowing of the formulation is determined directly after curing, after 1 h, after 72 h and after further irradiation with a TL03 lamp, via colorimetric determination of the b* value according to the Cielab system. The higher the value, the more yellowish is the cured coating. The results are collected in the following table 1.

A2.3 Pendulum Hardness

The formulation to be tested is applied on white coil with a thickness of 100 μm. Curing of the formulation is achieved by moving the sample on a belt under a high pressure Hg lamp (200 W/cm) at a belt speed of 5 m/min. The pendulum hardness (PH) in seconds according to König DIN 53157 is determined directly after curing and 72 h after storing in a temperature-controlled room at 22° C. The higher the PH value, the more reactive is the tested photoinitiator compound. The results are collected in the following table 1.

A2.4: Maximum Curable Film Thickness

The formulations are poured into a lid of a polyethylene cup, so that the wet thickness is about 2 mm and cured with a 200 W gallium-doped mercury medium pressure lamp by passing the samples on a belt under the lamp with a belt speed of 5 m/min. Then the cured layer is removed from the lid and any uncured material is removed with acetone, dried and the thickness of the sample is measured.

Determined is the maximum film thickness curable under these conditions. The results are collected in the following table 1.

TABLE 1

| Example | Formulation 2a | Formulation 2b | Formulation 2c |
|---|---|---|---|
| A2.1; reactivity: belt speed [m/min] | 30 | 15 | 40 |
| A4.2: yellowing | | | |
| b* directly after curing | 1.3 | 1.5 | 1.3 |
| b* after 1 h | 1.3 | 1.5 | 1.3 |
| b* after 72 h | 1.5 | 1.4 | 1.5 |
| b* after further irradiation | 0.3 | 0.4 | 0.0 |
| A4.3: pendulum hardness [s] | | | |
| directly after curing | 28 | 29 | 27 |
| after 72 h | 48 | 39 | 48 |
| A4.4: maximum film thickness cured [μm] | 242 | 209 | 200 |

Example A3

Curing of a Water-borne Clear Lacquer

1% w/w of the photoinitiator of example 1 is dissolved together with 1% of Irgacure® 500 (=1:1 mixture of phenyl-1-hydroxycyclohexyl ketone and benzophenone; BASF SE) in a formulation consisting of 80% Laromer UA 9064 (urethane acrylate, BASF), 4% DSX 1550 (5% in water, polyurethane thickener, BASF), 3.8% Lubaprint (wax dispersion, Bader), Efka 2526 (defoamer, BASF), Byk 346 (surfactant, Byk) in 11.9% water.

The water-borne formulation is applied as a 100 μm wet film on a white coil coat and passed under a mercury medium pressure lamp (1200 W/cm) at a belt speed of 10 m/min. A fully cured lacquer is thus obtained.

Example A4

Photoinitiator Performance in a Photocurable Water-Borne Clear Varnish Formulation The following water-borne clear Formulations 4a-4c are prepared:

The basic clear varnish formulation is prepared by mixing:
  83.6 g of a water-based urethane acrylate dispersion (Laromer® UA 9064, provided by BASF SE)
  4.2 g of a rheology modifier (DSX 1550, 5% in water, provided by BASF SE)
  0.2 g of a defoaming agent (EFKA 2526, provided by BASF SE)
  0.1 g of a wetting agent (BYK 347, provided by BYK)

Preparation of formulations 4a and 4b: For the preparation of these formulations, 11.9 g water are added to 88.1 g of the basic clear varnish formulation. To 98 g of this water-diluted basic formulation the following amounts of photoinitiators are added:

Formulation 4a: 1.0 g of the photoinitiator according to example 18 and 1.0 g Irgacure® 500 (provided by BASF SE)

Formulation 4b: 1.0 g of the photoinitiator according to example 19 and 1.0 g Irgacure® 500 (provided by BASF SE)

Preparation of formulation 4c: Due to the low solubility of the photoinitiator of example 1 in water, the compound is first transformed into its ammonium salt for the preparation of the formulation 4c of example A4. Thus, one g of the photoinitiator is dispersed in 11.9 g water, followed by the addition of diethanol amine to adjust the pH to 9. 12.9 g of the clear aqueous solution thus obtained, containing the diethanolammonium salt of photoinitiator 1, are then added to the formulation, instead of 11.9 g water and 1 g photoinitiator as used for the formulations 4a and 4c of example A4.

To 88.1 g of the basic clear formulation the following amounts of photoinitiators are added:

Formulation 4c: 12.9 g of the solution of 1.0 g of the photoinitiator according to example 1 in 11.9 g water and 1.0 g Irgacure® 500 (provided by BASF SE)

All formulations 4a-4c thus contain equal amounts of water (11.7 g) and of the corresponding photoinitiators (1 g).

A4.1: Reactivity

The formulation to be tested is applied on glass plate with a wet thickness of 100 μm. The plates are then dried at 60° C. for 5 min. Curing of the formulation is achieved by moving the sample on a belt under one Hg lamp (120 W/cm) with at a belt speed of 30 m/min. Reactivity (surface cure and through cure) is measured using the MEK double rub test one minute after irradiation. A methyl ethyl ketone (MEK) soaked cotton ball is rubbed until the surface of the coating starts to be affected (usually visualized by the gloss reduction). This corresponds to surface cure, i.e. the number of double rubs until the surface starts to be affected. Then the rubbing procedure is pursued until the whole coating is destroyed and removed from the substrate (easily visualized from seeing the substrate in the area where the rubbing was carried out). The number of double rubs required to remove the coating from the substrate corresponds to the evaluation of the through-cure of the coating. The higher the number of double rubs required to damage the surface or to remove the coating, the better is the surface or through cure.

A4.2: Yellowing

The formulation to be tested is applied on white coil coat with a wet thickness of 100 μm. The panels are then dried at 60° C. for 5 min. Curing of the formulation is achieved by moving the sample on a belt under one Hg lamp (200 W/cm) with at a belt speed of 5 m/min. The yellowing of the formulation is determined directly after curing, after 1 h, after 72 h and after irradiation with a TL03 lamp for 16 hours, via colorimetric determination of the b* value according to the Cielab system. The higher the value, the more yellowish is the cured coating.

The results are collected in the following table 2.

TABLE 2

| Example | Formulation 4a | Formulation 4b | Formulation 4c |
|---|---|---|---|
| A4.1: reactivity; double rubs | | | |
| surface cure | 40 | 17 | 8 |
| through cure | 140 | 23 | 50 |
| A4.2: yellowing | | | |
| b* directly after curing | 2.6 | 2.5 | 3.9 |
| b* after 1 h | 0.7 | 0.6 | 2.1 |
| b* after 72 h | −0.3 | −1.6 | −0.3 |
| b* after 16 h irradiation | −1.9 | −2.3 | −1.7 |

Example A5

Solubility in Water 50 mg of the photoinitiator of example 1 is added to 1 ml of distilled water and the suspension stirred at room temperature for 60 minutes. Non-dissolved material is filtered off, dried in vacuo and weighed. The solubility is approximately 5 mg/ml.

Example A6

Stability in an Aqueous Basic Environment

A solution of the photoinitiator of example 1 (x mg in y ml water, c=XY mol/l) is adjusted to pH 11 using a buffer solution. An UV spectrum of the fresh solution is measured and the solution subsequently stored in the dark at ambient temperature. UV spectra are measured at regular intervals and checked against the spectrum of the fresh solution. A diminution of the long-wavelength absorbance is indicative for a base-catalyzed hydrolysis of the compound. The solution is found to be stable (less than 3% decomposition) over a period of 12 weeks.

Example A7

Preparation of Copper(0) Nanoparticles

Stability in an aqueous basic environment

A degassed solution of copper(II) sulphate ($CuSO_4 \cdot 5H_2O$, 0.017 M) and an equimolar amount of bis(2,4,6-trimethyl-benzoyl)-phosphinic acid (example 1) in 15 ml of water is prepared in a glass test tube sealed with a septum. Different amounts of poly(vinylpyrrolidone) (PVP) are added to this solution (c(PVP=0.10, 0.20, 0.27 and 0.50 g) resulting in yellow turbid (c(PVP=0.10 and 0.20 g) or clear (c(PVP=0.27 and 0.50 g) solutions. Subsequently the samples are irradiated with vigorous stirring for two hours. All solutions turn into red-brown suspensions upon irradiation. 10 ml of ethanol is added to each sample and sedimentation of the suspended copper is achieved by centrifugation (20'000 rpm, 15 min). The supernatant liquid is removed and the brown-red metallic residue washed twice with 5 ml of ethanol. Both x-ray powder diffraction and XPS (X-ray photoelectron spectroscopy) analysis of all samples obtained confirm that the material consists of elemental copper.

The invention claimed is:

1. Bisacylphosphine oxide or bisacylphosphine sulfide compounds of formula (II)

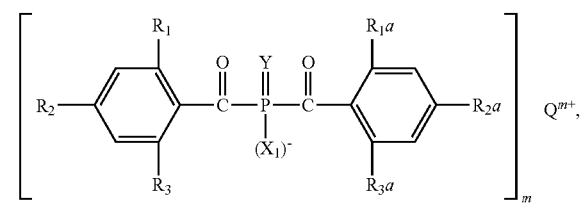

(II)

wherein
$R_1$, $R_2$, $R_3$, $R_{1a}$, $R_{2a}$ and $R_{3a}$ independently of each other are $C_1$-$C_4$-alkyl, $C_1$-$C_4$-alkoxy or halogen;
Y is O or S;
$X_1$ is O or S;
m is 1, 2 or 3;
Q is an inorganic or organic cation.

2. The bisacylphosphine oxide or bisacylphosphine sulfide compounds of formula (II) according to claim 1, wherein
$R_1$, $R_2$, $R_3$, $R_{1a}$, $R_{2a}$ and $R_{3a}$ independently of each other are $C_1$-$C_4$-alkyl;
Y is O or S;
$X_1$ is O or S;
m is 1.

3. A process for the preparation of bisacylphosphinic acid compounds and bisacylthiophosphinic acid compounds of formula (II) as claimed in claim 1, wherein
$X_1$ and Y are identical and are O or S;
$R_1$, $R_2$, $R_3$, $R_{1a}$, $R_{2a}$ and $R_{3a}$ independently of each other are $C_1$-$C_4$-alkyl, $C_1$-$C_4$-alkoxy or halogen;
m is 1 or 2;
Q is an inorganic or organic cation which comprises
a1) reacting a metallized phosphine complex of the formula (X) or a phosphine of the formula (XI)

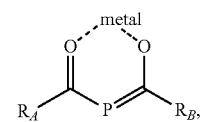

(X)

-continued

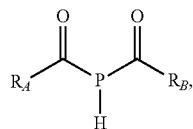
(XI)

wherein $R_A$ is a group

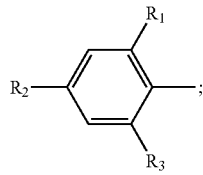

$R_B$ is a group

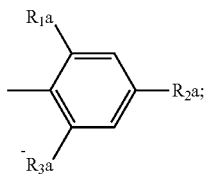

and $R_1$, $R_2$, $R_3$, $R_{1a}$, $R_{2a}$ and $R_{3a}$ are as defined above;

with an oxidation agent, in the presence of a base, to obtain compounds of formula (II), wherein $X_1$ and Y are O;

or a2) reacting a metallized phosphine complex of the formula (X) or a phosphine of the formula (XI) as defined above, with a sulfuration agent, in the presence of a base to obtain compounds of formula (II), wherein $X_1$ and Y are S.

4. A process for the preparation of compounds of the formula (II) as claimed in claim 1, which comprises reacting a compound of formula (II), wherein $X_1$ and Y are O, or of formula (II), wherein $X_1$ and Y are S, with a suitable electrophilic reagent.

5. A process for the preparation of compounds of the formula (II), as defined in claim 3, wherein $R_1$, $R_2$, $R_3$, $R_{1a}$, $R_{2a}$, $R_{3a}$, Q and Y are as defined in claim 3;

by reacting a compound of the formula (Ia)

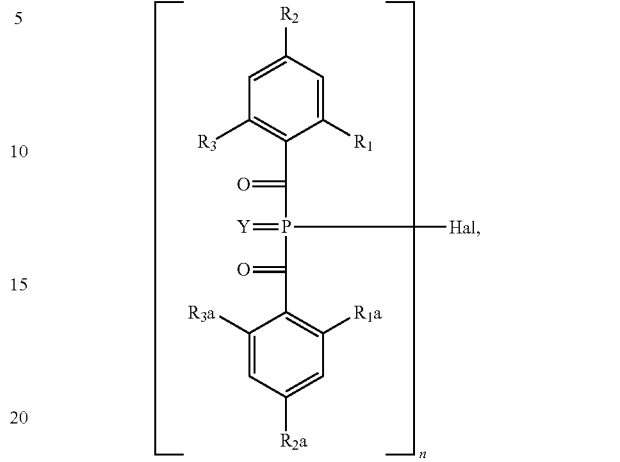

with a suitable nucleophilic reagent.

6. A photopolymerizable composition comprising
(a) at least one ethylenically unsaturated photopolymerizable compound and
(b) as photoinitiator, at least one compound of the formula (II) as defined in claim 1.

7. A photopolymerizable composition according to claim 6, additionally to the photoinitiator (b) comprising at least one further photoinitiator (c), and/or other additives (d).

8. A photopolymerizable composition according to claim 7, wherein further additive (d) comprises a pigment or a mixture of pigments or a mixture of one or more pigments with one or more dyes.

9. A photopolymerizable composition according to claim 7, wherein additive (d) comprises a dispersant or a mixture of dispersants.

10. A photopolymerizable composition according to claim 6, further comprising 0.05 to 25% by weight of the photoinitiator (b), or the photoinitiators (b) and (c), based on the composition.

11. A photopolymerizable composition according to claim 6, wherein additive (d) comprises a photosensitizer.

12. A process for the photopolymerization of compounds containing ethylenically unsaturated double bonds, which comprises irradiating a photopolymerizable composition according to claim 6 with electromagnetic radiation in a range from 150 to 600 nm, or with electron beam or with X-rays.

13. A process according to claim 12 for producing pigmented and nonpigmented paints and varnishes, powder coatings, printing inks, printing plates, adhesives, dental compositions, gel coats, photoresists for electronics, etch resists, both liquid and dry films, solder resists, resists to manufacture color filters for a variety of display applications, for encapsulating electrical and electronic components, for producing magnetic recording materials, micromechanical parts, waveguides, optical switches, plating masks, colour proofing systems, glass fibre cable coatings, screen printing stencils, three-dimensional objects by means of stereolithography, image recording materials, microelectronic circuits, decolorizing materials, formulations containing microcapsules and for forming dielectric layers in a sequential build-up layer of a printed circuit board.

14. A coated substrate which is coated on at least one surface with the composition according to claim 6.

15. A process for producing pigmented and nonpigmented paints and varnishes, powder coatings, printing inks, printing plates, adhesives, dental compositions, gel coats, photoresists for electronics, etch resists, both liquid and dry films, solder resists, resists to manufacture color filters for a variety of display applications, for encapsulating electrical and electronic components, for producing magnetic recording materials, micromechanical parts, waveguides, optical switches, plating masks, colour proofing systems, glass fibre cable coatings, screen printing stencils, three-dimensional objects by means of stereolithography, image recording materials, microelectronic circuits, decolorizing materials, formulations containing microcapsules and for forming dielectric layers in a sequential build-up layer of a printed circuit board which comprises using the composition according to claim 6.

16. A process for photopolymerizing of compounds containing ethylenically unsaturated double bonds using the compound of formula (II) as claimed in claim 1 as a photoinitiator.

\* \* \* \* \*